(12) United States Patent
Beigelman et al.

(10) Patent No.: US 6,686,463 B2
(45) Date of Patent: Feb. 3, 2004

(54) METHODS FOR SYNTHESIZING NUCLEOSIDES, NUCLEOSIDE DERIVATIVES AND NON-NUCLEOSIDE DERIVATIVES

(75) Inventors: Leonid Beigelman, Longmont, CO (US); Alexander Karpeisky, Lafayette, CO (US); Vladmir Serebryany, Boulder, CO (US); Peter Haeberli, Berthoud, CO (US); David Sweedler, Louisville, CO (US)

(73) Assignee: Sirna Therapeutics, Inc., Boulder, CO (US)

( * ) Notice: Subject to any disclaimer, the term of this patent is extended or adjusted under 35 U.S.C. 154(b) by 238 days.

(21) Appl. No.: 09/944,554

(22) Filed: Aug. 31, 2001

(65) Prior Publication Data

US 2002/0120129 A1 Aug. 29, 2002

Related U.S. Application Data

(60) Provisional application No. 60/230,057, filed on Sep. 1, 2000, and provisional application No. 60/286,571, filed on Apr. 25, 2001.

(51) Int. Cl.$^7$ ......................... C07H 19/16; C07H 19/167
(52) U.S. Cl. ..................... 536/27.1; 536/27.3; 536/124; 536/26.1
(58) Field of Search .............................. 536/27.1, 27.3, 536/124, 26.1

(56) References Cited

U.S. PATENT DOCUMENTS

| | | | |
|---|---|---|---|
| 4,987,071 A | 1/1991 | Cech et al. | |
| 5,631,360 A | 5/1997 | Usman et al. | |
| 5,849,902 A | 12/1998 | Arrow et al. | |
| 5,891,683 A | 4/1999 | Usman et al. | |
| 5,962,675 A | 10/1999 | Beigelman et al. | |
| 5,998,203 A | 12/1999 | Matulic-Adamic et al. | |

FOREIGN PATENT DOCUMENTS

| | | |
|---|---|---|
| JP | 6067492 | 9/1994 |
| JP | 10226697 | 8/1998 |
| WO | Wo 97/26270 | 7/1994 |
| WO | WO 98/28317 | 7/1998 |
| WO | WO 98/58057 | 12/1998 |
| WO | WO 98/58058 | 12/1998 |
| WO | WO 99/16871 | 4/1999 |
| WO | WO 99/55857 | 11/1999 |

OTHER PUBLICATIONS

Inoue et al., Nucleic Acids Symposium Series (1985), 16 (Symp. Nucleic Acids Chem., 13 th), 165–8) abstract sent).*
Grotli et al., "2'–O–(Carbamoylmethyl) oligoribunucleotides," *Tetrahadron* 55:4299–4314 (1999).
Grotli et al., "Protection of the Guanine Residue During Synthesis of 2'–O–alkyl–guanosine Derivatives," *J. Chem. Soc., Perkin Trans.* 1:2779–2788 (1997).
Karpeisky et al., "2'–O–Methylthiomethyl Modifications in Hammerhead Ribozymes," *Nucleosides & Nucleotides* 16:955–958 (1997).
Wada et al., "Regioselective Protection of the 2'Hydroxyl Group of N–Acyl–3', 5'–O–di(t –butyl)silanediylnucleoside Derivatives by Use of t –BuMgCl and 2–(Trimethylsilyl)ethoxymethyl Chloride," *Tetrahedron Letters* 36:1683–1684 (1995).
U.S. patent application Ser. No. 09/406,643, Ludwig et al., filed Sep. 27, 1999.
Agrawal, "Antisense oligonucleotides: towards clinical trials," *Trends Biotech.*, 14, 376–387 (1996).
Beaucage and Iyer, "Advances in the Synthesis of Oligonucleotides by the Phosphoramidite Approach," *Tetrahedron*, 48, 2223–2311 (1992).
Beaudry et al., "In vitro selection of a novel nuclease–resistant RNA phosphodiesterase," *Chemistry and Biology*, 7, 323–334 (2000).
Beigelaman et al., "Synthesis of 2'–modified nucleotides and their incorporation into hammerhead ribozymes," *Nucleic Acids Research* 23(21):4434–4442 (1995).
Bhat, V. et al., "A simple and Convenient Method for the Selective N–Acylations of Cytosine Nucleosides," *Nucleosides & Nuleotide*, 8(2), 179–83 (1989).
Burgin et al., "Chemically Modified Hammerhead Ribozymes with Improved Catalytic Rates," *Biochemistry* 35:14090–14097 (1996) (vol. No. mistakenly listed as 6 ).
Cech, "Ribozymes and Their Medical Implications," *JAMA* 260:3030–3034 (1988).
Chaix et al., "Sold phase synthesis of the 5'half of the initiator 1–RNA from *B. subtilis,*" *Nucleic Acids Research*, 17, 7381–7393 ( 1992).
Christoffersen and Marr, "Riobozymes as Human Therapeutic Agents," *J. Med. Chem.*38: 2023–2037 (1995) (also refered to as Christofferson and Marr).
Cook et al., "Characterization of HIV–1 REV protein: binding stoichiometry and minimal RNA substrate, " *Nucleic Acids Research*, 19, 1577–1583 (1991).
Crooke, "Advances in Understanding the Pharmacological Properties of Antisense Oligonucleotides," *Advances in Pharmacology* 40:1–49 (1997).
Crooke, "Antisense Therapeutics," *Biotechnology and Genetic Engineering Reviews* 15:121–157 (1998).
Delihas et al., "Natural antisense RNA/target RNA interactions: Possible models for antisense oligonucleotide drug design," *Nature Biotechnology* 15:751–753 (1997).

(List continued on next page.)

*Primary Examiner*—Samuel Barts
*Assistant Examiner*—Michael C. Henry
(74) *Attorney, Agent, or Firm*—McDonnell Boehnen Hulbert and Berghoff

(57) ABSTRACT

The present invention provides methods for the chemical synthesis of nucleosides and derivatives thereof, including 2'-amino, 2'-N-phthaloyl, 2'-O-methyl, 2'-O-silyl, 2'-OH nucleosides, C-nucleosides, nucleoside phosphoramidites, C-nucleoside phosphoramidites, and non-nucleoside derivatives.

75 Claims, 15 Drawing Sheets

OTHER PUBLICATIONS

Duval–Valentin, "Specific inhibition of transcription by triple helix–forming oligonucleotides," *Proc. Natl. Acad. Sci USA* 89:504–508 (1992).

Egholm et al., "PNA hybridizes to complementary oligonucleotides obeying the Watson–Crick hydrogen–bonding rules," *Nature* 365:566–568 (1993).

Francklyn and Schmimel, "Aminoacylation of RNA minihelics with alanine, " *Nature*, 337, 478–481 (1989).

Gait et al., "Ch. 2—Oligoribonucleotide synthesis," in *Oligonucleotides and Analogues: A Practical Approach*, edited by Eckstein, IRL Press, Oxford, pp. 25–48 (1991).

Gold, "Posttranscriptional Regulartory Mechanisms in *Escherichia Coli*," *Annu. Rev.Biochemistry*, 57, 199–233 (1988).

Hobbs and Eckstein, "A General Method for the Synthesis of 2'–Azido–2'–deoxy– and 2'–Amino–2'–deoxyribofuranosyl Purines," *J. Org. Chem.* 42:714–719 (1977).

Ikehara and Maruyama, "The Total Synthesis of an Antibiotic 2'–Amino–2'deoxyguanosine," *Chem. Phar. Bull.*, 26, 240–244 (1978).

Ikehara et al., "Synthesis of Phrine Nucleosides having 2'–Azido and 2'–Amino functions by Cleavage of Purine Cyclonucleosides," *Chem. Pharm. Bull.*, 25, 754–760 (1977).

Imazawa and Eckstein, "Facile Synthesis of 2'–Amino–2'–deoxyribofuranosyl Purines," *J. Org. Chem.* 44:2039–2041 (1979).

Johnson and Benkovic, "Analysis of Protein Function by Mutagenesis," *The Enzymes*, vol. 19, 159–211 (1990).

Karaoglu and Thurlow, "A chemical interference study on the interaction of ribosomal protein L1 from *Escherichia coli* with RNA molecules containing its binding site from 23S rRNA, " *Nucleic Acids Research*, 19, 5293–5300. (1991).

McGee et al., "2'–Amino–2'–deoxyuridine via an Interamolecular Cyclization of a Trichloroacetimidate," *J. Org. Chem.*, 61, 781–785 (1996).

Nefkins et al., "A Simple Preparation of Phthaloyl Amino Acids Via a Mild Phthaloylation, " *Recl. Trav. Chim. Pays–Bas.*, 79, 688–698 (1960).

Robins et al., "Nucleic Acid Related Compounds. 71. Efficient General Syntheis of Purine (Amino. Azido, and Triflate)–Sugar Nucleosides," *Nucleosides and Nucleotides* 11;821–834 (1992).

Schmajuk et al., "Antisense Oligonucleotides with Different Backbones, " *The Journal of Biological Chemistry* 274:21783–21789 (1999).

Sproat et al., "An Efficient Method for the Isolation and Purification of Oligoribonucelotides," *Nucleosides & Nucleotides* 14:255–273 (1995).

Stein and Cheng, "Antisense Oligonucleotides as Therapeutic Agents—Is the Bullet Really Magical?" *Science* 261:1004–1288 (1993).

Stein et al., "A Specificity Comparison of Four Antisense Types: Morpholino, 2'–O–Methyl RNA, DNA, and Phosphorothioate DNA, " *Antisense & Nucleic Acid Drug Development* 7:151–157 (1997).

Sullenger et al., "Overexpression of TAR Sequences Renders Cells Resistant to Human Immunodeficiency Virus Replication, "*Cell* 63:601–608 (1990).

Torrence et al., "Targeting RNA for degradation with a (2'–5') oligoadenylate–antisense chimera," *Proc. Natl. Acad. Sci. USA* 90:1300–1304 (1993).

Tsai et al., "In vitro selection of an RNA epitope immunologically cross–reactive with a peptide, " *Proc. Natl. Acad Sci. USA* 89;8864–8868 (1992).

Usman et al., "Automated Chemical Synthesis of Long Oligoribonucelotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Hammerhead ribozyme engineering, " *Current Opinion in Structural Biology* 1:527–533(1996).

Usman and Stinochcomb, "Design, Synthesis and Function of Therapeutic Hammerhead Ribozymes," *Nucleic Acids and Molecular Biology* 10:243–264 (1996).

Usman and Cedergren, "Exploiting the chemical synthesis of RNA, " *TIBS* 17: 334–339 (1992).

Usman et al., "Chemical modification of hammerhead ribozymes: activity and nuclease resistance, " *Nucleic Acids Syposium Series* 31:163–164 (1994).

Vargeese et al., "Efficient activiation fo nucleoside phosphoramidites with 4, 5–dicyanoimidazole during oligonucleotide synthesis, " *Nucleic Acids Research*, 26, 1046–1050 (1998).

Verheyden et al., "Synthesis of Some Phrimidine 2'–Amino–2'–deoxynucleosides," *J. Org. Chem.* 36: 250–254 (1971).

Wincott et al., "Synthesis, deprotection, analysis and purification of RNA and ribozymes, " *Nucleic Acids Research* 23(14):2677–2684 (1995).

* cited by examiner

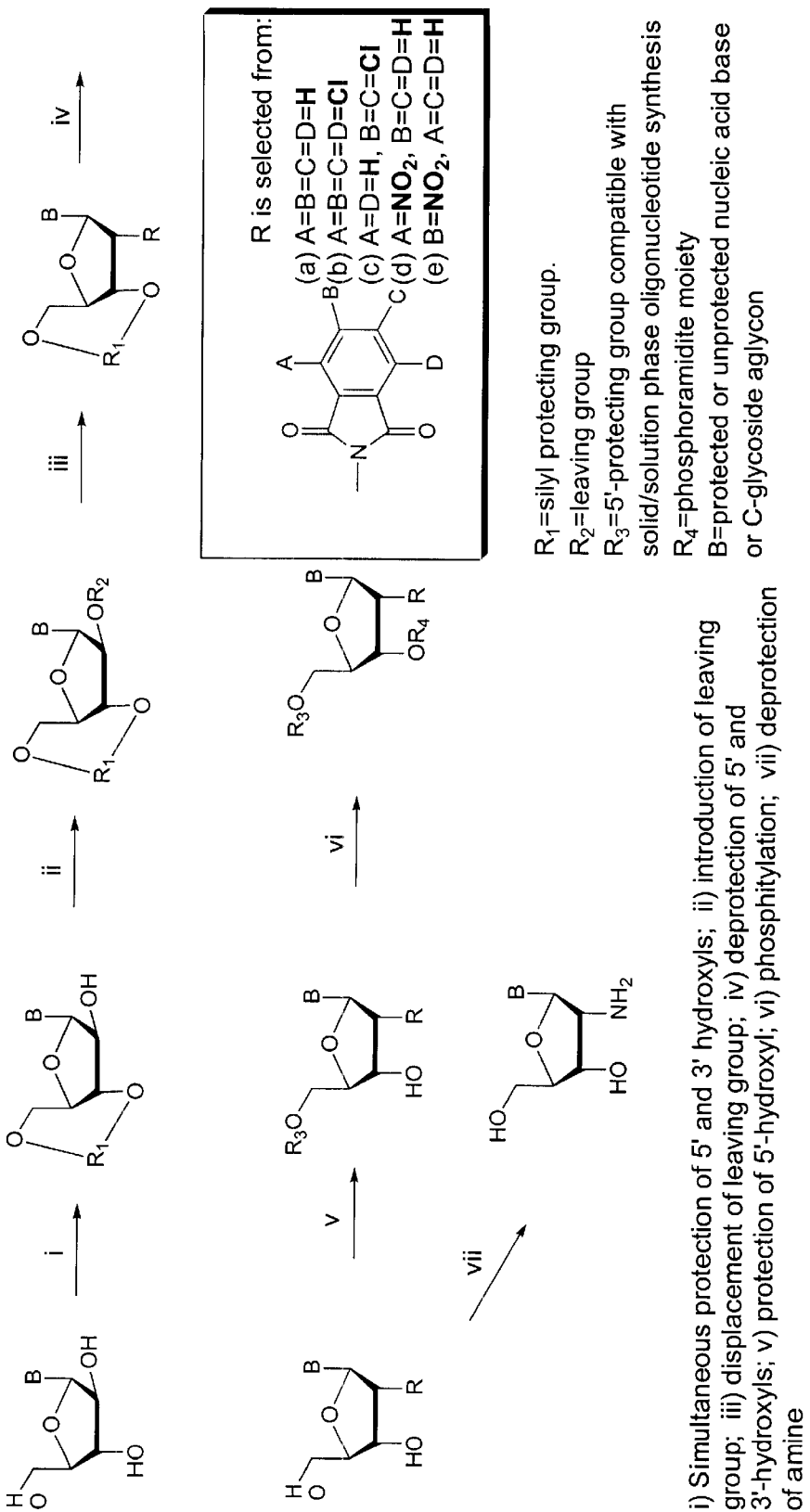
Figure 1: Synthesis of 2'-deoxy-2'-amino nucleosides, C-nucleosides and 2'-deoxy-2'-N-phthaloyl nucleoside and C-nucleoside phosphoramidites

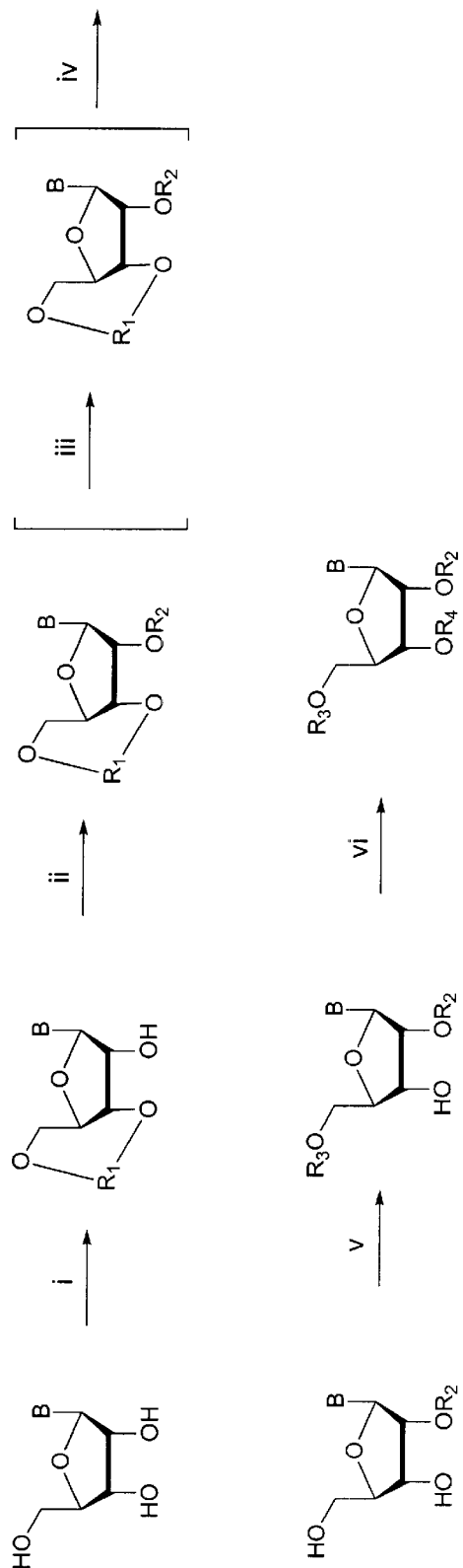

Figure 2: Synthesis of 2'-O-silyl nucleoside phosphoramidites and 2'-O-silyl C-nucleoside phosphoramidites $R_1$ = silyl protecting group
$R_2$ = substituted silyl
$R_3$ = 5'-protecting group compatible with solid/solution phase oligonucleotide synthesis
$R_4$ = phosphoramidite moiety
B = protected or unprotected nucleic acid base or C-glycoside aglycon i) simultaneous protection of 5' and 3' hydroxyls; ii) silylation of 2'-hydroxyl; iii) protection of base (when necessary); iv) deprotection of 5' and 3'-hydroxyls; v) protection of 5'-hydroxyl; vi) phosphitylation

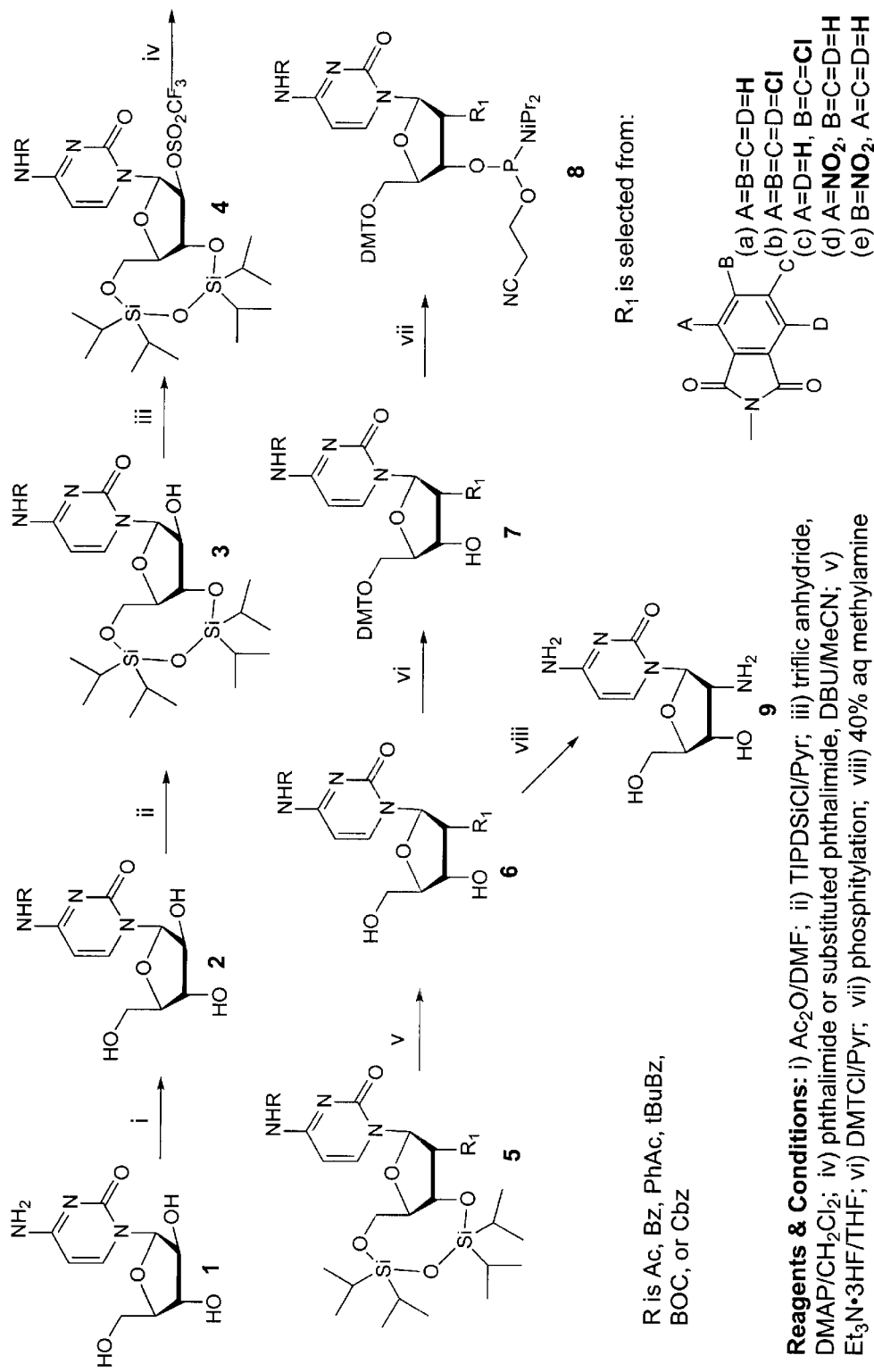

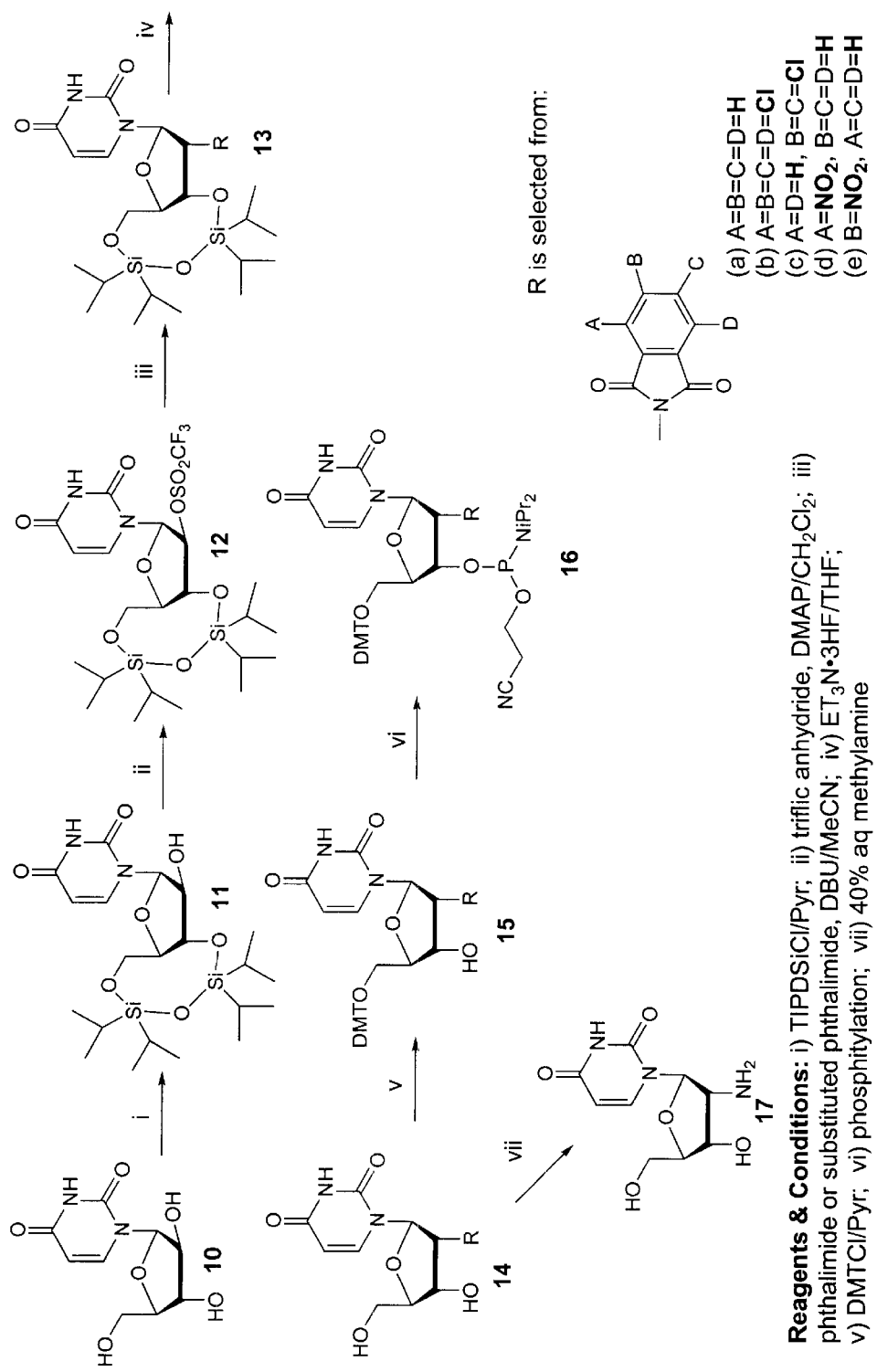
Figure 4: Synthesis of 2'-deoxy-2'-N-phthaloyl Uridine Phosphoramidite

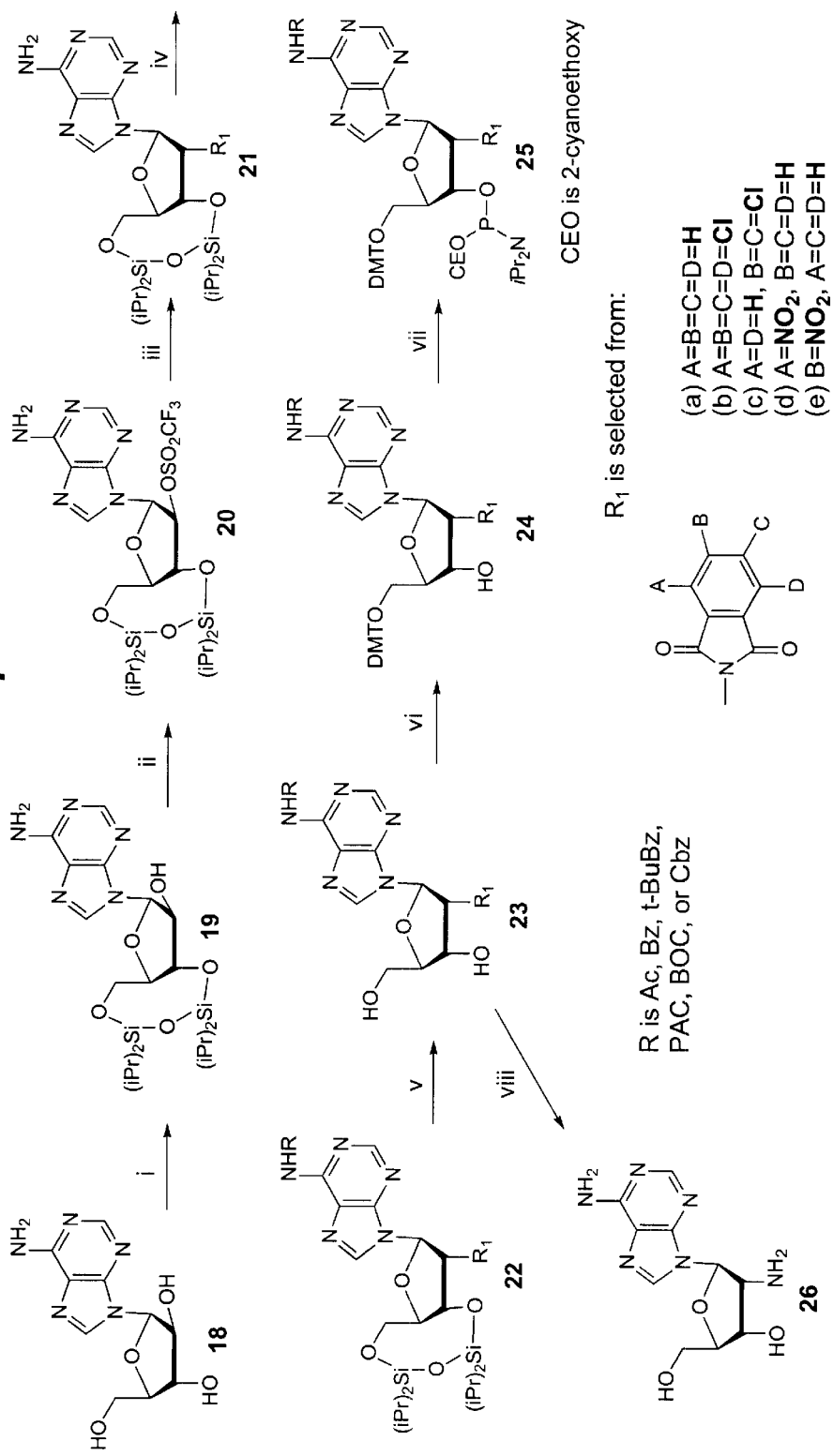
Figure 5: Synthesis of 2'-deoxy-2'-N-phthaloyl Adenosine Phosphoramidite

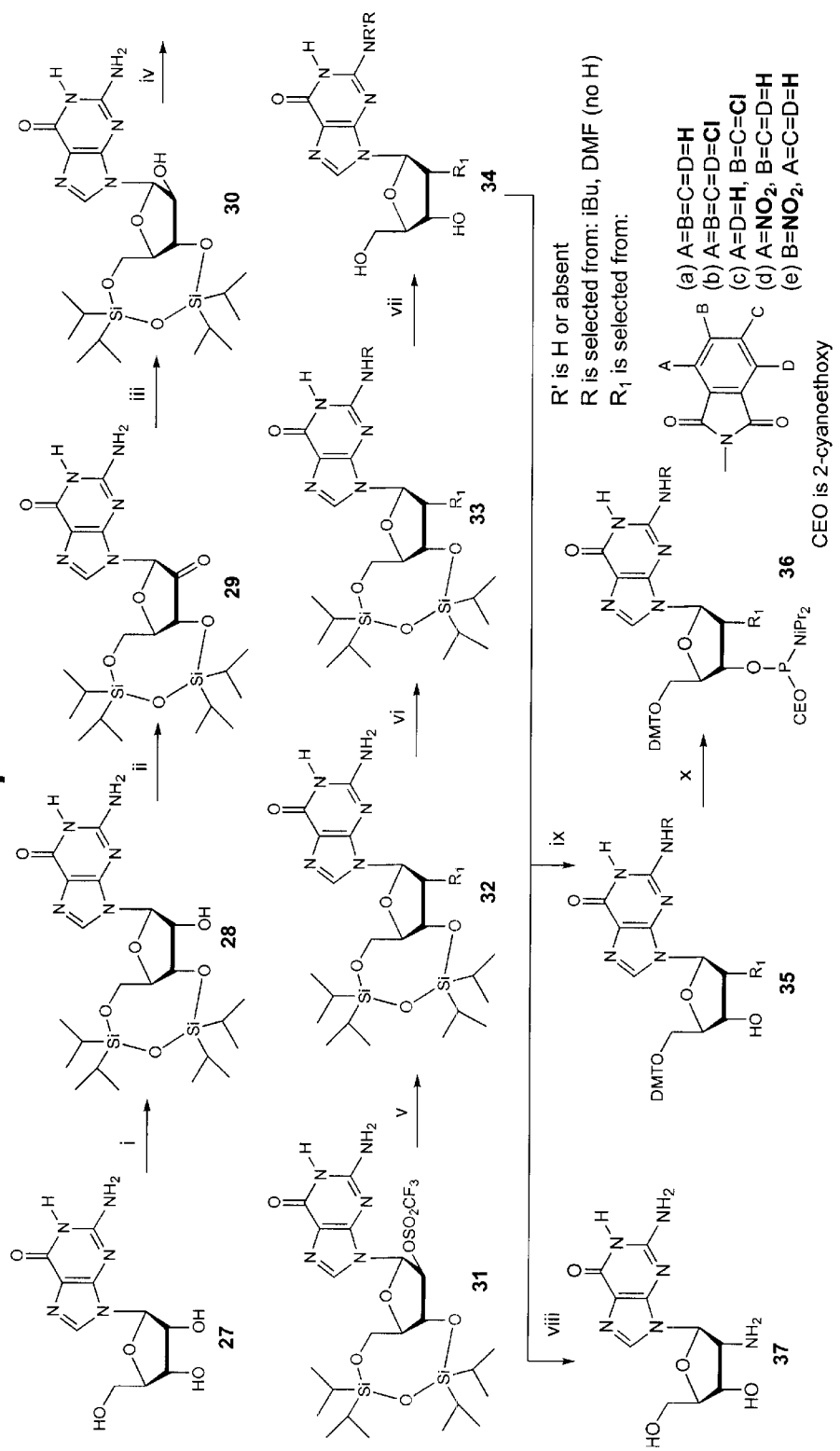
*Figure 6: Synthesis of 2'-deoxy-2'-N-phthaloyl Guanosine Phosphoramidite*
Reagents and conditions: i) TIPDSiCl/Py; ii) CrO$_3$/Py/Ac$_2$O; iii) NaBH$_4$/EtOH; iv) CF$_3$SO$_2$Cl/CH$_2$Cl$_2$, 0°C; v) phthalimide or substituted phthalimide, DBU/MeCN; vi) isobutyryl chloride/Pyr; vii) Et$_3$N·3HF/THF; viii) 40% aq MeNH$_2$; ix) DMT-Cl/Py; x) phosphitylation

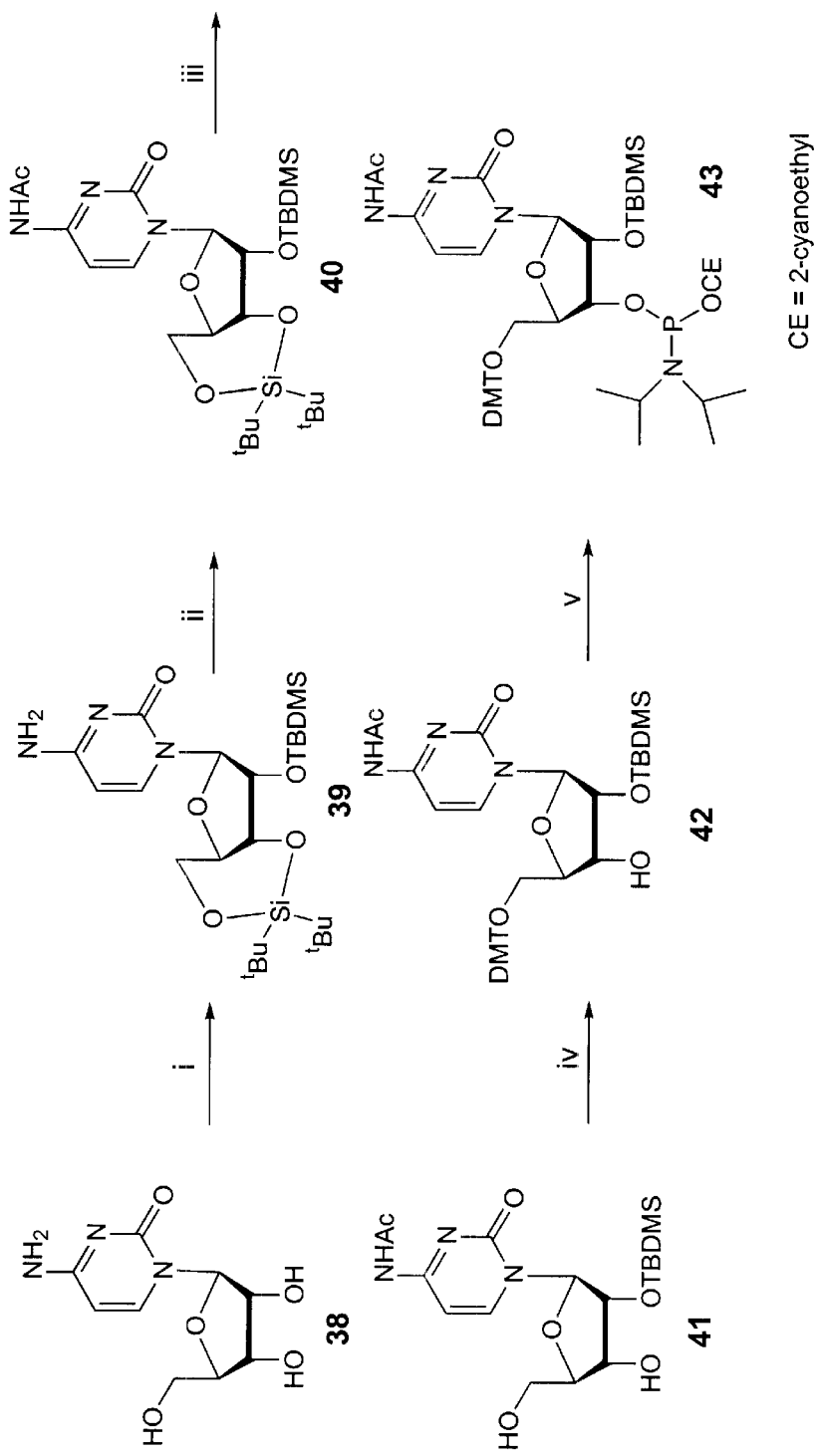
Figure 7: Synthesis of 5'-O-dimethoxytrityl-2'-O-tert-butyldimethylsilyl-N4-acetyl Cytidine 3'-O-(2-cyanoethyl-N,N-diisopropylphosphoramidite)
Reagents & Conditions: i) a. MeSO$_3$H; b. tert-Bu$_2$Si(OSO$_2$CF$_3$)$_2$ / Imidazole; c. tert-BuMe$_2$SiCl / Imidazole ii) acetic anhydride/pyridine iii) HF-Pyr/CH$_2$Cl$_2$; iv) DMT-Cl / Pyr; v) phosphitylation
CE = 2-cyanoethyl

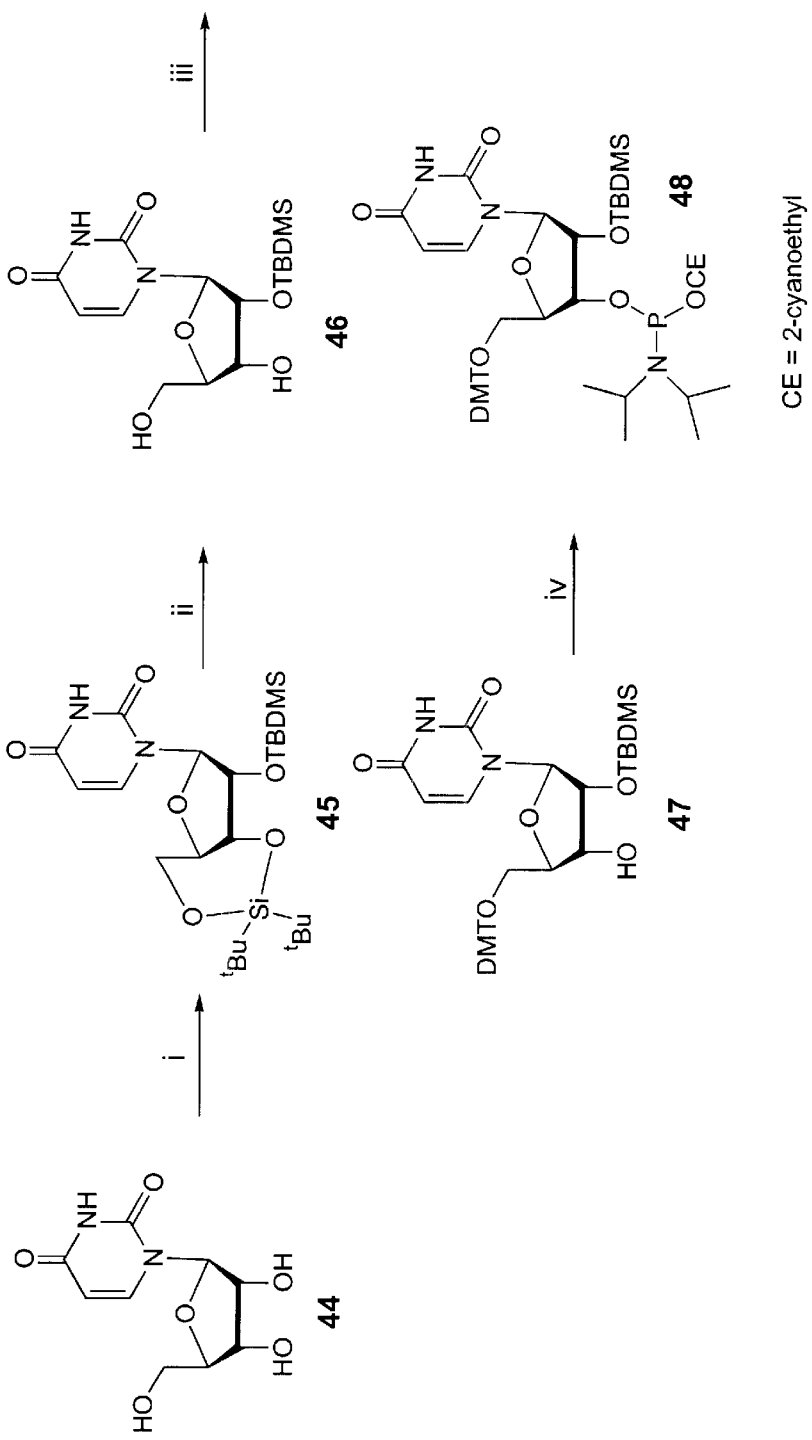
*Figure 8: Synthesis of 5'-O-dimethoxytrityl-2'-O-tert-butyldimethylsilyl Uridine 3'-O-(2-cyanoethyl-N,N-diisopropylphosphoramidite)*
Reagents & Conditions: i) a. tert-Bu$_2$Si(OSO$_2$CF$_3$)$_2$ / Imidazole, b. tert-BuMe$_2$SiCl / Imidazole; ii) HF-Pyr/CH$_2$Cl$_2$; iii) DMT-Cl / Pyr; iv) phosphitylation
CE = 2-cyanoethyl

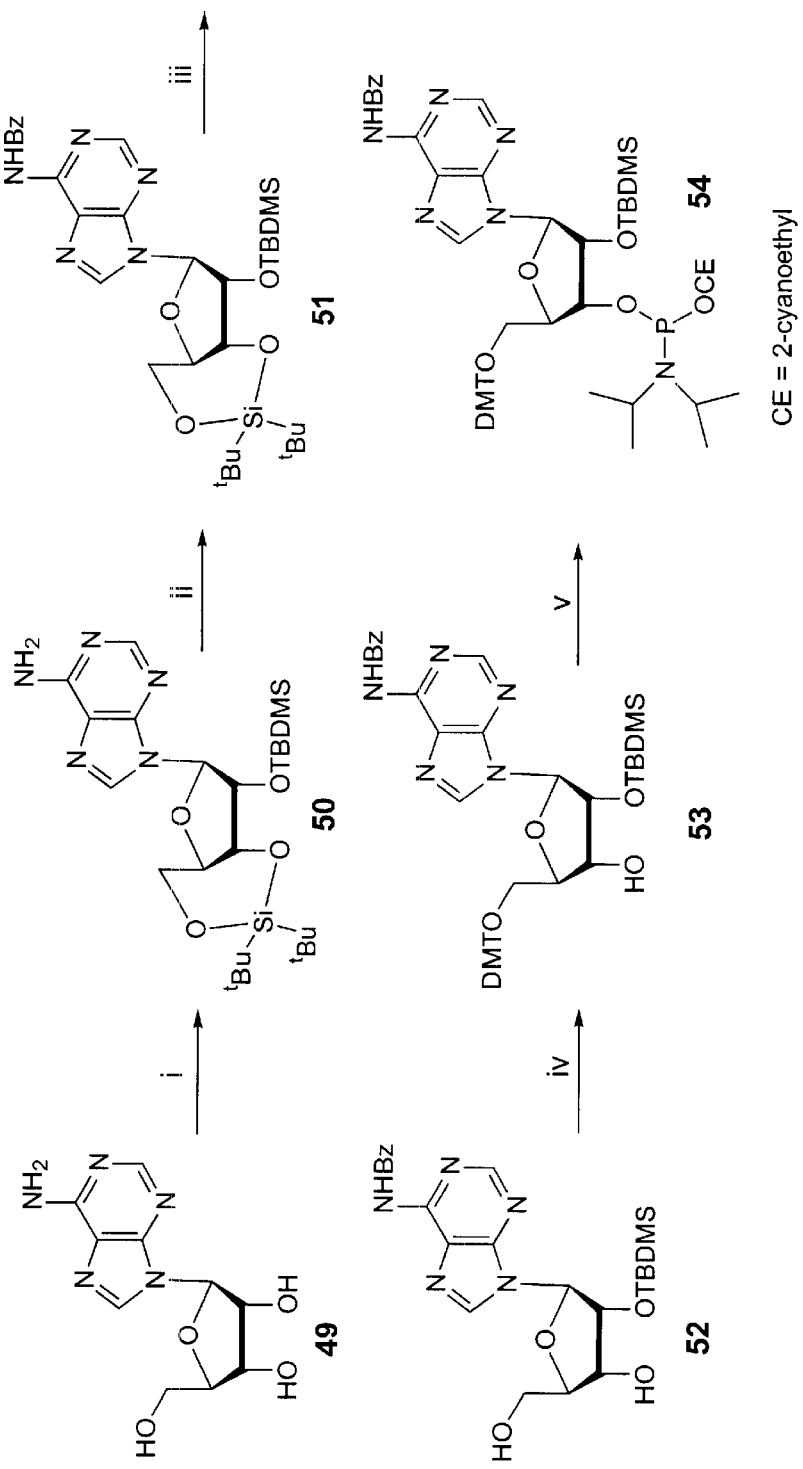
Figure 9: Synthesis of 5'-O-dimethoxytrityl-2'-O-tert-butyldimethylsilyl-N6-benzoyl Adenosine 3'-O-(2-cyanoethyl-N,N-diisopropylphosphoramidite)
Reagents & Conditions: i) a. tert-Bu$_2$Si(OSO$_2$CF$_3$)$_2$ / Imidazole, b. tert-BuMe$_2$SiCl / Imidazole; ii) a. Benzoyl chloride/Pyr b. Morpholine; iii) HF-Pyr/CH$_2$Cl$_2$; iv) DMT-Cl / Pyr; v) phosphitylation
CE = 2-cyanoethyl

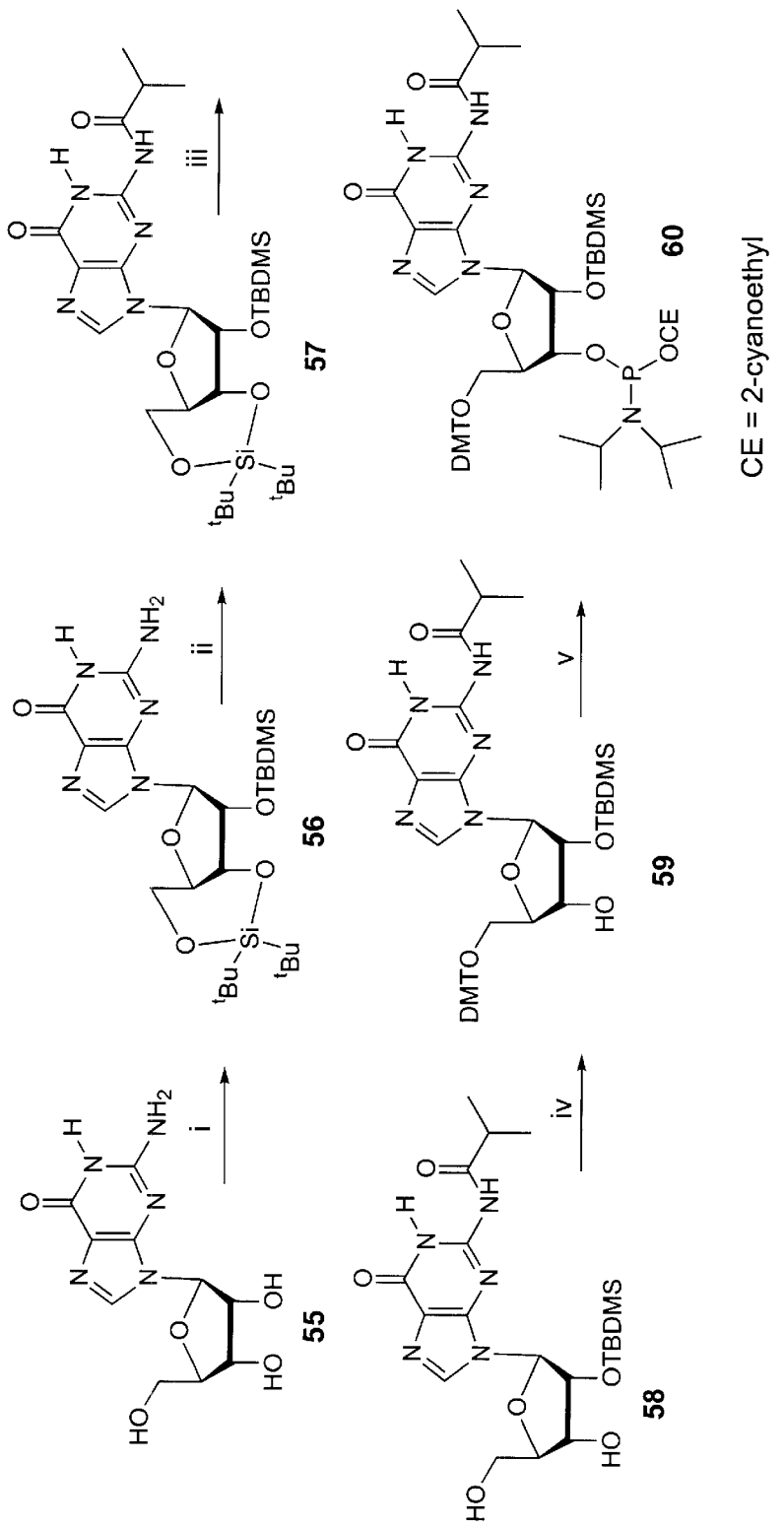
Figure 10: Synthesis of 5'-O-dimethoxytrityl-2'-O-tert-butyldimethylsilyl-N2-isobutyryl Guanosine 3'-O-(2-cyanoethyl-N,N-diisopropylphosphoramidite)
Reagents & Conditions: i) a. tert-Bu$_2$Si(OSO$_2$CF$_3$)$_2$ / Imidazole, b. tert-BuMe$_2$SiCl / Imidazole; ii) a. Isobutyryl chloride/Pyr, b. Methylamine/EtOH; iii) HF-Pyr/CH$_2$Cl$_2$; iv) DMT-Cl / Pyr; v) phosphitylation

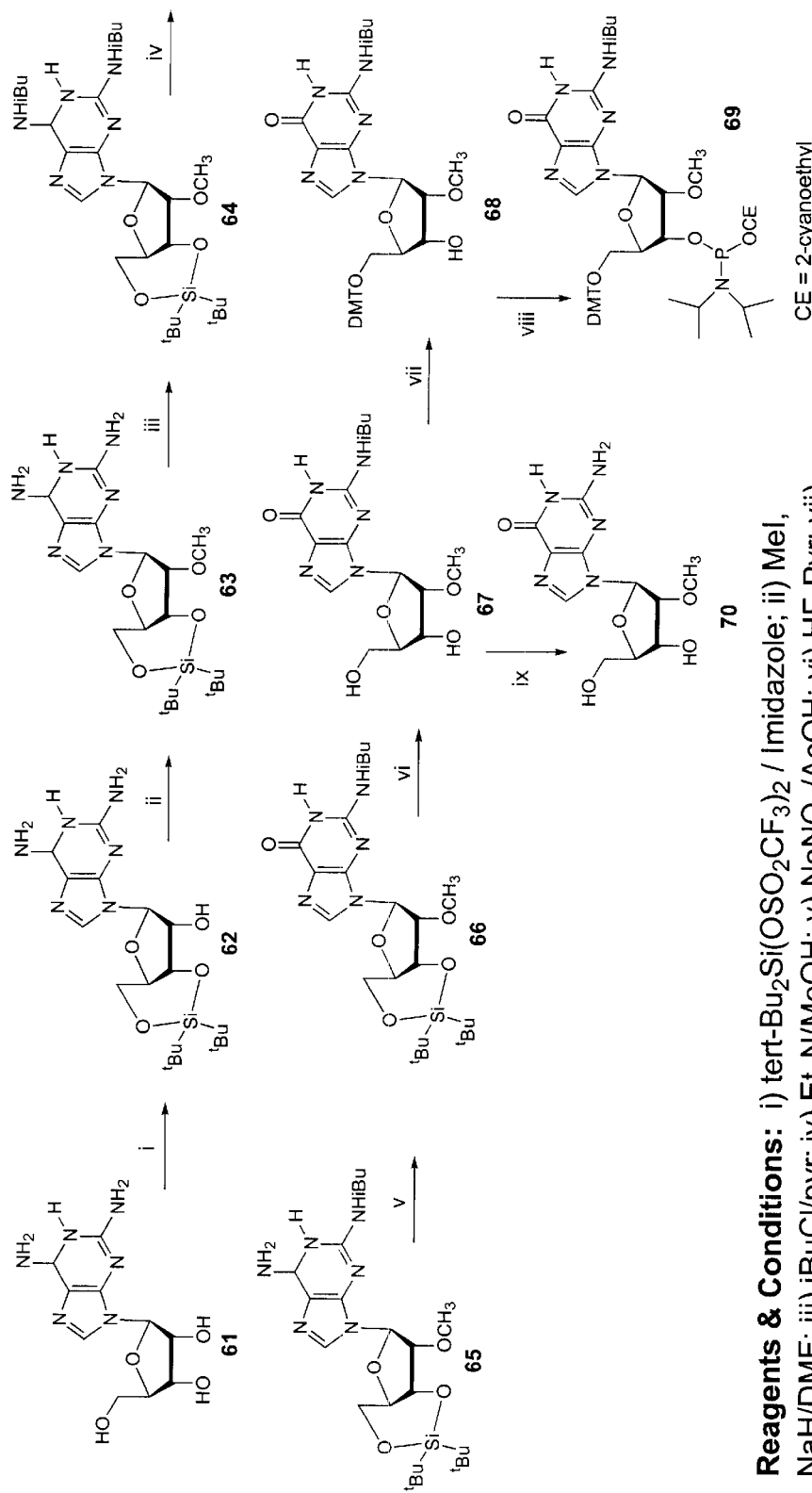
Figure 11: Synthesis of 2'-O-methyl Guanosine and 5'-O-dimethoxytrityl-2'-O-methyl-N2-isobutyryl Guanosine 3'-O-(2-cyanoethyl-N,N-diisopropylphosphoramidite)
Reagents & Conditions: i) tert-Bu$_2$Si(OSO$_2$CF$_3$)$_2$ / Imidazole; ii) MeI, NaH/DMF; iii) iBuCl/pyr; iv) Et$_3$N/MeOH; v) NaNO$_2$/AcOH; vi) HF-Pyr; vii) DMT-Cl / Pyr; viii) phosphitylation; ix) methylamine

Figure 12. Elimination reaction
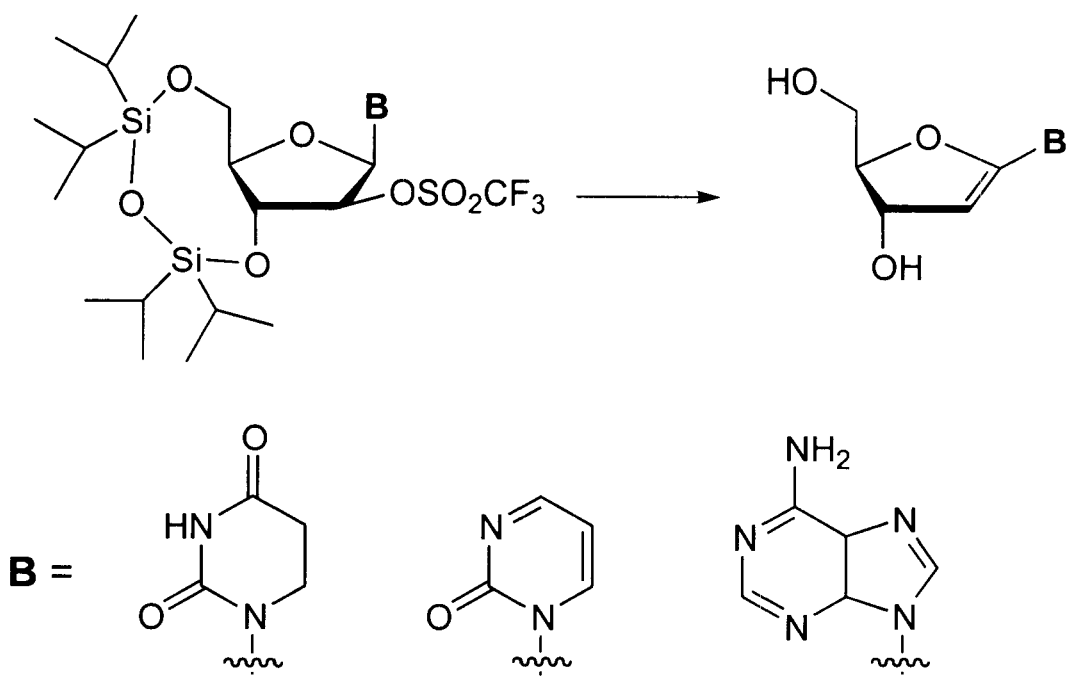

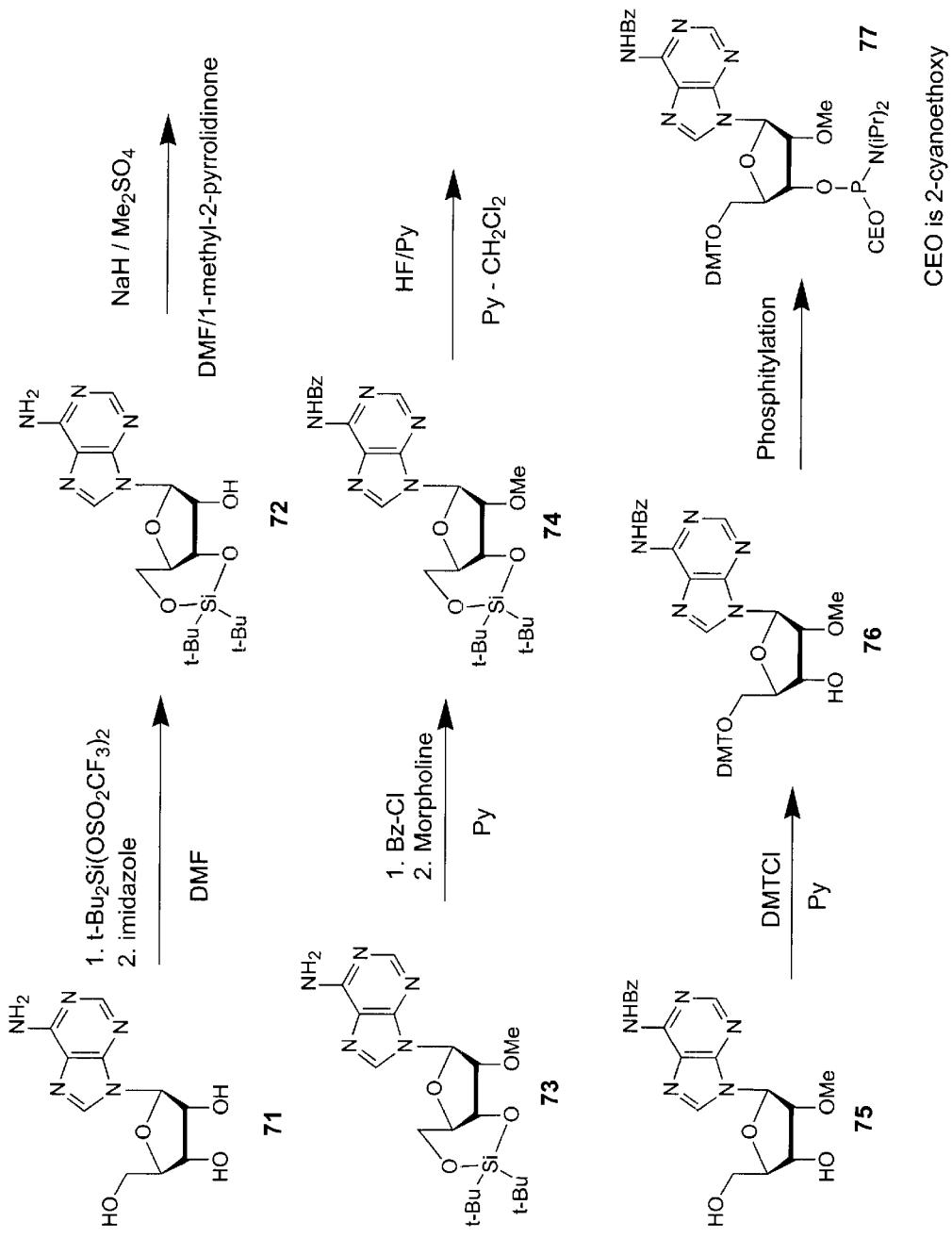
Figure 13: Synthesis of 2'-O-methyl-N6-benzoyl Adenosine Derivatives

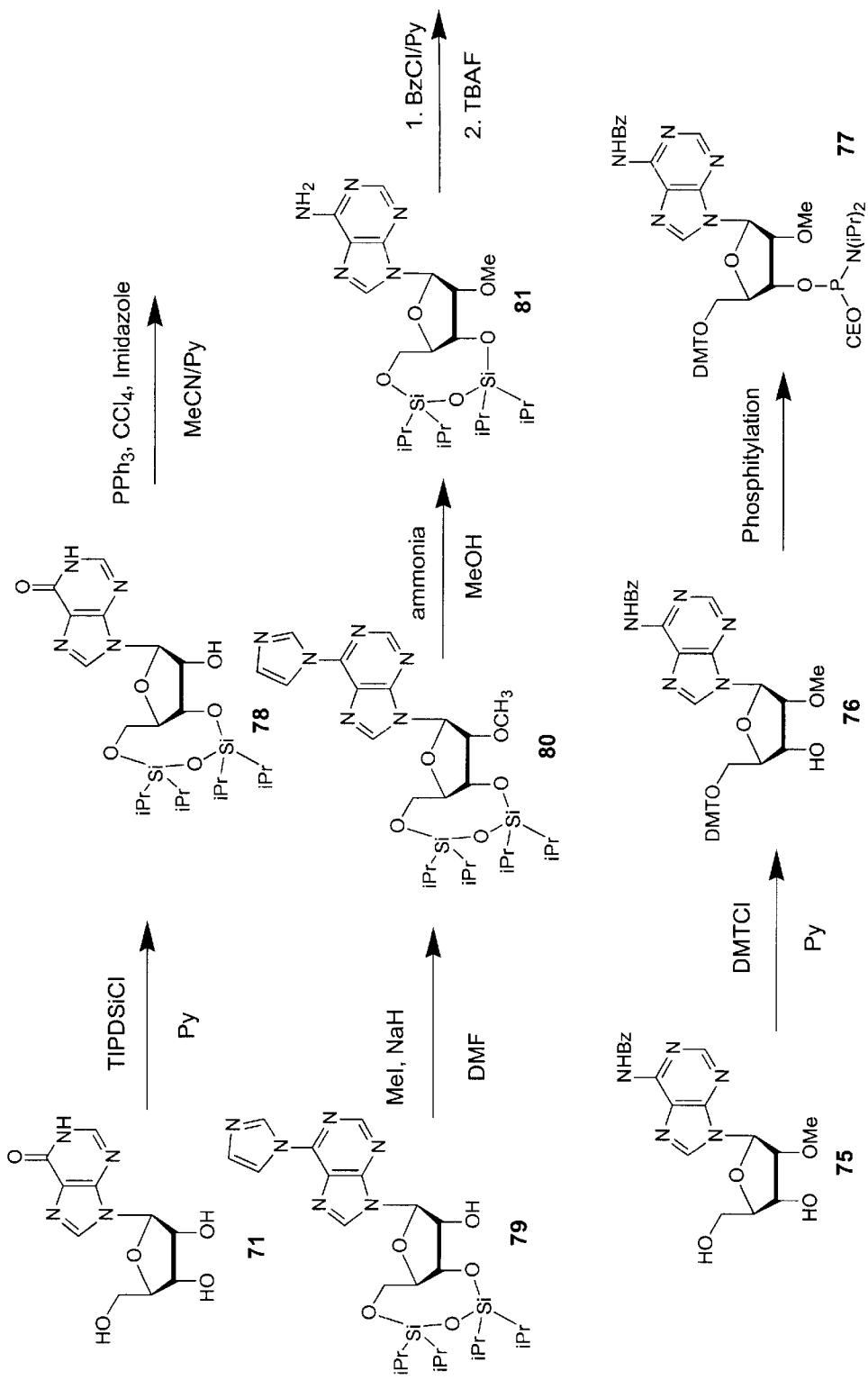
Figure 14: Synthesis of 2'-O-methyl Adenosine Derivatives

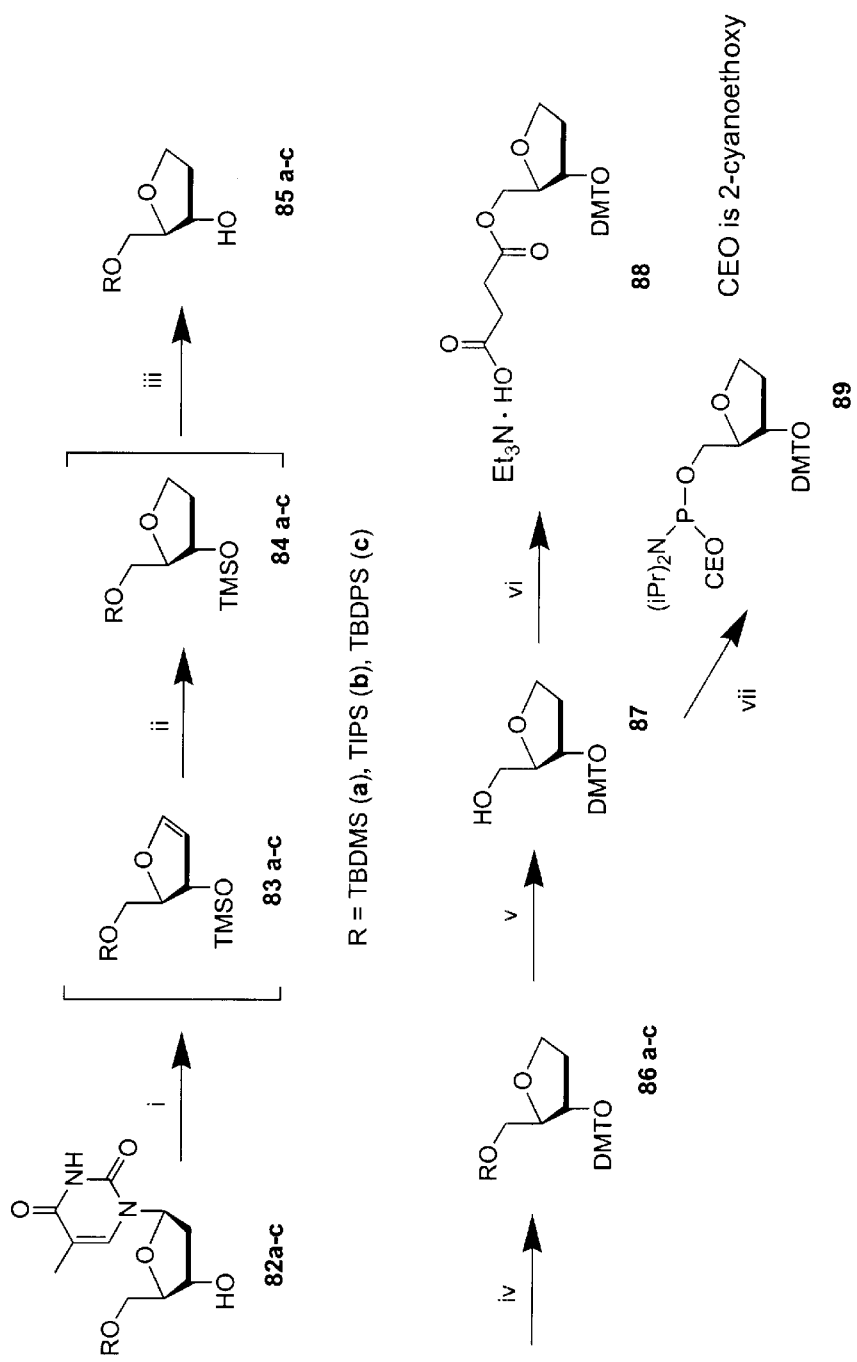
*Figure 15: Synthesis of 1,4-Anhydro-2-deoxy-D-erythro-pentitol derivatives*
Reagents & Conditions: i) HMDS, catalyst, reflux; ii) $H_2$, Pd/C; iii)Py·TFA (0.05 eq), MeOH; iv) DMT-Cl, Py, DMAP; v) NaOH, EtOH-$H_2O$, reflux; vi) succinic anhydride, Py, DMAP, then $Et_3N$vii) phosphitylation

METHODS FOR SYNTHESIZING NUCLEOSIDES, NUCLEOSIDE DERIVATIVES AND NON-NUCLEOSIDE DERIVATIVES

This patent application claims benefit of Beigelman et al., U.S. Ser. No. (60/230,057), filed Sep. 1, 2000, entitled "METHODS FOR SYNTHESIZING NUCLEOSIDES AND NUCLEOSIDE DERIVATIVES" and Beigelman et al., U.S. Ser. No. (60/286,571), filed Apr. 25, 2001, entitled "METHODS FOR SYNTHESIZING NUCLEOSIDES, NUCLEOSIDE DERIVATIVES AND NON-NUCLEOSIDE DERIVATIVES". These applications are hereby incorporated by reference herein in their entirety including the drawings.

TECHNICAL FIELD OF INVENTION

This invention relates to the chemical synthesis of nucleosides, non-nucleosides and derivatives thereof, including nucleoside and non-nucleoside phosphoramidites and succinates.

BACKGROUND OF THE INVENTION

The following is a brief description of the synthesis of nucleosides. This summary is not meant to be complete but is provided only for understanding the invention that follows. This summary is not an admission that the work described below is prior art to the claimed invention.

Structural modifications of oligonucleotides are becoming increasingly important as their possible clinical applications emerge (Usman et al, 1996, Ed., Springer-Verlag, Vol. 10, 243–264; Agrawal, 1996, *Trends Biotech.*, 14, 376–387; Christoffersen and Marr, 1995, *J. Med. Chem.*, 38, 2023–2037). The efficient synthesis of nucleic acids that are chemically modified to increase nuclease resistance while maintaining potency is of importance to the potential development of new therapeutic agents.

Research into the study of structure-function relationships in ribonucleic acids has in the past, been hindered by limited means of producing such biologically relevant molecules (Cech, 1992, *Nucleic Acids Research*, 17, 7381–7393; Francklyn and Schimmel, 1989, *Nature*, 337, 478–481; Cook et al., 1991, *Nucleic Acids Research*, 19, 1577–1583; Gold, 1988, *Annu. Rev. Biochemistry*, 57, 199–233). Although enzymatic methods existed, protocols that allowed one to probe structure function relationships were limited. Only uniform post-synthetic chemical modification (Karaoglu and Thurlow, 1991, *Nucleic Acids Research*, 19, 5293–5300) or site-directed mutagenesis (Johnson and Benkovic, 1990, *The Enzymes*, Vol. 19, Sigman and Boyer, eds., 159–211) were available In the latter case, researchers were limited to using natural bases. Fortunately, adaptation of the phosphoramidite protocol for RNA synthesis has greatly accelerated our understanding of RNA. Site-specific introduction of modified nucleotides at any position in a given RNA has now become routine. Furthermore, one is not confined to a single modification but can include many variations in each molecule.

While it is seemingly out of proportion that one small structural modification can have such an impact, the presence of a single hydroxyl at the 2'-position of the ribofuranose ring has been the major reason that research in the RNA field has lagged so far behind comparable DNA studies. Progress has been made in improving methods for DNA synthesis that have enabled the production of large amounts of antisense deoxyoligonucleotides for structural and therapeutic applications. Only recently have similar gains been achieved for RNA (Wincott et al., 1995, *Nucleic Acids Research*, 23, 2677–2684; Sproat et al., 1995, *Nucleosides and Nucleotides*, 14, 255–273; Vargeese et al., 1998, *Nucleic Acids Research*, 26, 1046–1050).

The chasm between DNA and RNA synthesis is due to the difficulty of identifying orthogonal protecting groups for the 5'- and 2'-hydroxyls. Historically, two standard approaches have been taken by scientists attempting to solve the RNA synthesis problem, The first approach involves developing a method that seeks to adapt to state-of the-art DNA synthesis, while the second approach involves designing a method specifically suited for RNA. Although adaptation of the DNA process provides a more universal procedure in which non-RNA phosphoramidites can easily be incorporated into RNA oligomers, the advantage to the latter approach is that one can develop a process that is optimal for RNA synthesis and as a result, better yields can be realized. However, in both cases similar issues exist, including, for example, the identification of protecting groups that are both compatible with synthesis conditions and capable of being removed at the appropriate juncture. This problem does not refer only to the 2'- and 5'-OH groups, but includes the base and phosphate protecting groups as well. Consequently, the accompanying deprotection steps, in addition to the choice of ancillary agents, are critical. Another shared obstacle is the need for efficient synthesis of the monomer building blocks.

The most common paradigm has been to apply DNA synthesis methods to RNA. Consequently, it is critical to identify a 2'-hydroxyl protecting group that is compatible with DNA protecting groups yet can easily be removed once the oligomer is synthesized. Due to constraints placed by the existing amide protecting groups on the bases and the 5'-O-dimethoxytrityl (DMT) group (or in some cases the 9-(phenyl)xanthen-9-yl (Px) group), the 2'-blocking group must be stable to both acid and base. In addition, the 2'blocking group must also be inert to the oxidizing and capping reagents. Although the most widely used 2'-hydroxyl protecting group is tert-butyldimethylsilyl (TBDMS) ether, many others have been explored. These alternative 2'-protecting groups include acetal groups, such as the tetrahydropyranyl (THP), methoxytetrahydropyranyl (mthp), 1-(2-fluorophenyl)-4-methoxypiperidin-4-yl (Fpmp), 1-(2-chloroethoxy)ethyl, 2-hydroxyisophthalate formaldehyde acetal, and 1-{4-[2-(4-nitrophenyl) ethoxycarbonyloxy]-3-fluorobenzyloxy}ethyl groups. In addition, photolabile groups, such as the o-nitrobenzyl, o-nitrobenzyloxymethyl, and p-nitrobenzyloxymethyl groups have been used. Other groups include the 1,1-dianisyl-2,2,2-trichloroethyl group, the p-nitrophenylethyl sulfonyl group, and the 2'-O-triisopropylsilyl-oxy-methyl group. Additional 2'-protecting groups that have been studied are reviewed in Gait et al., 1991; *Oligonucleotide Synthesis*, In *Oligonucleotides and Analogues, A Practical Approach* (F. Eckstein, ed.), 25–48, and Beaucage and Iyer, 1992, *Tetrahedron*, 48, 2223–2311.

By far the most popular 2'-protecting group is the tert-butyldimethylsilyl group, developed principally by Ogilvie and co-workers (Usman et al., 1987, *J.A.C.S.*, 109, 7845–7854). Recent advances in silyl chemistry in both the synthesis (Wincott et al., 1995, *Nucleic Acids Research*, 23, 2677–2684, Sproat et al., 1995, *Nucleosides and Nucleotides*, 14, 255–273, Vargeese et al., 1998, *Nucleic Acids Research*, 26, 1046–1050) and deprotection (Wincott et al., supra; Sproat et al., supra) arenas have made it's use an even more viable approach to the production of oligoribonucleotides.

The introduction of the tert-butyldimethylsilyl group at the 2'-position of a ribonucleotide is usually effected by the reaction of a 5'-O-dimethoxytrityl-nucleoside with tert-butyldimethylsilyl chloride in the presence of either silver nitrate or imidazole. The resulting mixture of 2'-O-tert-butyldimethylsilyl, 3'-O-tert-butyldimethylsilyl and bis-substituted (3',2'-di-O-tert-butyldimethylsilyl) products must be purified to isolate the desired 2'-O-tert-butyldimethylsilyl derivative, usually by column chromatography. Treatment of the isolated 3'-O-tert-butyldimethylsilyl derivative by equilibration in triethylamine/methanol or pyridine/water can effect migration of the silyl ether, resulting in the capability of isolating additional 2'-O-tert-butyldimethylsilyl product. Multiple re-equilibrations can be utilized to obtain smaller and smaller quantities of the desired 2'-O-tert-butyldimethylsilyl product, however, this process is time-consuming and requires a separate purification step after each equilibration. Therefore, even though formation of the 2'-O-tert-butyldimethylsilyl isomer is sometimes kinetically favored, the resulting isolated yield of the desired 2'-O-tert-butyldimethylsilyl isomer is generally diminished due to formation of the competing 3'-O-tert-butyldimethylsilyl and bis-substituted isomers. Accordingly, there exists a need for a general method for nucleoside phosphoramidite synthesis useful in the selective introduction of silyl protection at the 2'-hydroxyl of a nucleoside.

The utilization of 2'-deoxy-2'-amino nucleotides has resulted in the in vitro selection of novel enzymatic nucleic acid molecules (Beaudry et al., 2000, *Chemistry and Biology*, 7, 323–334). As such, there exists a need for methods suitable for the efficient synthesis of 2'-deoxy-2'-amino containing oligonucleotides. Beigelman et al., 1995, *Nucleic Acids Res.*, 23, 4434–4442, have previously shown that the use of the phthaloyl protecting group for the 2'-amino function of a 2'-deoxy-2'-amino ribonucleotide phosphoramidite during oligonucleotide synthesis is preferable to trifluoroacetyl or Fmoc protecting groups. Beigelman et al., supra, also describe the synthesis of 2'-N-phthaloyluridine phosphoramidite starting from 2'-aminouridine using Nefkins' method (Nefkins et al., 1960, *Recl. Trav. Chim. Pays-Bas.*, 79, 688–698). This procedure requires 2'-deoxy-2'-amino-nucleosides as starting materials.

The first preparation of 2'-aminouridine was described by Verheyden et al., 1971, *J. Org. Chem.*, 36, 250–254. This procedure utilizes lithium azide in the opening of 2,2'-O-anhydrouridine in 50% yield followed by catalytic reduction to the corresponding amine. Several reports elaborating this approach with minor modifications have since been published. An approach utilizing intramolecular cyclization of the 3'-O-trichloroacetimidate of 2,2'-O-anhydrouridine, followed by acid hydrolysis has been published as an alternative to the use of azide ion (McGee et al., 1996, *J. Org. Chem.*, 61, 781–785). Methods for the synthesis of the 2'-aminopurine nucleosides use the same general strategy of introducing a 2'-azido group with subsequent reduction to the amine. Alternatively, 2'-azidopurine nucleosides have been prepared by glycosylation with 2'-azido-2'-deoxy ribose derivatives (Hobbs and Eckstein, 1977, *J. Org., Chem.*, 42, 714–719), transglycosylation with 2'-amino-2'-deoxyuridine, (Imazawa and Eckstein, 1979, *J. Org. Chem.*, 44, 2039–2041), opening of 8,2-cyclopurine nucleosides with azide ion, (Ikehara et al., 1977, *Chem. Pharm. Bull.*, 25, 754–760; Ikehara and Maruyama, 1978, *Chem. Pharm. Bull.*, 26, 240–244), and by displacement of the corresponding 2'-arabino triflates with azide ion (Robins et al., 1992, *Nucleosides and Nucleotides*, 11, 821–834).

Other publications have described the preparation of nucleoside derivatives, including, for example, Karpeisky et al., International PCT Publication No. WO 98/28317, which describes the synthesis of 2'-O-amino nucleosides, Beigelman et al., U.S. Pat. No. 5,962,675, which describe the synthesis of 2'-O-methyl nucleosides, Furusawa, Japanese patent No. 6067492, which describes the synthesis of nucleoside cyclic silicon derivatives, Furusawa, Japanese patent No. 10226697, which describes the synthesis of 2'-O-silyl nucleosides, Usman et al, U.S. Pat. No. 5,631,360, which describes N-phthaloyl protected 2'-amino nucleoside phosphoramidites, Usman et al., U.S. Pat. No. 5,891,683, describe non-nucleoside containing enzymatic nucleic acid molecules, and Matulic-Adamic et al., U.S. Pat. No. 5,998,203, describe enzymatic nucleic acid molecules containing 5' and/or 3'-cap structures.

BRIEF SUMMARY OF THE INVENTION

The invention provides a universal method for the synthesis of 2'-deoxy-2'-amino purine and pyrimidine nucleosides and C-nucleosides that employs fewer synthetic steps, avoids the use of azides, and which concomitantly introduces N-phthaloyl protection of the 2'-amine (see FIG. 1).

In one embodiment, the present invention provides a method for the preparation of 2'-deoxy-2'-amino and 2'-deoxy-2'-N-phthaloyl nucleosides. The method can be scaled up to kilogram or greater quantities. The method comprises the use of phthalimide and/or a substituted phthalimide as a nucleophile in the displacement of a leaving group present at the 2'-position of a 1-β-D-arabinofuranosyl nucleoside, to generate a 2'-deoxy-2'-N-phthaloyl nucleoside. Subsequent cleavage of the phthaloyl protection with a suitable base results in the formation of a 2'-deoxy-2'-amino nucleoside.

The present invention provides a method for synthesizing a 2'-deoxy-2'-N-phthaloyl nucleoside, comprising: (a) introducing a leaving group at the 2'-position of a 1-β-D-arabinofuranosyl nucleoside; an (b) displacing said leaving group from step (a) with a phthalimide or substituted phthalimide nucleophile to yield 2'-deoxy-2'-N-phthaloyl nucleoside.

In another embodiment, the invention provides a method for synthesizing a 2'-deoxy-2'-amino nucleoside, comprising the steps of: (a) introducing a leaving group at the 2'-position of a 1-β-D-arabinofuranosyl nucleoside; (b) displacing said leaving group from step (a) with a phthalimide or substituted phthalimide nucleophile to yield a 2'-deoxy-2'-N-phthaloyl nucleoside; and (c) deprotecting said 2'-deoxy-2'-N-phthaloyl nucleoside to yield said 2'-deoxy-2'-amino nucleoside.

In another embodiment, the present invention provides a method for the preparation of 2'-deoxy-2'-amino and 2'-deoxy-2'-N-phthaloyl C-nucleosides. The method can be scaled up to kilogram or greater quantities. The method comprises the use of phthalimide and/or a substituted phthalimide as a nucleophile in the displacement of a leaving group present at the 2'-position of a 1-β-D-arabinofuranosyl C-nucleoside, to generate a 2'-deoxy-2'-N-phthaloyl C-nucleoside. Subsequent cleavage of the phthaloyl protection with a suitable base results in the formation of a 2'-deoxy-2'-amino C-nucleoside.

In another embodiment, the invention provides a method for synthesizing a 2'-deoxy-2'-N-phthaloyl nucleoside, comprising the step of contacting a 2'-trifluoromethanesulfonyl-1-β-D-arabinofuranosyl nucleoside with a phthalimide or substituted phthalimide nucleophile under conditions suitable for formation of said 2'-deoxy-2'-N-phthaloyl nucleoside.

In another embodiment, the invention provides a method for synthesizing a 2'-deoxy-2'-N-phthaloyl C-nucleoside, comprising the step of contacting a 2'-trifluoromethanesulfonyl-1-β-D-arabinofuranosyl C-nucleoside with a phthalimide or substituted phthalimide nucleophile under conditions suitable for formation of said 2'-deoxy-2'-N-phthaloyl C-nucleoside.

In another embodiment, the invention provides a method for the synthesis of a 2'-deoxy-2'-N-phthaloyl nucleoside, comprising the step of contacting a 2'-methanesulfonyl-1-β-D-arabinofuranosyl nucleoside with a phthalimide or substituted phthalimide nucleophile under conditions suitable for formation of said 2'-deoxy-2'-N-phthaloyl nucleoside.

In another embodiment, the invention provides a method for the synthesis of a 2'-deoxy-2'-N-phthaloyl C-nucleoside, comprising the step of contacting a 2'-methanesulfonyl-1-β-D-arabinofuranosyl C-nucleoside with a phthalimide or substituted phthalimide nucleophile under conditions suitable for formation of said 2'-deoxy-2'-N-phthaloyl C-nucleoside.

In another aspect, the invention also provides a method for the synthesis of nucleic acid base protected 2'-O-silyl nucleoside phosphoramidites and 2'-O-silyl C-nucleosides (FIG. 2) that avoids formation of the competing 3'-O-silyl nucleoside isomer, thereby improving overall synthetic yield while avoiding the need for separation of 2'-O-silyl nucleoside and 3'-O-silyl nucleoside isomers. The method described herein avoids the practice of re-equilibration of the 3'-O-silyl nucleoside isomer to generate additional 2'-O-silyl nucleoside. Additionally, the present method avoids the need for transient protection of the furanosyl hydroxyls as a separate step in the protection of the nucleic acid base.

The present invention also provides a method for the preparation of 2'-O-silyl-nucleosides and 2'-O-silylnucleoside phosphoramidites. The method can be scaled up to kilogram or greater quantities. The method comprises the steps of (1) introducing a 5',3'-cyclic silyl protecting group to a nucleoside; (2) introducing a 2'-O-silyl protecting group to the product of step (1); (3) introducing nucleic acid base protection where necessary to the product of step (2); (4) selectively desilylating the product of step (3); (5) introducing a 5'-hydroxyl protecting group to the product of step (4), and (6) introducing a phosphoramidite moiety at the 3'-position of the product of step (5) with a phosphitylating reagent to yield a 2'-O-silyl-nucleoside phosphoramidite.

In another embodiment, the invention provides a method for the synthesis of 2'-O-silyl-nucleosides and 2'-O-silyl-nucleoside phosphoramidites comprising the steps of (1) introducing nucleic acid base protection where necessary to a nucleoside; (2) introducing a 5',3'-cyclic silyl protecting group to the product of step (1); (3) introducing a 2'-O-silyl protecting group to the product of step (2); (4) selectively desilylating the product of step (3); (5) introducing a 5'-hydroxyl protecting group to the product of step (4); and (6) introducing a phosphoramidite moiety at the 3'-position of the product of step (5) with a phosphitylating reagent to yield a 2'-O-silyl-nucleoside phosphoramidite.

In another embodiment, the method for synthesis of 2'-O-silyl-nucleosides and 2'-O-silyl-nucleoside phosphoramidites is used for the synthesis of 2'-O-silyl-D-ribofuranosyl nucleosides, 2'-O-silyl-D-ribofuranosyl nucleoside phosphoramidites, 2'-O-silyl-L-ribofuranosyl nucleosides, 2'-O-silyl-L-ribofuranosyl nucleoside phosphoramidites, 2'-O-silyl-D-arabinofuranosyl nucleosides, 2'-O-silyl-D-arabinofuranosyl nucleoside phosphoramidites and both 2'-O-silyl-L-arabinofuranose nucleosides and 2'-O-silyl-L-arabinofuranose nucleoside phosphoramidites.

The present invention also provides a method for the preparation of 2'-O-silyl-C-nucleosides and 2'-O-silyl-C-nucleoside phosphoramidites. The method can be scaled up to kilogram or greater quantities. The method includes the steps of (1) introducing a 5',3'-cyclic silyl protecting group to a C-nucleoside; (2) introducing a 2'-O-silyl protecting group to the product from step (1); (3) introducing nucleic acid base protection where necessary to the product of step (2); (4) selectively desilylating the product of step (3); (5) introducing a 5'-hydroxyl protecting group to the product of step (4); and (6) introducing a phosphoramidite moiety at the 3'-position of the product of step (5) with a phosphitylating reagent.

In another embodiment, the invention provides a method for synthesizing 2'-O-silyl-C-nucleosides and 2'-O-silyl-C-nucleoside phosphoramidites comprising the steps of (1) introducing nucleic acid base protection where necessary to a C-nucleoside; (2) introducing a 5',3'-cyclic silyl protecting group to the product of step (1); (3) introducing a 2'-O-silyl protecting group to the product from step (2); (4) selectively desilylating the product of step (3); (5) introducing a 5'-hydroxyl protecting group to the product of step (4); and (6) introducing a phosphoramidite moiety at the 3'-position of the product of step (5) with a phosphitylating reagent.

In another embodiment, the method for synthesis of 2'-O-silyl-C-nucleosides and 2'-O-silyl-C-nucleoside phosphoramidites is used for the synthesis of 2'-O-silyl-D-ribofuranosyl C-nucleosides and 2'-O-silyl-D-ribofuranosyl C-nucleoside phosphoramidites, 2'-O-silyl-L-ribofuranosyl C-nucleosides and 2'-O-silyl-L-ribofuranosyl C-nucleoside phosphoramidites, 2'-O-silyl-D-arabinofuranosyl C-nucleosides and 2'-O-silyl-D-arabinofuranosyl C-nucleoside phosphoramidites and both 2'-O-silyl-L-arabinofuranose C-nucleosides and 2'-O-silyl-L-arabinofuranose C-nucleoside phosphoramidites.

In yet another aspect of the invention, a method for the preparation of 2'-O-methyl guanosine nucleosides and 2'-O-methyl guanosine nucleoside phosphoramidites is provided. The 2'-O-methyl guanosine nucleosides and 2'-O-methyl guanosine nucleoside phosphoramidites are synthesized from a 2,6-diaminopurine nucleoside by selective methylation of the 2,6-diaminopurine nucleoside followed by selective deamination of the 2,6-diaminopurine nucleoside to afford a 2'-O-methyl guanosine nucleoside.

The present invention provides a practical method for the preparation of 2'-O-methyl guanosine nucleosides and 2'-O-methyl guanosine nucleoside phosphoramidites. The method can be scaled up to kilogram or greater quantities. The method includes the steps of (1) introducing a 5',3'-cyclic silyl protecting group to a 2,6-diamino-9-(β-ribofuranosyl) purine with a disilylalkyl bis(trifluoromethanesulfonate) to form a 2,6-diamino-9-[5',3'-O-(di-alkylsilanediyl)-2'-O-methyl-β-ribofuranosyl]purine; (2) methylation of the product of step (1) under conditions suitable for the isolation of a 2,6-diamino-9-[5',3'-O-(di-alkylsilanediyl)-β-ribofuranosyl]purine; (3) introducing acyl protection at the N2 and N6 positions of the product from step (2) under conditions suitable for the isolation of $N^2$–$N^6$-2,6-diamino-diacyl-9-[5',3'-O-(di-alkylsilanediyl)-2'-O-methyl-β-ribofuranosyl]purine; (4) selectively deacylating position $N^6$ of the product of step (3), under conditions suitable for the isolation of 2,6-diamino-$N^2$-acyl-9-[5',3'-O-(di-alkylsilanediyl)-2'-O-methyl-β-ribofuranosyl]purine; (5) chemically deaminating the N6-amine and desilylating the product of step (4), under conditions suitable for the isolation of $N^2$-acyl-2'-O-methyl guanosine; (6) introducing a 5'-hydroxyl protecting group to the product of step (5), under conditions suitable for obtaining a $N^2$-acyl-5'-O-dimethoxytrityl-2'-O-methyl guanosine; and (7) introducing a phosphoramidite moiety at the 3'-position of the product of step (6) with a phosphitylating reagent under conditions suitable for isolating a $N^2$-acyl-5'-O-dimethoxytrityl-2'-O-methyl guanosine 3'-O-(2-cyanoethyl-N,N-diisopropylphosphoramidite).

In another embodiment, the present invention provides a method for the chemical synthesis of a 2'-O-methyl guanosine nucleoside comprising the steps of: (1) introducing a 5',3'-cyclic silyl protecting group to a 2,6-diamino-9-(β-ribofuranosyl)purine with a disilylalkyl bis(trifluoromethanesulfonate) to form a 2,6-diamino-9-[5',3'-O-(di-alkylsilanediyl)-β-ribofuranosyl]purine; (2) methylation of the product of step (1) under conditions suitable for the isolation of a 2,6-diamino-9-[5',3'-O-(di-alkylsilanediyl)-2'-O-methyl-β-ribofuranosyl]purine; (3) acylation of the N2 and N6 positions of the product from step (2) under conditions suitable for the isolation of a 2,6-diamino-N2–N6-diacyl-9-[5',3'-O-(di-alkylsilanediyl)-2'-O-methyl-β-ribofuranosyl]purine; (4) selectively deacylating position N6 of the product of step (3), under conditions suitable for the isolation of a 2,6-diamino-N2-acyl-9-[5',3'-O-(di-alkylsilanediyl)-2'-O-methyl-β-ribofuranosyl]purine; (5) deaminating the N6-amine and desilylating the product of step (4) under conditions suitable for the isolation of a N2-acyl-2'-O-methyl guanosine; and (6) deprotection of the N2-amine from the product of step (e) under conditions suitable for the isolation of said 2'-O-methyl guanosine nucleoside.

In yet another aspect of the invention, a method for the preparation of 2'-O-alkyl adenosine nucleosides and 2'-O-alkyl adenosine nucleoside phosphoramidites is provided. The 2'-O-alkyl adenosine nucleosides and 2'-O-alkyl adenosine nucleoside phosphoramidites are synthesized from a adenosine by selective alkylation of the 2'-hydroxyl of 5',3'-silanediyl protected adenosine nucleoside followed by selective deprotection of the 5',3'-silanediyl to afford a 2'-O-alkyl adenosine nucleoside. Protection of the N6 amine of adenosine if desired can take place after alkylation and before deprotection of the 5',3'-silanediyl to afford a N6-acyl-2'-O-alkyl adenosine. Acid labile protecting groups and phosphorous containing groups compatible with oligonucleotide synthesis can be introduced as is known in the art.

In one embodiment, the 2'-O-alkyl adenosine nucleosides and 2'-O-alkyl adenosine nucleoside phosphoramidites are synthesized from a inosine by introducing an imidazole or triazole moiety at the O6 position of a 5',3'-silanediyl protected inosine nucleoside as, followed by selective alkylation of the 2'-hydroxyl of the 5',3'-silanediyl protected adenosine N6-imidazole nucleoside followed by N6 amination and deprotection of the 5',3'-silanediyl and to afford a 2'-O-alkyl adenosine nucleoside. Alternately, the 5',3'-silanediyl protected 2'-O-alkyl adenosine N6-imidazole nucleoside is desilyated to a 2'-O-alkyl adenosine N6-imidazole nucleoside which is aminated with ammonia to provide 2'-O-alkyl adenosine. Acid labile protecting groups and phosphorous containing groups compatible with oligonucleotide synthesis can be introduced as is known in the art.

The present invention provides a practical method for the preparation of 2'-O-alkyl adenosine nucleosides and 2'-O-alkyl adenosine nucleoside phosphoramidites. The method can be scaled up to kilogram or greater quantities. The method includes the steps of (1) introducing a 5',3'-cyclic silyl protecting group to adenosine with a disilylalkyl bis(trifluoromethanesulfonate) to form a 5',3'-O-(di-alkylsilanediyl)-adenosine; (2) alkylation of the product of step (1) under conditions suitable for the isolation of a 5',3'-O-(di-alkylsilanediyl)-2'-O-alkyl adenosine; (3) introducing acyl protection at the N6 position of the product from step (2) under conditions suitable for the isolation of $N^6$-acyl-5',3'-O-(di-alkylsilanediyl)-2'-O-alkyl adenosine; (4) desilylating the product of step (3), under conditions suitable for the isolation of $N^2$-acyl-2'-O-alkyl adenosine; (5) introducing a 5'-hydroxyl protecting group to the product of step (4), under conditions suitable for obtaining a $N^6$-acyl-5'-O-dimethoxytrityl-2'-O-alkyl adenosine; and (6) introducing a phosphoramidite moiety at the 3'-position of the product of step (5) with a phosphitylating reagent under conditions suitable for isolating a $N^6$-acyl-5'-O-dimethoxytrityl-2'-O-alkyl adenosine 3'-O-(2-cyanoethyl-N,N-diisopropylphosphoramidite).

In another embodiment, the present invention provides a method for the chemical synthesis of a 2'-O-alkyl adenosine nucleoside comprising the steps of: (1) introducing a 5',3'-cyclic silyl protecting group to adenosine with a disilylalkyl bis(trifluoromethanesulfonate) to form a 5',3'-O-(di-alkylsilanediyl) adenosine; (2) alkylation of the product of step (1) under conditions suitable for the isolation of a 5',3'-O-(di-alkylsilanediyl)-2'-O-alkyl adenosine; (3) desilylating the product of step (2), under conditions suitable for the isolation of $N^6$-acyl-2'-O-alkyl adenosine.

The present invention provides a practical method for the preparation of 2'-O-alkyl adenosine nucleosides and 2'-O-alkyl adenosine nucleoside phosphoramidites. The method can be scaled up to kilogram or greater quantities. The method includes the steps of (1) introducing a 5',3'-cyclic silyl protecting group to inosine to form a 5',3'-protected-inosine; (2) introducing a $N^6$ imidazole moiety to the product of step (1) under conditions suitable for the isolation of a 5',3-protected-$N^6$-imidazole adenosine; (3) alkylation of the product of step (2) under conditions suitable for the isolation of a 5',3'-protected-2'-O-alkyl-$N^6$-imidazole adenosine; (4) introducing acyl protection at the N6 position of the product from step (3) under conditions suitable for the isolation of $N^6$-acyl-5',3'-protected-2'-O-alkyl adenosine; (5) desilylating the product of step (4), under conditions suitable for the isolation of $N^6$-acyl-2'-O-alkyl adenosine; (6) introducing a 5'-hydroxyl protecting group to the product of step (5), under conditions suitable for obtaining a $N^6$-acyl-5'-O-dimethoxytrityl-2'-O-alkyl adenosine; and (7) introducing a phosphoramidite moiety at the 3'-position of the product of step (6) with a phosphitylating reagent under conditions suitable for isolating a $N^6$-acyl-5'-O-dimethoxytrityl-2'-O-alkyl adenosine 3'-O-(2-cyanoethyl-N,N-diisopropylphosphoramidite).

In another embodiment, the present invention provides a method for the chemical synthesis of a 2'-O-alkyl adenosine nucleoside comprising the steps of: (1) introducing a 5',3'-cyclic silyl protecting group to inosine to form a 5',3'-protected inosine; (2) introducing a $N^6$ imidazole moiety to the product of step (1) under conditions suitable for the isolation of a $N^6$-imidazole-5',3'-protected adenosine; (3) alkylation of the product of step (2) under conditions suitable for the isolation of a $N^6$-imidazole-5',3'-protected-2'-O-alkyl adenosine; (4) aminating the N6 position of the product from step (3) under conditions suitable for the isolation of a $N^6$-acyl-5',3'-protected-2'-O-alkyl adenosine or 5',3'-protected-2'-O-alkyl adenosine; (5) desilyl product of step (4), under conditions suitable for the isolation of $N^6$-acyl-2'-O-alkyl adenosine or 2'-O-alkyl adenosine.

In another embodiment, amination of the $N^6$-imidazole-5',3'-protected-2'-O-alkyl adenosine utilizes an acylamide, for example benzamide, to introduce exocyclic amine protection, either before or after desilylation.

The present invention also provides a practical method for the synthesis of 1,4-anhydro-2-deoxy-D-erythro-pentitol derivatives, including 1,4-anhydro-2-deoxy-D-erythro-pentitol succinates and phosphoramidites. The method includes the steps of (1) depyrimidination of a 5'-O-protected thymidine derivative under conditions suitable for the isolation of a 5-O-protected-1,4-anhydro-2-deoxy-D-erythro-pentitol, (2) introduction of an acid-labile protecting group at the C3 hydroxyl of the 5-O-protected-1,4-anhydro-2-deoxy-D-erythro-pentitol under conditions suitable for the isolation of a 5-O-protected-3-O-protected-1,4-anhydro-2-deoxy-D-erythro-pentitol, (3) selective 5-O-deprotection of the product of step (2) under conditions suitable for the isolation of a 3-O-protected-1,4-anhydro-2-deoxy-D-erythro-pentitol, and (4) introducing a chemical moiety comprising a succinate moiety or a phosphoramidite moiety at position 5 of the product of step (3) under conditions suitable for the isolation of a 5-O-succinyl-3-O-protected-1,4-anhydro-2-deoxy-D-erythro-pentitol or a 3-O-protected-1,4-anhydro-2-deoxy-D-erythro-pentitol-5-O-phosphoramidite.

BRIEF DESCRIPTION OF THE FIGURES

FIG. 1 is a diagrammatic representation of a generalized reaction scheme describing the synthesis of 2'-deoxy-2'-amino nucleosides, 2'-deoxy-2'-amino C-nucleosides, 2'-deoxy-2'-N-phthaloyl nucleosides, 2'-deoxy-2'-N-phthaloyl C-nucleosides, nucleoside phosphoramidites and C-nucleoside phosphoramidites by the method of this invention.

FIG. 2 is a diagrammatic representation of a generalized reaction scheme describing the synthesis of 2'-O-silyl nucleoside phosphoramidites and 2'-O-silyl C-nucleoside phosphoramidites by the method of this invention.

FIG. 3 is a diagrammatic representation of a scheme involved in the synthesis of a 2'-deoxy-2'-N-phthaloyl cytidine 3'-O-(2-cyanoethyl-N,N-diisopropylphosphoramidite) (8) and 2'-deoxy-2'-amino cytidine (9) by the method of this invention.

FIG. 4 is a diagrammatic representation of a scheme involved in the synthesis of a 2'-deoxy-2'-N-phthaloyl uridine 3'-O-(2-cyanoethyl-N,N-diisopropylphosphoramidite) (16) and 2'-deoxy-2'-amino uridine (17) by the method of this invention.

FIG. 5 is a diagrammatic representation of a scheme involved in the synthesis of a 2'-deoxy-2'-N-phthaloyl adenosine 3'-O-(2-cyanoethyl-N,N-diisopropylphosphoramidite) (25) and 2'-deoxy-2'-amino adenosine (26) by the method of this invention.

FIG. 6 is a diagrammatic representation of a scheme involved in the synthesis of a 2'-deoxy-2'-N-phthaloyl guanosine 3'-O-(2-cyanoethyl-N,N-diisopropylphosphoramidite) (36) and 2'-deoxy-2'-amino guanosine (37) by the method of this invention.

FIG. 7 is a diagrammatic representation of a scheme involved in the synthesis of 5'-O-dimethoxytrityl-2'-O-tert-butyldimethylsilyl-N4-acetyl cytidine 3'-O-(2-cyanoethyl-N,N-diisopropylphosphoramidite) (43) by the method of this invention.

FIG. 8 is a diagrammatic representation of a scheme involved in the synthesis of 5'-O-dimethoxytrityl-2'-O-tert-butyldimethylsilyl uridine 3'-O-(2-cyanoethyl-N,N-diisopropylphosphoramidite) (48) by the method of this invention.

FIG. 9 is a diagrammatic representation of a scheme involved in the synthesis of 5'-O-dimethoxytrityl-2'-O-tert-butyldimethylsilyl-N6-benzoyl adenosine 3'-O-(2-cyanoethyl-N,N-diisopropylphosphoramidite) (54) by the method of this invention.

FIG. 10 is a diagrammatic representation of a scheme involved in the synthesis of 5'-O-dimethoxytrityl-2'-O-tert-butyldimethylsilyl-N2-isobutyryl guanosine 3'-O-(2-cyanoethyl-N,N-diisopropylphosphoramidite) (60) by the method of this invention.

FIG. 11 is a diagrammatic representation of a scheme involved in the synthesis of 5'-O-dimethoxytrityl-2'-O-methyl-N2-isobutyryl guanosine 3'-O-(2-cyanoethyl-N,N-diisopropylphosphoramidite) (69) and 2'-O-methyl guanosine (70) by the method of this invention.

FIG. 12 is a diagrammatic representation of a competing elimination reaction that occurs, for example, in step IV of FIG. 3 and in step III in FIGS. 4 and 5.

FIG. 13 is a diagrammatic representation of a scheme involved in the synthesis of 2'-O-methyl adenosine (75) by the method of this invention. The method of synthesis shown in FIG. 13 can be used to synthesize 2'-O-methyl phosphoramidites for oligonucleotide synthesis and other 2'-O-methyl derivatives.

FIG. 14 is a diagrammatic representation of a scheme involved in the synthesis of 2'-O-methyl adenosine (75) by the method of this invention using N6-imidazole adenosine intermediates. The method of synthesis shown in FIG. 14 can be used to synthesize 2'-O-methyl phosphoramidites for oligonucleotide synthesis and other 2'-O-methyl derivatives.

FIG. 15 is a diagrammatic representation of a scheme involved in the synthesis of 1,4-anhydro-2-deoxy-D-erythro-pentitol derivatives by methods of this invention. The method of synthesis shown in FIG. 15 can be used to synthesize 1,4-anhydro-2-deoxy-D-erythro-pentitol phosphoramidites and 1,4-anhydro-2-deoxy-D-erythro-pentitol succinates for use in oligonucleotide synthesis.

DETAILED DESCRIPTION OF THE INVENTION

The term "nucleoside" as used herein refers to a heterocyclic nitrogenous base, particularly a purine or pyrimidine, in an N-glycosidic linkage with a sugar, particularly a pentose. Nucleosides include both L- and D-nucleoside isomers.

The term "C-nucleoside" as used herein refers to a heterocyclic or aromatic group or aglycon, in C-glycosidic linkage with a sugar, particularly a pentose. C-nucleosides include both L- and D-C-nucleoside isomers.

The term "ribofuranosyl nucleoside" as used herein refers to a nucleoside or nucleoside analog comprising a 2'-hydroxyl group in a L- or D-beta-ribofuranosyl configuration.

The term "arabinofuranosyl nucleoside" as used herein refers to a nucleoside or nucleoside analog comprising a 2'-hydroxyl group in a L- or D-beta-arabinofuranosyl configuration.

The term "nucleophile" as used herein refers to a basic, electron-rich reagent that contains a lone pair of electrons and forms a new bond to a carbon atom. Nucleophiles can be anions or neutrally charged. Examples include, but are not limited to, carbanions, oxygen anions, halide anions, sulfur anions, nitrogen anions, nitrogen bases, alcohols, water and thiols.

The term "leaving group" as used herein refers to a weakly basic chemical entity that readily releases carbon, and takes a lone pair of electrons from said carbon atom. Examples include, but are not limited to, triflates, nosylates, brosylates, p-toluene sulfonates, trifluoroacetates, and mesylates.

The term "hindered base" as used herein refers to a weakly nucleophilic, strongly basic amine base.

The term "protected 1-β-D-arabinofuranosyl nucleoside" as used herein refers to a 1-β-D-arabinofuranosyl nucleoside that comprises protecting groups. The protecting groups are used to prevent undesirable side reactions with reactive groups present in the nucleoside, thereby allowing selective reaction at the desired location within the nucleoside of interest. Protecting groups are readily introduced and removed; both reactions occurring in high yield. For example, protection of nucleic acid base exocyclic amines with acyl groups, or protection of nucleoside 5',3'-hydroxyls with a di-O-tetraisopropyldisiloxy or di-tert-butylsilanediyl group prevents undesirable reactions at these locations, thereby allowing selective reaction at the 2'-hydroxyl of the target nucleoside.

The term "protected 1-β-D-arabinofuranosyl C-nucleoside" as used herein refers to a 1-β-D-arabinofuranosyl C-nucleoside that comprises protecting groups. The protecting groups are used to prevent undesirable side reactions with reactive groups present in the nucleoside, thereby allowing selective reaction at the desired location within the nucleoside of interest. Protecting groups are readily introduced and removed; both reactions occurring in high yield. For example, protection of nucleic acid base exocyclic amines with acyl groups, or protection of nucleoside 5',3'-hydroxyls with a di-O-tetraisopropyldisiloxy or di-tert-butylsilanediyl group prevents undesirable reactions at these locations, thereby allowing selective reaction at the 2'-hydroxyl of the target C-nucleoside.

The terms "5',3'-cyclic silyl protecting group" or "5',3'-bridging silyl protecting group" or "simultaneous protection of 5' and 3' hydroxyls" as used herein refers to a protecting group that selectively protects both the 5' and 3' positions of a nucleoside or C-nucleoside via formation of a bridging intranucleoside silyl ether linkage between the 5'-hydroxyl and 3'-hydroxyl groups of the nucleoside or C-nucleoside. Such bridging groups include, but are not limited to di-O-tetraisopropyldisiloxy or di-tert-butylsilanediyl groups.

The term "2'-O-silyl" as used herein refers to a substituted silyl ether at the 2'-position of a nucleoside or C-nucleoside, for example, a 2'-O-tert-butyldimethylsilyl group.

The term "silylation" as used herein refers to the process of introducing a silyl, or silicon containing, group. Silyl groups include, but are not limited to tert-butyldimethylsilyl (TBDMS), triisopropylsilyl (TIPS), triethylsilyl (TES), trimethylsilyl (TMS), tert-butyldiphenylsilyl (TBDPS). The term "cyclic silylation" refers to the process of introducing a bridging silyl group, for example, a di-O-tetraisopropyldisiloxy or di-tert-butylsilanediyl group.

The term "desilylation" as used herein refers to the process of removing a silyl, or silicon containing, group.

The term "di-alkylsilanediyl" as used herein refers to a dialkyl-substituted silyl group, for example a di-tert-butylsilanediyl group.

The term "phosphitylating reagent" as used herein refers to a reagent used to introduce a phosphoramidite moiety.

The term "transient protection" as used herein refers to the practice of masking one or more sugar hydroxyl groups of a nucleoside or C-nucleoside with a protecting group, for example through formation of a trimethylsilyl ether, prior to the introduction of a nucleic acid base protecting group, for example an acyl group, followed by the hydrolysis of the protecting group(s) to reveal the free hydroxyls.

The term "nucleic acid base protection" as used herein refers to the introduction of an exocyclic amine protecting group, for example an acyl or formamide group, on the nucleic acid base of a nucleoside.

The term "5'-hydroxyl protecting group compatible with oligonucleotide synthesis" or "acid labile protecting moiety" refers to a protecting group, such as the dimethoxytrityl, monomethoxytrityl, and/or trityl groups or other protecting groups, that can be used in a solid phase or solution phase oligonucleotide synthesis.

The term "acyl group" as used herein refers to a chemical entity comprising the general formula R—C(O)— where R represents any aliphatic, alicyclic, or aromatic group and C(O) represents a carbonyl.

The term "acylation" as used herein refers to any process whereby an acid, acid halide or acid anhydride is used to convert a hydroxyl group into an ester, or an amine into an amide.

The term "depyrimidination" as used herein refers to cleavage of a nucleoside C—N glycosidic bond between a pyrimidine base and a nucleosidic sugar component.

The term "succinate moiety" as used herein refers to a chemical moiety comprising at one or more succinyl groups, including any salts thereof, for example triethylamine salts.

The term "phosphoramidite moiety" as used herein refers to a nitrogen containing trivalent phosphorous derivative, for example, a 2-cyanoethyl-N,N-diisopropylphosphoramidite.

The term "alkyl" as used herein refers to a saturated aliphatic hydrocarbon, including straight-chain, branched-chain "isoalkyl", and cyclic alkyl groups. The term "alkyl" also comprises alkoxy, alkyl-thio, alkyl-thio-alkyl, alkoxyalkyl, alkylamino, alkenyl, alkynyl, alkoxy, cycloalkenyl, cycloalkyl, cycloalkylalkyl, heterocycloalkyl, heteroaryl, $C_1$–$C_6$ hydrocarbyl, aryl or substituted aryl groups. Preferably, the alkyl group has 1 to 12 carbons. More preferably it is a lower alkyl of from 1 to 7 carbons, more preferably 1 to 4 carbons. The alkyl group can be substituted or unsubstituted. When substituted, the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, $C_1$–$C_6$ hydrocarbyl, aryl or substituted aryl groups. The term "alkyl" also includes alkenyl groups containing at least one carbon—carbon double bond, including straight-chain, branched-chain, and cyclic groups. Preferably, the alkenyl group has 2 to 12 carbons. More preferably, it is a lower alkenyl of from 2 to 7 carbons, even more preferably 2 to 4 carbons. The alkenyl group can be substituted or unsubstituted. When substituted, the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, $C_1$–$C_6$ hydrocarbyl, aryl or substituted aryl groups. The term "alkyl" also includes alkynyl groups containing at least one carbon—carbon triple bond, including straight-chain, branched-chain, and cyclic groups. Preferably, the alkynyl group has 2 to 12 carbons. More preferably it is a lower alkynyl of from 2 to 7 carbons, more preferably 2 to 4 carbons. The alkynyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, $C_1$–$C_6$ hydrocarbyl, aryl or substituted aryl groups. Alkyl groups or moieties of the invention can also include aryl, alkylaryl, carbocyclic aryl, heterocyclic aryl, amide and ester groups. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

The term "alkanoyl" as used herein refers to an alkyl group attached to the parent molecular moiety through a carbonyl group.

The term "alkoxyalkyl" as used herein refers to an alkyl-O-alkyl ether, for example methoxyethyl or ethoxymethyl.

The term "alkyl-thio-alkyl" as used herein refers to an alkyl-S-alkyl thioether, for example methylthiomethyl or methylthioethyl.

The term "amino" as used herein refers to a nitrogen containing group as is known in the art derived from ammonia by the replacement of one or more hydrogen radicals by organic radicals. For example, the terms "aminoacyl" and "aminoalkyl" refer to specific N-substituted organic radicals with acyl and alkyl substituent groups respectively.

The term "amination" as used herein refers to a process in which an amino group or substituted amine is introduced into an organic molecule.

The term "exocyclic amine protecting moiety" as used herein refers to a nucleobase amino protecting group compatible with oligonucleotide synthesis, for example an acyl or amide group.

The term "silylating reagent" as used herein refers to a chemical reagent used to introduce a silyl group to a compound.

The term "selective desilylation" as used herein refers to the selective removal of one silyl group from a compound in the presence of another silyl group.

The term "alkenyl" as used herein refers to a straight or branched hydrocarbon of a designed number of carbon atoms containing at least one carbon—carbon double bond. Examples of "alkenyl" include vinyl, allyl, and 2-methyl-3-heptene.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

The term "alkynyl" as used herein refers to a straight or branched hydrocarbon of a designed number of carbon atoms containing at least one carbon—carbon triple bond. Examples of "alkynyl" include propargyl, propyne, and 3-hexyne.

The term "aryl" as used herein refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkenyl" as used herein refers to a $C_3$–$C_8$ cyclic hydrocarbon containing at least one carbon—carbon double bond. Examples of cycloalkenyl include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloalkyl" as used herein refers to a $C_3$–$C_8$ cyclic hydrocarbon. Examples of cycloalkyl include cyclopropyl, cyclobutyl, cyclopentyl, cyclohexyl, cycloheptyl and cyclooctyl.

The term "cycloalkylalkyl," as used herein, refers to a C3–C7 cycloalkyl group attached to the parent molecular moiety through an alkyl group, as defined above. Examples of cycloalkylalkyl groups include cyclopropylmethyl and cyclopentylethyl.

The terms "halogen" or "halo" as used herein refers to indicate fluorine, chlorine, bromine, and iodine.

The term "heterocycloalkyl," as used herein refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrolidinyl.

The term "heteroaryl" as used herein refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "$C_1$–$C_6$ hydrocarbyl" as used herein refers to straight, branched, or cyclic alkyl groups having 1–6 carbon atoms, optionally containing one or more carbon—carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentene, cyclopropylmethyl, cyclopropyl, cyclohexylmethyl, cyclohexyl and propargyl. When reference is made herein to $C_1$–$C_6$ hydrocarbyl containing one or two double or triple bonds it is understood that at least two carbons are present in the alkyl for one double or triple bond, and at least four carbons for two double or triple bonds.

The term "nitrogen protecting group," as used herein, refers to groups known in the art that are readily introduced on to and removed from a nitrogen. Examples of nitrogen protecting groups include Boc, Cbz, benzoyl, and benzyl. See also "Protective Groups in Organic Synthesis", 3rd Ed., Greene, T. W. and related publications.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The present invention also encompasses prodrugs of the compounds of Formulae I–XVII.

The present invention also encompasses the acylated prodrugs of the compounds of Formulae I–XVII. Those skilled in the art will recognize various synthetic methodologies, which can be employed to prepare non-toxic pharmaceutically acceptable addition salts and acylated prodrugs of the compounds encompassed by Formulae I–XVII.

The present invention also provides tritium labeled probes derived from the compounds of Formulae I–XVII. Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph. In addition, tritium can also be introduced by tritium-halogen exchange with tritium gas, transition metal catalyzed tritium gas reduction of unsaturated bonds, or sodium borohydride reduction of ketones, aldehydes, and imines.

The compounds of this invention can contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The starting materials and various intermediates can be obtained from commercial sources, prepared from commercially available organic compounds, or prepared using well-known synthetic methods. The present invention also encompasses the prodrugs of the compounds of Formulae I–XVII. Those skilled in the art will recognize various synthetic methodologies that can be employed to prepare non-toxic pharmaceutically acceptable prodrugs of the compounds encompassed by Formulae I–XVII. Those skilled in the art will recognize a wide variety of non-toxic pharmaceutically acceptable solvates, such as water, ethanol, mineral oil, vegetable oil, and dimethylsulfoxide.

The compounds of general Formulae I–XVII can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formulae I–XVII and a pharmaceutically acceptable carrier. One or more compounds of general Formulae I–XVII can be present in association with one or more non-toxic pharmaceutically acceptable carriers and/or diluents and/or adjuvants, and if desired other active ingredients. The pharmaceutical compositions containing compounds of general Formulae I–XVII may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions may contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example, sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example, sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol, anhydrides, for example, sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example, glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formulae I–XVII can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formulae I–XVII can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

In one aspect of the present invention, a novel method for the synthesis of 2'-deoxy-2'-amino purine and pyrimidine nucleosides and C-nucleosides is provided. The novel method employs fewer synthetic steps, avoids the use of azides, and concomitantly introduces N-phthaloyl protection of the 2'-amine. In one embodiment, the present invention provides a method for synthesizing 2'-deoxy-2'amino and 2'-deoxy-2'-N-phthaloyl nucleosides. The method comprises the use of phthalimide and/or a substituted phthalimide as a nucleophile in the displacement of a leaving group present at the 2'-position of a 1-β-D-arabinofuranosyl nucleoside to generate a 2'-deoxy-2'-N-phthaloyl nucleoside. Subsequent cleavage of the phthaloyl protection with a suitable base results in the formation of a 2'-deoxy-2'-amino nucleoside. The method can be scaled up to kilogram or greater quantities. In another embodiment, the present invention provides a method for the synthesis of 2'-deoxy-2'-amino and 2'-deoxy-2'-N-phthaloyl C-nucleosides. Similar to the above method, the synthesis comprises the use of phthalimide and/or a substituted phthalimide as a nucleophile in the displacement of a leaving group present at the 2'-position of a 1-β-D-arabinofuranosyl C-nucleoside to generate a 2'-deoxy-2'-N-phthaloyl C-nucleoside. Subsequent cleavage of the phthaloyl protection with a suitable base results in the formation of a 2'-deoxy-2'-amino C-nucleoside. The method can be scaled up to kilogram or greater quantities.

Thus, in a preferred embodiment, the invention provides a method for the synthesis of a 2'-deoxy-2'-N-phthaloyl nucleoside, comprising the steps of:

(a) introducing a leaving group at the 2'-position of a 1-β-D-arabinofuranosyl nucleoside; and (b) displacing the leaving group from step (a) with a phthalimide or substituted phthalimide nucleophile to yield the 2'-deoxy-2'-N-phthaloyl nucleoside.

The 1-β-D-arabinofuranosyl nucleoside can be protected or unprotected.

Preferably, the leaving group at the 2' position of the 1-β-D-arabinofuranosyl nucleoside is introduced by contacting the 1-β-D-arabinofuranosyl nucleoside with a sulfonic anhydride or sulfonyl chloride. Suitable reagents include trifluoromethanesulfonic anhydride, trifluoromethanesulfonyl chloride, methanesulfonic anhydride, and methanesulfonyl chloride.

Also, the displacement step (step b) can occur in the presence of a hindered base. Preferably, the hindered base is DBU (1,8-Diazabicyclo[5.4.0]undec-7-ene), DBN (1,5-Diazabicyclo[4.3.0]non-5-ene), Dabco (1,4-Diazabicyclo[2.2.2]octane), or 2-tert-Butylimino-2-diethylamino-1,3-dimethyl-perhydro-1,3,2-diazaphosphorine.

In another embodiment, the present invention provides a method for synthesizing a 2'-deoxy-2'-N-phthaloyl nucleoside, comprising the step of contacting a 2'-trifluoromethanesulfonyl-1-β-D-arabinofuranosyl nucleoside with a phthalimide or substituted phthalimide nucleophile under conditions suitable for formation of said 2'-deoxy-2'-N-phthaloyl nucleoside.

In yet another preferred embodiment, the invention provides a method for synthesizing a 2'-deoxy-2'-N-phthaloyl nucleoside, comprising the step of contacting a 2'-methanesulfonyl-1-β-D-arabinofuranosyl nucleoside with a phthalimide or substituted phthalimide nucleophile under conditions suitable for formation of said 2'-deoxy-2'-N-phthaloyl nucleoside. In the above two methods, suitable conditions can include the use of a hindered base. Preferably, the hindered base is DBU (1,8-Diazabicyclo[5.4.0]undec-7-ene), DBN (1,5-Diazabicyclo[4.3.0]non-5-ene), Dabco (1,4-Diazabicyclo[2.2.2]octane), and 2-tert-Butylimino-2-diethylamino-1,3-dimethyl-perhydro-1,3,2-diazaphosphorine hindered bases.

In any of the above described embodiments, preferred phthalimide or substituted phthalimide nucleophiles include phthalimide, 4,5-dichlorophthalimide, 3,4,5,6,-tetrachlorophthalamide, 3-nitrophthalamide, and 4-nitrophthalamide. Also, in any of the above described embodiments, preferred 1-β-D-arabinofuranosyl nucleosides include 5',3'-di-O-tetraisopropyldisiloxy-1-β-D-arabinofuranosyl-N4-acyl cytosine, 5',3'-di-O-tetraisopropyldisiloxy-1-β-D-arabinofuranosyl-N2-acyl adenine, 5',3'-di-O-tetraisopropyldisiloxy-1-β-D-arabinofuranosyl adenine, 5',3'-di-O-tetraisopropyldisiloxy-1-β-D-arabinofuranosyl uracil, 5',3'-di-O-tetraisopropyldisiloxy-1-β-D-arabinofuranosyl-N2-acyl guanine, 5',3'-di-O-tetraisopropyldisiloxy-1-β-D-arabinofuranosyl-N2-acyl-O6-diphenylcarbamoyl guanine, 5',3'-di-O-tetraisopropyldisiloxy-1-β-D-arabinofuranosyl-N2-acyl-O6-nitrophenyl guanine, 5',3'-O-di-tert-butylsilanediyl-1-β-D-arabinofuranosyl-N4-acyl cytosine, 5',3'-di-tert-butylsilanediyl-1-β-D-arabinofuranosyl uracil, 5',3'-O-di-tert-butylsilanediyl-1-β-D-arabinofuranosyl-N2-acyl adenine, 5',3'-O-di-tert-butylsilanediyl-1-β-D-arabinofuranosyl adenine, 5',3'-O-di-tert-butylsilanediyl-1-β-D-arabinofuranosyl-N2-acyl-O6-nitrophenyl guanine, and 5',3'-O-di-tert-butylsilanediyl-1-βD-arabinofuranosyl-N2-acyl-O6-diphenylcarbamoyl guanine.

In instances in which the 1-β-D-arabinofuranosyl nucleoside is protected by an acyl group (i.e., by exocyclic amine protection), the acyl group is acetyl, benzoyl, isobutyryl, phenoxyacetyl, phenylacetyl, tert-butylphenoxyacetyl, or tert-butylbenzoyl.

Also, in the synthesis of a guanosine nucleoside, preferably dimethylformamidine (DMF) protection is used to protect the N2 nitrogen.

Thus, in one embodiment, the present invention provides a method for synthesizing a phthaloyl protected 2'-deoxy-2'-amino nucleoside (2'-deoxy-2'-N-phthaloyl nucleoside) including the steps of: (a) introducing a leaving group at the 2'-position of a 1-β-D-arabinofuranosyl nucleoside by contacting the 1-β-D-arabinofuranosyl nucleoside, which can be protected or unprotected, with a sulfonic anhydride or sulfonyl chloride such as trifluoromethanesulfonic anhydride, trifluoromethanesulfonyl chloride, methanesulfonic anhydride, or methanesulfonyl chloride, and (b) displacing the leaving group from step (a) with a phthalimide or substituted phthalimide nucleophile such as 4,5-dichorophthalimide, 3,4,5,6-tetrachorophthalimide, 3-nitrophthalimide, and 4-nitrophthalimide, in the presence of a hindered base such as DBU (1,8-Diazabicyclo[5.4.0]undec-7-ene), DBN (1,5-Diazabicyclo[4.3.0]non-5-ene), Dabco (1,4-Diazabicyclo[2.2.2]octane), and 2-tert-Butylimino-2-diethylamino-1,3-dimethyl-perhydro-1,3,2-diazaphosphorine or the equivalent thereof, to yield a 2'-deoxy-2'-N-phthaloyl nucleoside.

In another embodiment of the present invention, a method for the synthesis of a 2'-deoxy-2'-amino nucleosides is provided. This method comprises the steps of:
(a) introducing a leaving group at the 2'-position of a 1-β-D-arabinofuranosyl nucleoside;
(b) displacing said leaving group from step (a) with a phthalimide or substituted phthalimide nucleophile to yield a 2'-deoxy-2'-N-phthaloyl nucleoside; and
(c) deprotecting said 2'-deoxy-2'-N-phthaloyl nucleoside to yield said 2'-deoxy-2'-amino nucleoside.

The 2'-position of the 1-β-D-arabinofuranosyl nucleoside can be protected or unprotected.

Preferably, the leaving group at the 2' position of the 1-β-D-arabinofuranosyl nucleoside is introduced by contacting the 1-β-D-arabinofuranosyl nucleoside with a sulfonic anhydride or sulfonyl chloride. Suitable reagents include trifluoromethanesulfonic anhydride, trifluoromethanesulfonyl chloride, methanesulfonic anhydride, and methanesulfonyl chloride.

The preferred phthalimide nucleophiles include phthalimide, or substituted phthalimide nucleophiles, such as 4,5-dichlorophthalimide, 3,4,5,6,-tetrachlorophthalamide, 3-nitrophthalamide, and 4-nitrophthalamide.

Also, preferred 1-β-D-arabinofuranosyl nucleosides include 5',3'-di-O-tetraisopropyldisiloxy-1-β-D-arabinofuranosyl-N4-acyl cytosine, 5',3'-di-O-tetraisopropyldisiloxy-1-β-D-arabinofuranosyl-N2-acyl adenine, 5',3'-di-O-tetraisopropyldisiloxy-1-β-D-arabinofuranosyl adenine, 5',3'-di-O-tetraisopropyldisiloxy-1-β-D-arabinofuranosyl uracil, 5',3'-di-O-tetraisopropyldisiloxy-1-β-D-arabinofuranosyl-N2-acyl guanine, 5',3'-di-O-tetraisopropyldisiloxy-1-β-D-arabinofuranosyl-N2-acyl-O6-diphenylcarbamoyl guanine, 5',3'-di-O-tetraisopropyldisiloxy-1-β-D-arabinofuranosyl-N2-acyl-O6-nitrophenyl guanine, 5',3'-O-di-tert-butylsilanediyl-1-β-D-arabinofuranosyl-N4-acyl cytosine, 5',3'-di-tert-butylsilanediyl-1-β-D-arabinofuranosyl uracil, 5',3'-O-di-tert-butylsilanediyl-1-β-D-arabinofuranosyl-N2-acyl adenine, 5',3'-O-di-tert-butylsilanediyl-1-β-D-arabinofuranosyl adenine, 5',3'-O-di-tert-butylsilanediyl-1-β-D-arabinofuranosyl-N2-acyl-O6-nitrophenyl guanine, and 5',3'-O-di-tert-butylsilanediyl-1-βD-arabinofuranosyl-N2-acyl-O6-diphenylcarbamoyl guanine.

In instances in which the 1-β-D-arabinofuranosyl nucleoside is protected by an acyl group (i.e., by exocyclic amine protection), such as acetyl, benzoyl, isobutyryl, phenoxyacetyl, phenylacetyl, tert-butylphenoxyacetyl, or tert-butylbenzoyl.

Also, in the synthesis of guanosine nucleosides, preferably dimethylformamidine (DMF) protection is used to protect the N2 nitrogen.

The displacement of the leaving group can occur in the presence of a hindered base. Preferably, the hindered base is DBU (1,8-Diazabicyclo[5.4.0]undec-7-ene), DBN (1,5-

Diazabicyclo[4.3.0]non-5-ene), Dabco (1,4-Diazabicyclo [2.2.2]octane), or 2-tert-Butylimino-2-diethylamino-1,3-dimethyl-perhydro-1,3,2-diazaphosphorine.

The deprotection step of the inventive method can occur in the presence of a base. Preferably, the base is an alkylamine or hydrazine. Preferably, the alkylamine is methylamine, such as aqueous methylamine, ethanolic methylamine, methanolic methylamine. Preferably, the hydrazine is methyl hydrazine. Even more preferably, the methylamine is aqueous methylamine, such as about 30–40% aqueous methylamine.

The method can be used to synthesize nucleosides, nucleotides and oligonucleotides comprising at least one 2'-deoxy-2'amino nucleoside. In a preferred embodiment, the method for the synthesis of a 2'-deoxy-2'-amino nucleoside of the instant invention can be used to synthesize a 2'-deoxy-2'-amino nucleotide triphosphate.

In another embodiment, the invention provides a method for synthesizing a phthaloyl protected 2'-deoxy-2'-amino nucleoside phosphoramidite (2'-deoxy-2'-N-phthaloyl nucleoside phosphoramidite) comprising the steps of:

(a) introducing a leaving group at the 2'-position of a 1-β-D-arabinofuranosyl nucleoside by contacting the 1-β-D-arabinofuranosyl nucleoside, which can be protected or unprotected, with a sulfonic anhydride or sulfonyl chloride, (b) displacing the leaving group from step (a) with a phthalimide or substituted phthalimide nucleophile in the presence of a hindered base to yield a 2'-deoxy-2'-N-phthaloyl nucleoside, (c) introducing a 5'-protecting group to provide selective protection of the 5'-hydroxyl, and (d) introducing a phosphoramidite group at the 3'-position of the 5'-protected-2'-deoxy-2'-N-phthaloyl nucleoside with a phosphitylating reagent.

Suitable sulfonic anhydride or sulfonyl chloride reagents include trifluoromethanesulfonic anhydride, trifluoromethanesulfonyl chloride, methanesulfonic anhydride, and methanesulfonyl chloride.

Suitable phthalimide or substituted phthalimides include phthalimide, 4,5-dichorophthalimide, 3,4,5,6-tetrachorophthalimide, 3-nitrophthalimide, and 4-nitrophthalimide. Also, suitable hindered bases include DBU (1,8-Diazabicyclo[5.4.0]undec-7-ene), DBN (1,5-Diazabicyclo[4.3.0]non-5-ene), Dabco (1,4-Diazabicyclo [2.2.2]octane), and 2-tert-Butylimino-2-diethylamino-1,3-dimethyl-perhydro-1,3,2-diazaphosphorine or the equivalent thereof, to yield a 2'-deoxy-2'-N-phthaloyl nucleoside.

An example of a suitable 5'-protecting group is a dimethoxytrityl group or an equivalent thereof.

An example of a suitable phosphitylating reagent is 2-cyanoethyl-N,N-diisopropylchlorophosphoramidite.

In a preferred embodiment of the inventive method, the 2'-deoxy-2'-N-phthaloyl nucleoside synthesized in step (b) is deprotected with a source of fluoride ion, such as TEA.3HF (triethylamine trihydrofluoride), TBAF or the equivalent thereof, for the selective removal of a silyl ether or disilyl ether protecting group, such as 5',3'-O-di-tert-butylsilanediyl or 5',3'-di-O-tetraisopropyldisiloxane protection, which can be present or absent, prior to step (c).

Preferred 1-β-D-arabinofuranosyl nucleosides include 5',3'-di-O-tetraisopropyldisiloxy-1-β-D-arabinofuranosyl-N4-acyl cytosine, 5',3'-di-O-tetraisopropyldisiloxy-1-β-D-arabinofuranosyl-N2-acyl adenine, 5',3'-di-O-tetraisopropyldisiloxy-1-β-D-arabinofuranosyl adenine, 5',3'-di-O-tetraisopropyldisiloxy-1-β-D-arabinofuranosyl uracil, 5',3'-di-O-tetraisopropyldisiloxy-1-β-D-arabinofuranosyl-N2-acyl guanine, 5',3'-di-O-tetraisopropyldisiloxy-1-β-D-arabinofuranosyl-N2-acyl-O6-diphenylcarbamoyl guanine, 5',3'-di-O-tetraisopropyldisiloxy-1-β-D-arabinofuranosyl-N2-acyl-O6-nitrophenyl guanine, 5',3'-O-di-tert-butylsilanediyl-1-β-D-arabinofuranosyl-N4-acyl cytosine, 5',3'-di-tert-butylsilanediyl-1-β-D-arabinofuranosyl uracil, 5',3'-O-di-tert-butylsilanediyl-1-β-D-arabinofuranosyl-N2-acyl adenine, 5',3'-O-di-tert-butylsilanediyl-1-β-D-arabinofuranosyl adenine, 5',3'-O-di-tert-butylsilanediyl-1-β-D-arabinofuranosyl-N2-acyl-O6-nitrophenyl guanine, and 5',3'-O-di-tert-butylsilanediyl-1-βD-arabinofuranosyl-N2-acyl-O6-diphenylcarbamoyl guanine.

In instances in which the 1-β-D-arabinofuranosyl nucleoside is protected by an acyl group (i.e., by exocyclic amine protection), such as acetyl, benzoyl, isobutyryl, phenoxyacetyl, phenylacetyl, tert-butylphenoxyacetyl, or tert-butylbenzoyl.

Also, in the synthesis of guanosine phosphoramidites, preferably dimethylformamidine (DMF) protection is used to protect the N2 nitrogen.

In other embodiments of the present invention, methods for synthesizing a 2'-deoxy-2'-N-phthaloyl C-nucleoside, a 2'-deoxy-2'-amino C-nucleoside, and a phthaloyl protected 2'-deoxy-2'-amino C-nucleoside phosphoramidite are provided.

The method for synthesizing a 2'-deoxy-2'-N-phthaloyl C-nucleoside comprises:

(a) introducing a leaving group at the 2'-position of a 1-β-D-arabinofuranosyl C-nucleoside, and, (b) displacing the leaving group from step (a) with a phthalimide or substituted phthalimide nucleophile in the presence of a hindered base, to yield the 2'-deoxy-2'-N-phthaloyl C-nucleoside.

The 2'-position of the 1-β-D-arabinofuranosyl C-nucleoside can be protected or unprotected.

Preferably, the leaving group at the 2'position of the 1-β-D-arabinofuranosyl C-nucleoside is introduced by contacting the 1-β-D-arabinofuranosyl C-nucleoside with a sulfonic anhydride or sulfonyl chloride. Suitable reagents include trifluoromethanesulfonic anhydride, trifluoromethanesulfonyl chloride, methanesulfonic anhydride, or methanesulfonyl chloride.

Also, the displacement step can occur in the presence of a hindered base. Preferably, the hindered base is DBU (1,8-Diazabicyclo[5.4.0]undec-7-ene), DBN (1,5-Diazabicyclo[4.3.0]non-5-ene), Dabco (1,4-Diazabicyclo [2.2.2]octane), or 2-tert-Butylimino-2-diethylamino-1,3-dimethyl-perhydro-1,3,2-diazaphosphorine.

In another embodiment, the present invention provides a method for synthesizing a 2'-deoxy-2'-N-phthaloyl C-nucleoside, comprising the step of contacting a 2'-trifluoromethanesulfonyl-1-β-D-arabinofuranosyl C-nucleoside with a phthalimide or substituted phthalimide nucleophile under conditions suitable for formation of said 2'-deoxy-2'-N-phthaloyl C-nucleoside.

In yet another embodiment, the invention provides a method for synthesizing a 2'-deoxy-2'-N-phthaloyl C-nucleoside, comprising the step of contacting a 2'-methanesulfonyl-1-β-D-arabinofuranosyl C-nucleoside with a phthalimide or substituted phthalimide nucleophile under conditions suitable for formation of said 2'-deoxy-2'-N-phthaloyl C-nucleoside. In the above two methods, suitable conditions can include the use of a hindered base. Preferably, the hindered base is DBU (1,8-Diazabicyclo [5.4.0]undec-7-ene), DBN (1,5-Diazabicyclo[4.3.0]non-5- ene), Dabco (1,4-Diazabicyclo[2.2.2]octane), or 2-tert-Butylimino-2-diethylamino-1,3-dimethyl-perhydro-1,3,2-diazaphosphorine.

In another embodiment of the present invention, a method for the synthesis of a 2'-deoxy-2'-amino C-nucleoside is provided. This method comprises the steps of:

(a) introducing a leaving group at the 2'-position of a 1-β-D-arabinofuranosyl C-nucleoside;

(b) displacing said leaving group from step (a) with a phthalimide or substituted phthalimide nucleophile to yield a 2'-deoxy-2'-N-phthaloyl C-nucleoside; and (c) deprotecting said 2'-deoxy-2'-N-phthaloyl C-nucleoside to yield said 2'-deoxy-2'-amino C-nucleoside.

The 2'-position of the 1-β-D-arabinofuranosyl C-nucleoside can be protected or unprotected. Preferably, the leaving group at the 2'position of the 1-β-D-arabinofuranosyl C-nucleoside is introduced by contacting the 1-β-D-arabinofuranosyl C-nucleoside with a sulfonic anhydride or sulfonyl chloride. Suitable reagents include trifluoromethanesulfonic anhydride, trifluoromethanesulfonyl chloride, methanesulfonic anhydride, and methanesulfonyl chloride.

The displacement can occur in the presence of a hindered base. Preferably, the hindered base is DBU (1,8-Diazabicyclo[5.4.0]undec-7-ene), DBN (1,5-Diazabicyclo[4.3.0]non-5-ene), Dabco (1,4-Diazabicyclo[2.2.2]octane), or 2-tert-Butylimino-2-diethylamino-1,3-dimethyl-perhydro-1,3,2-diazaphosphorine.

The deprotection can occur in the presence of a base. Preferably, the base is an alkylamine or hydrazine. Preferably, the alkylamine is methylamine, such as aqueous methylamine, ethanolic methylamine, methanolic methylamine. Preferably, the hydrazine is methyl hydrazine. Even more preferably, the methylamine is aqueous methylamine, such as about 30–40% aqueous methylamine.

The method can be used to synthesize C-nucleosides, C-nucleotides and C-oligonucleotides comprising at least one 2'-deoxy-2'amino nucleoside. In a preferred embodiment, the method for the synthesis of a 2'-deoxy-2'-amino C-nucleoside of the instant invention can be used to synthesize a 2'-deoxy-2'-amino C-nucleotide triphosphate.

In another embodiment, the invention provides a method for synthesizing a phthaloyl protected 2'-deoxy-2'-amino C-nucleoside phosphoramidite (2'-deoxy-2'-N-phthaloyl nucleoside phosphoramidite) comprising the steps of:

(a) introducing a leaving group at the 2'-position of a 1-β-D-arabinofuranosyl C-nucleoside by contacting the 1-β-D-arabinofuranosyl C-nucleoside, which can be protected or unprotected, with a sulfonic anhydride or sulfonyl chloride, (b) displacing the leaving group from step (a) with a phthalimide or substituted phthalimide nucleophile in the presence of a hindered base to yield a 2'deoxy-2'N-phthaloyl C-nucleoside', (c) introducing a 5'-protecting group to provide selective protection of the 5'-hydroxyl, and (d) introducing a phosphoramidite group at the 3'-position of the 5'-protected-2'-deoxy-2'-N-phthaloyl C-nucleoside with a phosphitylating reagent. Suitable sulfonic anhydride or sulfonyl chloride reagents in step (a) include trifluoromethanesulfonic anhydride, trifluoromethanesulfonyl chloride, methanesulfonic anhydride, and methanesulfonyl chloride.

Preferred phthalimide and substituted phthalimides include phthalimide, 4,5-dichorophthalimide, 3,4,5,6-tetrachorophthalimide, 3-nitrophthalimide, and 4-nitrophthalimide. Also, suitable hindered bases include DBU (1,8-Diazabicyclo[5.4.0]undec-7-ene), DBN (1,5-Diazabicyclo[4.3.0]non-5-ene), Dabco (1,4-Diazabicyclo [2.2.2]octane), and 2-tert-Butylimino-2-diethylamino-1,3-dimethyl-perhydro-1,3,2-diazaphosphorine or the equivalent thereof, to yield a 2'-deoxy-2'-N-phthaloyl nucleoside, An example of a suitable 5'-protecting group is a dimethoxytrityl group or an equivalent thereof.

An example of a suitable phosphitylating reagent is 2-cyanoethyl-N,N-diisopropylchlorophosphoramidite.

In one embodiment of the inventive method, the 2'-deoxy-2'-N-phthaloyl nucleoside synthesized from step (b) is deprotected with a source of fluoride ion, such as TEA.3HF (triethylamine trihydrofluoride), TBAF or the equivalent thereof, for the selective removal of a silyl ether or disilyl ether protecting group, such as 5',3'-O-di-tert-butylsilanediyl or 5',3'-di-O-tetraisopropyldisiloxane protection, which can be present or absent, prior to step (c).

In any of the above described embodiments involving methods of synthesizing C-nucleosides, preferred phthalimide and substituted phthalimide nucleophiles include phthalimide, 4,5-dichlorophthalimide, 3,4,5,6,-tetrachlorophthalamide, 3-nitrophthalamide, and 4-nitrophthalamide.

Also, in any of the above described embodiments involving methods of synthesizing C-nucleosides, preferred 1-β-D-arabinofuranosyl nucleosides include 5',3'-di-O-tetraisopropyldisiloxy-1-β-D-arabinofuranosyl-N4-acyl cytosine, 5',3'-di-O-tetraisopropyldisiloxy-1-β-D-arabinofuranosyl-N2-acyl adenine, 5',3'-di-O-tetraisopropyldisiloxy-1-β-D-arabinofuranosyl adenine, 5',3'-di-O-tetraisopropyldisiloxy-1-β-D-arabinofuranosyl uracil, 5',3'-di-O-tetraisopropyldisiloxy-1-β-D-arabinofuranosyl-N2-acyl guanine, 5',3'-di-O-tetraisopropyldisiloxy-1-β-D-arabinofuranosyl-N2-acyl-O6-diphenylcarbamoyl guanine, 5',3'-di-O-tetraisopropyldisiloxy-1-β-D-arabinofuranosyl-N2-acyl-O6-nitrophenyl guanine, 5',3'-O-di-tert-butylsilanediyl-1-β-D-arabinofuranosyl-N4-acyl cytosine, 5',3'-di-tert-butylsilanediyl-1-β-D-arabinofuranosyl uracil, 5',3'-O-di-tert-butylsilanediyl-1-β-D-arabinofuranosyl-N2-acyl adenine, 5',3'-O-di-tert-butylsilanediyl-1-β-D-arabinofuranosyl adenine, 5',3'-O-di-tert-butylsilanediyl-1-β-D-arabinofuranosyl-N2-acyl-O6-nitrophenyl guanine, and 5',3'-O-di-tert-butylsilanediyl-1-βD-arabinofuranosyl-N2-acyl-O6-diphenylcarbamoyl guanine.

In instances in which the 1-β-D-arabinofuranosyl C-nucleoside is protected by an acyl group (i.e., by exocyclic amine protection), such as acetyl, benzoyl, isobutyryl, phenoxyacetyl, phenylacetyl, tert-butylphenoxyacetyl, or tert-butylbenzoyl.

Also, in the synthesis of guanosine and guanosine phosphoramidites, preferably dimethylformamidine (DMF) protection is used to protect the N2 nitrogen.

In another embodiment of the present invention, a method for synthesizing a 2'-deoxy-2'-N-phthaloyl cytidine phosphoramidite is provided. For example, the present invention provides a method for synthesizing 5'-O-dimethoxytrityl-2'-deoxy-2'-N-phthaloyl-N4-acetyl cytidine 3'-O-(2-cyanoethyl-N,N-diisopropylphosphoramidite), comprising the steps of:

(1) introducing an acyl group at the $N^4$ position of 1-β-D-arabinofuranosyl cytosine with an acylating agent, for example using acetic anhydride under conditions suitable for obtaining 1-β-D-arabinofuranosyl-N4-acetyl cytosine, (2) introducing a protecting group for the simultaneous protection of the 5'-hydroxyl and 3'-hydroxyl groups of the product from step (1), for example using 1,3-dichloro-1,1,3,3-tetraisopropyldisiloxane or di-tert-butylsilyl bis(trifluoromethanesulfonate) under conditions suitable for the isolation of 5',3'-di-O-tetraisopropyldisiloxy-1-β-D-arabinofuranosyl-N4-acetyl cytosine or 5',3'-O-di-tert-butylsilanediyl-1-β-D-arabinofaranosyl-N4-acetyl cytosine, (3) introducing a leaving group at the 2'-position of the product of step (2), for example using triflic anhydride or triflyl chloride in the presence of dimethylaminopyridine (DMAP) and/or pyridine under conditions suitable for obtaining 5',3'-di-O-tetraisopropyldisiloxy-2'-trifluoromethanesulfonyl-1-β-D-arabinofuranosyl-N4-acetyl cytosine or 5',3'-O-di-tert-butylsilanediyl-2'-trifluoromethanesulfonyl-1-β-D-arabinofuranosyl-N4-acetyl cytosine, (4) displacing the leaving group from the product of step (3) with a phthalimide or substituted phthalimide nucleophile, (5) deprotecting the product of step (4) with a source of fluoride ion, for example TEA.3HF, TBAF or the equivalent thereof for the selective removal of 5',3'-di-O-tetraisopropyldisiloxane or 5',3'-O-di-tert-butylsilanediyl protection under conditions suitable for the isolation of 2'-deoxy-2'-N-phthaloyl-N4-acetyl cytidine, (6) introducing a 5'-hydroxyl protecting group compatible with oligonucleotide synthesis to the product of step (5), for example by using 4'-4'-dimethoxytrityl chloride under conditions suitable for obtaining 5'-O-dimethoxytrityl-2'-deoxy-2'-N-phthaloyl-N4-acetyl cytidine, and (7) introducing a phosphoramidite moiety at the 3'-position of the product of step (6) with a phosphitylating reagent, for example using 2-cyanoethyl-N,N-diisopropylchlorophosphoramidite under conditions suitable for isolating 5'-O-dimethoxytrityl-2'-deoxy-2'-N-phthaloyl-N4-acetyl cytidine 3'-O-(2-cyanoethyl-N,N-diisopropylphosphoramidite).

In one embodiment, displacement of the leaving group can occur in the presence of a hindered base. For example, phthalimide can be used in combination with DBU (1,8-Diazabicyclo[5.4.0]undec-7-ene), DBN (1,5-Diazabicyclo[4.3.0]non-5-ene), Dabco (1,4-Diazabicyclo[2.2.2]octane), and/or 2-tert-Butylimino-2-diethylamino-1,3-dimethyl-perhydro-1,3,2-diazaphosphorine or the equivalent thereof to yield 5',3'-di-O-tetraisopropyldisiloxy-2'-deoxy-2'-N-phthaloyl-N4-acetyl cytidine or 5',3'-O-di-tert-butylsilanediyl-2'-deoxy-2'-N-phthaloyl-N4-acetyl cytidine.

In another embodiment, the invention provides another method for synthesizing a 2'-deoxy-2'-N-phthaloyl cytidine phosphoramidite, for example 5'-O-dimethoxytrityl-2'-deoxy-2'-N-phthaloyl-N4-acetyl cytidine 3'-O-(2-cyanoethyl-N,N-diisopropylphosphoramidite), comprising the steps of:

(1) introducing protection of the 5'-hydroxyl and 3'-hydroxyl groups of a 1-β-D-arabinofuranosyl cytosine, for example using cyclic silylation with 1,3-dichloro-1,1,3,3-tetraisopropyldisiloxane or di-tert-butylsilylbis(trifluoromethanesulfonate) under conditions suitable for the isolation of 5',3'-di-O-tetraisopropyldisiloxy-1-β-D-arabinofuranosyl cytosine or 5',3'-O-di-tert-butylsilanediyl-1-β-D-arabinofuranosyl cytosine, (2) introducing a leaving group at the 2'-position of the product of step (1), for example, using triflic anhydride or triflyl chloride in the presence of dimethylaminopyridine (DMAP) and/or pyridine under conditions suitable for obtaining 5',3'-di-O-tetraisopropyldisiloxy-2'-trifluoromethanesulfonyl-1-β-D-arabinofuranosyl cytosine or 5',3'-O-di-tert-butylsilanediyl-2'-trifluoromethanesulfonyl-1-β-D-arabinofuranosyl cytosine, (3) displacing the leaving group from the product of step (2) with a phthalimide or substituted phthalimide nucleophile, (4) introducing an acyl group at the $N^4$ position of the product of step (3) with an acylating agent, for example using acetic anhydride under conditions suitable for obtaining 5',3'-di-O-tetraisopropyldisiloxy-2'-deoxy-2'-N-phthaloyl-N4-acetyl cytidine or 5',3'-O-di-tert-butylsilanediyl-2'-deoxy-2'-N-phthaloyl-N4-acetyl cytidine, (5) deprotecting the product of step (4) with a source of fluoride ion, for example TEA.3HF, TBAF or the equivalent thereof for the selective removal of 5',3'-di-O-tetraisopropyldisiloxane or 5',3'-O-di-tert-butylsilanediyl protection under conditions suitable for the isolation of 2'-deoxy-2'-N-phthaloyl-N4-acetyl cytidine, (6) introducing a 5'-hydroxyl protecting group compatible with oligonucleotide synthesis to the product of step (5), for example, by using 4'-4'-dimethoxytrityl chloride under conditions suitable for obtaining 5'-O-dimethoxytrityl-2'-deoxy-2'-N-phthaloyl-N4-acetyl cytidine, and (7) introducing a phosphoramidite moiety at the 3'-position of the product of step (6) with a phosphitylating reagent, for example, using 2-cyanoethyl-N,N-diisopropylchlorophosphoramidite under conditions suitable for isolating 5'-O-dimethoxytrityl-2'-deoxy-2'-N-phthaloyl-N4-acetyl cytidine 3'-O-(2-cyanoethyl-N, N-diisopropylphosphoramidite).

In another embodiment, the displacement of the leaving group can occur in the presence of a hindered base. For example, phthalimide can be used in combination with DBU (1,8-Diazabicyclo[5.4.0]undec-7-ene), DBN (1,5-Diazabicyclo[4.3.0]non-5-ene), Dabco (1,4-Diazabicyclo[2.2.2]octane), and/or 2-tert-Butylimino-2-diethylamino-1,3-dimethyl-perhydro-1,3,2-diazaphosphorine or the equivalent thereof to yield 5',3'-di-O-tetraisopropyldisiloxy-2'-deoxy-2'-N-phthaloyl cytidine or 5',3'-O-di-tert-butylsilanediyl-2'-deoxy-2'-N-phthaloyl cytidine In another embodiment, the invention provides a method for the synthesis of a 2'-deoxy-2'-N-phthaloyl uridine phosphoramidite. For example, the present invention provides a method for synthesizing 5'-O-dimethoxytrityl-2'-deoxy-2'-N-phthaloyl uridine 3'-O-(2-cyanoethyl-N,N-diisopropylphosphoramidite), comprising the steps of:

(1) introducing protection of the 5'-hydroxyl and 3'-hydroxyl groups of a 1-β-D-arabinofuranosyl uracil, for example, using cyclic silylation with 1,3-dichloro-1,1,3,3-tetraisopropyldisiloxane or di-tert-butylsilylbis(trifluoromethanesulfonate) under conditions suitable for the isolation of 5',3'-di-O-tetraisopropyldisiloxy-1-β-D-arabinofuranosyl uracil or 5',3'-O-di-tert-butylsilanediyl-1-β-D-arabinofuranosyl uracil, (2) introducing a leaving group at the 2'-position of the product of step (1), for example using triflic anhydride or triflyl chloride in the presence of dimethylaminopyridine (DMAP) and/or pyridine under conditions suitable for obtaining 5',3'-di-O-tetraisopropyldisiloxy-2'-trifluoromethanesulfonyl-1-β-D-arabinofuranosyl uracil or 5',3'-O-di-tert-butylsilanediyl-2'-trifluoromethanesulfonyl-1-β-D-arabinofuranosyl uracil, (3) displacing the leaving group from the product of step (2) with a phthalimide or substituted phthalimide nucleophile, (4) deprotecting the product of step (3) with a source of fluoride ion, for example TEA.3HF, TBAF or the equivalent thereof for the selective removal of 5',3'-di-O-tetraisopropyldisiloxane or 5',3'-O-di-tert-butylsilanediyl protection under conditions suitable for the isolation of 2'-deoxy-2'-N-phthaloyl uridine, (5) introducing a 5'-hydroxyl protecting group compatible with oligonucleotide synthesis to the product of step (4), for example, by using 4'-4'-dimethoxytrityl chloride under conditions suitable for obtaining 5'-O-dimethoxytrityl-2'-deoxy-2'-N-phthaloyl uridine, and (6) introducing a phosphoramidite moiety at the 3'-position of the product of step (5) with a phosphitylating reagent, for example using 2-cyanoethyl-N,N-diisopropylchlorophosphoramidite under conditions suitable for isolating 5'-O-dimethoxytrityl-2'-deoxy-2'-N-phthaloyl uridine 3'-O-(2-cyanoethyl-N,N-diisopropylphosphoramidite).

In one embodiment, the displacement of the leaving group can occur in the presence of a hindered base. For example phthalimide can be used in combination with DBU (1,8-Diazabicyclo[5.4.0]undec-7-ene), DBN (1,5-Diazabicyclo[4.3.0]non-5-ene), Dabco (1,4-Diazabicyclo[2.2.2]octane), and/or 2-tert-Butylimino-2-diethylamino-1,3-dimethylperhydro-1,3,2-diazaphosphorine or the equivalent thereof to yield 5',3'-di-O-tetraisopropyldisiloxy-2'-deoxy-2'-N-phthaloyl uridine or 5',3'-O-di-tert-butylsilanediyl-2'-deoxy-2'-N-phthaloyl uridine, In another embodiment, the invention provides a method for the chemical synthesis of a 2'-deoxy-2'-N-phthaloyl adenosine phosphoramidite. For example, the present invention provides a method for synthesizing 5'-O-dimethoxytrityl-2'-deoxy-2'-N-phthaloyl-N6-benzoyl adenosine 3'-O-(2-cyanoethyl-N,N-diisopropylphosphoramidite), comprising the steps of:

(1) introducing an acyl group at the $N^6$ position of 1-β-D-arabinofuranosyl adenine with an acylating agent, for example, using benzoyl chloride under conditions suitable for obtaining 1-β-D-arabinofuranosyl-N6-benzoyl adenine, (2) introducing protection of the 5'-hydroxyl and 3'-hydroxyl groups of the product from step (a), for example using cyclic silylation with 1,3-dichloro-1,1,3,3-tetraisopropyldisiloxane or di-tert-butylsilylbis(trifluoromethanesulfonate) under conditions suitable for the isolation of 5',3'-di-O-tetraisopropyldisiloxy-1-β-D-arabinofuranosyl-N6-benzoyl adenine or 5',3'-O-di-tert-butylsilanediyl-1-β-D-arabinofuranosyl-N6-benzoyl adenine, (3) introducing a leaving group at the 2'-position of the product of step (2), for example, using triflic anhydride or triflyl chloride in the presence of dimethylaminopyridine (DMAP) and/or pyridine under conditions suitable for obtaining 5',3'-di-O-tetraisopropyldisiloxy-2'-trifluoromethanesulfonyl-1-β-D-arabinofuranosyl-N6-benzoyl adenine or 5',3'-O-di-tert-butylsilanediyl-2'-trifluoromethanesulfonyl-1-β-D-arabinofuranosyl-N6-benzoyl adenine, (4) displacing the leaving group from the product of step (3) with a phthalimide or substituted phthalimide nucleophile, (5) deprotecting the product of step (4) with a source of fluoride ion, for example, TEA.3HF, TBAF or the equivalent thereof for the selective removal of 5',3'-di-O-tetraisopropyldisiloxane or 5',3'-O-di-tert-butylsilanediyl protection under conditions suitable for the isolation of 2'-deoxy-2'-N-phthaloyl-N6-benzoyl adenosine, (6) introducing a 5'-hydroxyl protecting group compatible with oligonucleotide synthesis to the product of step (5), for example, by using 4'-4'-dimethoxytrityl chloride under conditions suitable for obtaining 5'-O-dimethoxytrityl-2'-deoxy-2'-N-phthaloyl-N6-benzoyl adenosine, and (7) introducing a phosphoramidite moiety at the 3'-position of the product of step (6) with a phosphitylating reagent, for example, using 2-cyanoethyl-N,N-diisopropylchlorophosphoramidite under conditions suitable for isolating 5'-O-dimethoxytrityl-2'-deoxy-2'-N-phthaloyl-N6-benzoyl adenosine 3'-O-(2-cyanoethyl-N,N-diisopropylphosphoramidite).

In one embodiment, the displacement of the leaving group can occur in the presence of a hindered base. For example, phthalimide can be used in combination with DBU (1,8-Diazabicyclo[5.4.0]undec-7-ene), DBN (1,5-Diazabicyclo[4.3.0]non-5-ene), Dabco (1,4-Diazabicyclo[2.2.2]octane), and/or 2-tert-Butylimino-2-diethylamino-1,3-dimethylperhydro-1,3,2-diazaphosphorine or the equivalent thereof to yield 5',3'-di-O-tetraisopropyldisiloxy-2'-deoxy-2'-N-phthaloyl-N6-benzoyl adenosine or 5',3'-O-di-tert-butylsilanediyl-2'-deoxy-2'-N-phthaloyl-N6-benzoyl adenosine In another embodiment, the invention provides another method for synthesizing a 2'-deoxy-2'-N-phthaloyl adenosine phosphoramidite, for example, 5'-O-dimethoxytrityl-2'-deoxy-2'-N-phthaloyl-N6-benzoyl adenosine 3'-O-(2-cyanoethyl-N,N-diisopropylphosphoramidite). This method comprises the steps of:

(1) introducing a protecting group on the 5'-hydroxyl and 3'-hydroxyl groups of a 1-β-D-arabinofuranosyl adenine, for example, using cyclic silylation with 1,3-dichloro-1,1,3,3-tetraisopropyldisiloxane or di-tert-butylsilylbis(trifluoromethanesulfonate) under conditions suitable for the isolation of 5',3'-di-O-tetraisopropyldisiloxy-1-β-D-arabinofuranosyl adenine or 5',3'-O-di-tert-butylsilanediyl-1-β-D-arabinofuranosyl adenine, (2) introducing a leaving group at the 2'-position of the product of step (1), for example, using triflic anhydride or triflyl chloride in the presence of dimethylaminopyridine (DMAP) and/or pyridine under conditions suitable for obtaining 5',3'-di-O-tetraisopropyldisiloxy-2'-trifluoromethanesulfonyl-1-β-D-arabinofuranosyl adenine or 5',3'-O-di-tert-butylsilanediyl-2'-trifluoromethanesulfonyl-1-β-D-arabinofuranosyl adenine, (3) displacing the leaving group from the product of step (2) with a phthalimide or substituted phthalimide nucleophile, (4) introducing an acyl group at the N6 position of the product from step (3) with an acylating agent, for example, using benzoyl chloride under conditions suitable for obtaining 5',3'-di-O-tetraisopropyldisiloxy-2'-trifluoromethanesulfonyl-1-β-D-arabinofuranosyl-N6- benzoyl adenosine or 5',3'-O-di-tert-butylsilanediyl-2'-trifluoromethanesulfonyl-1-β-D-arabinofuranosyl-N6-benzoyl adenosine, (5) deprotecting the product of step (4) with a source of fluoride ion, for example TEA.3HF, TBAF or the equivalent thereof for the selective removal of 5',3'-di-O-tetraisopropyldisiloxane or 5',3'-O-di-tert-butylsilanediyl protection under conditions suitable for the isolation of 2'-deoxy-2'-N-phthaloyl-N6-benzoyl adenosine, (6) introducing a 5'-hydroxyl protecting group compatible with oligonucleotide synthesis to the product of step (5), for example, by using 4'-4'-dimethoxytrityl chloride under conditions suitable for obtaining 5'-O-dimethoxytrityl-2'-deoxy-2'-N-phthaloyl-N6-benzoyl adenosine, and (7) introducing a phosphoramidite moiety at the 3'-position of the product of step (6) with a phosphitylating reagent, for example, using 2-cyanoethyl-N,N-diisopropylchlorophosphoramidite under conditions suitable for isolating 5'-O-dimethoxytrityl-2'-deoxy-2'-N-phthaloyl-N6-benzoyl adenosine 3'-O-(2-cyanoethyl-N,N-diisopropylphosphoramidite).

In one embodiment, the displacement of the leaving group can take place in the presence of a hindered base. For example, phthalimide can be used in combination with DBU (1,8-Diazabicyclo[5.4.0]undec-7-ene), DBN (1,5-Diazabicyclo[4.3.0]non-5-ene), Dabco (1,4-Diazabicyclo[2.2.2]octane), and/or 2-tert-Butylimino-2-diethylamino-1,3-dimethyl-perhydro-1,3,2-diazaphosphorine or the equivalent thereof to yield 5',3'-di-O-tetraisopropyldisiloxy-2'-deoxy-2'-N-phthaloyl adenosine or 5',3'-O-di-tert-butylsilanediyl-2'-deoxy-2'-N-phthaloyl adenosine In another embodiment, the invention provides a method for synthesizing a 2'-deoxy-2'-N-phthaloyl guanosine phosphoramidite. For example, the present invention provides a method for synthesizing 5'-O-dimethoxytrityl-2'-deoxy-2'-N-phthaloyl-N2-isobutyryl guanosine 3'-O-(2-cyanoethyl-N,N-diisopropylphosphoramidite), comprising the steps of:

(1) introducing an acyl group at the $N^2$ position of 1-β-D-arabinofuranosyl guanine with an acylating agent, for example, using isobutyryl chloride under conditions suitable for obtaining 1-β-D-arabinofuranosyl-N2-isobutyryl guanine, (2) introducing a protecting group on the 5'-hydroxyl and 3'-hydroxyl groups of the product from step (a), for example, using cyclic silylation with 1,3-dichloro-1,1,3,3-tetraisopropyldisiloxane or di-tert-butylsilylbis(trifluoromethanesulfonate) under conditions suitable for the isolation of 5',3'-di-O-tetraisopropyldisiloxy-1-β-D-arabinofuranosyl-N2-isobutyryl guanine or 5',3'-O-di-tert-butylsilanediyl-1-β-D-arabinofuranosyl-N2-isobutyryl guanine, (3) introducing a leaving group at the 2'-position of the product of step (2), for example, using triflic anhydride or triflyl chloride in the presence of dimethylaminopyridine (DMAP) and/or pyridine under conditions suitable for obtaining 5',3'-di-O-tetraisopropyldisiloxy-2'-trifluoromethanesulfonyl-1-β-D-arabinofuranosyl-N2-isobutyryl guanine or 5',3'-O-di-tert-butylsilanediyl-2'-trifluoromethanesulfonyl-1-β-D-arabinofuranosyl-N2-isobutyryl guanine, (4) displacing the leaving group from the product of step (3) with a phthalimide or substituted phthalimide nucleophile, (5) deprotecting the product of step (4) with a source of fluoride ion, for example, TEA.3HF, TBAF or the equivalent thereof, for the selective removal of 5',3'-di-O-tetraisopropyldisiloxane or 5',3'-O-di-tert-butylsilanediyl protection under conditions suitable for the isolation of 2'-deoxy-2'-N-phthaloyl-N2-isobutyryl guanosine, (6) reacting the product of step (5) with 4'-4'-dimethoxytrityl chloride under conditions suitable for obtaining 5'-O-dimethoxytrityl-2'-deoxy-2'-N-phthaloyl-N2-isobutyryl guanosine, and (7) introducing a phosphoramidite moiety at the 3'-position of the product of step (6) with a phosphitylating reagent, for example, using 2-cyanoethyl-N,N-diisopropylchlorophosphoramidite under conditions suitable for isolating 5'-O-dimethoxytrityl-2'-deoxy-2'-N-phthaloyl-N2-isobutyryl guanosine 3'-O-(2-cyanoethyl-N,N-diisopropylphosphoramidite).

In one embodiment, the displacement of the leaving group can take place in the presence of a hindered base. For example, phthalimide can be used in combination with DBU (1,8-Diazabicyclo[5.4.0]undec-7-ene), DBN (1,5-Diazabicyclo[4.3.0]non-5-ene), Dabco (1,4-Diazabicyclo[2.2.2]octane), and/or 2-tert-Butylimino-2-diethylamino-1,3-dimethyl-perhydro-1,3,2-diazaphosphorine or the equivalent thereof to yield 5',3'-di-O-tetraisopropyldisiloxy-2'-deoxy-2'-N-phthaloyl-N2-isobutyryl guanine or 5',3'-O-di-tert-butylsilanediyl-2'-deoxy-2'-N-phthaloyl-N2-isobutyryl guanine In another embodiment, the invention provides another method for synthesizing a 2'-deoxy-2'N-phthanoyl guanosine phosphoramidite, for example, 5'-O-dimethoxytrityl-2'-deoxy-2'-N-phthaloyl-N2-isobutyryl guanosine 3'-O-(2-cyanoethyl-N,N-diisopropylphosphoramidite), comprising the steps of:

(1) introducing a protecting group on the 5'-hydroxyl and 3'-hydroxyl groups of a 1-β-D-arabinofuranosyl guanine, for example, using cyclic silylation with 1,3-dichloro-1,1,3,3-tetraisopropyldisiloxane or di-tert-butylsilylbis(trifluoromethanesulfonate) under conditions suitable for the isolation of 5',3'-di-O-tetraisopropyldisiloxy-1-β-D-arabinofuranosyl guanine or 5',3'-O-di-tert-butylsilanediyl-1-β-D-arabinofuranosyl guanine, (2) introducing a leaving group at the 2'-position of the product of step (1), for example, using triflic anhydride or triflyl chloride in the presence of dimethylaminopyridine (DMAP) and/or pyridine under conditions suitable for obtaining 5',3'-di-O-tetraisopropyldisiloxy-2'-trifluoromethanesulfonyl-1-β-D-arabinofuranosyl guanine or 5',3'-O-di-tert-butylsilanediyl-2'-trifluoromethanesulfonyl-1-β-D-arabinofuranosyl guanine, (3) displacing the leaving group from the product of step (2) with a phthalimide or substituted phthalimide nucleophile, (4) introducing an acyl group at the $N^2$ position of the product from step (3) with an acylating agent, for example, using isobutyryl chloride under conditions suitable for obtaining 5',3'-di-O-tetraisopropyldisiloxy-2'-trifluoromethanesulfonyl-1-β-D-arabinofuranosyl-N2-isobutyryl guanosine or 5',3'-O-di-tert-butylsilanediyl-2'-trifluoromethanesulfonyl-1-β-D-arabinofuranosyl-N2-isobutyryl guanosine, (5) deprotecting the product of step (4) with a source of fluoride ion, for example TEA.3HF, TBAF or the equivalent thereof for the selective removal of 5',3'-di-O-tetraisopropyldisiloxane or 5',3'-O-di-tertbutylsilanediyl protection under conditions suitable for the isolation of 2'-deoxy-2'-N-phthaloyl-N2-isobutyryl guanosine, (6) introducing a 5'-hydroxyl protecting group compatible with oligonucleotide synthesis to the product of step (e), for example, by using 4'-4'-dimethoxytrityl chloride under conditions suitable for obtaining 5'-O-dimethoxytrityl-2'-deoxy-2'-N-phthaloyl-N2-isobutyryl guanosine, and (7) introducing a phosphoramidite moiety at the 3'-position of the product of step (f) with a phosphitylating reagent, for example, using 2-cyanoethyl-N,N-diisopropylchlorophosphoramidite under conditions suitable for isolating 5'-O-dimethoxytrityl-2'-deoxy-2'-N-phthaloyl-N2-isobutyryl guanosine 3'-O-(2-cyanoethyl-N,N-diisopropylphosphoramidite).

In one embodiment, the displacement of the leaving group can take place in the presence of a hindered base. For example, phthalimide can be used in combination with DBU (1,8-Diazabicyclo[5.4.0]undec-7-ene), DBN (1,5-Diazabicyclo[4.3.0]non-5-ene), Dabco (1,4-Diazabicyclo [2.2.2]octane), and/or 2-tert-Butylimino-2-diethylamino-1, 3-dimethyl-perhydro-1,3,2-diazaphosphorine or the equivalent thereof to yield 5',3'-di-O-tetraisopropyldisiloxy-2'-deoxy-2'-N-phthaloyl guanosine or 5',3'-O-di-tert-butylsilanediyl-2'-deoxy-2'-N-phthaloyl guanosine In preferred embodiments, acylation can follow protection of the 5'-hydroxyl and 3'-hydroxyl groups of the 1-β-D-arabinofuranosyl nucleoside in the chemical synthesis of 2'-deoxy-2'-N-phthaloyl cytidine nucleosides and nucleoside phosphoramidites, 2'-deoxy-2'-N-phthaloyl adenosine nucleosides and nucleoside phosphoramidites, and 2'-deoxy-2'-N-phthaloyl guanosine nucleosides and nucleoside phosphoramidites contemplated by the methods of the instant invention.

In additional embodiments, O6 protection of 1-β-D-arabinofuranosyl guanine can be effected either prior to or after acylation in the chemical synthesis of 2'-deoxy-2'-N-phthaloyl guanosine nucleosides and nucleoside phosphoramidites and equivalents thereof contemplated by the methods of the instant invention, by using an O6 protecting group, such as a nitrophenyl or diphenylcarbamoyl group.

In a further embodiment, N2 protection of 1-β-D-arabinofuranosyl guanine can be effected with dimethylformamide (DMF) protection.

Preferably, in any of the above embodiments, the substituted phthalimide nucleophile is 4,5-dichlorophthalimide, 3,4,5,6-tetrachlorophthalimide, 3-nitrophthalimide, or 4-nitrophthalimide.

In another aspect of the present invention, methods for the preparation of 2'-O-silyl-nucleosides and 2'-O-silylnucleoside phosphoramidites are provided. The methods can be scaled up to kilogram or greater quantities.

In one embodiment, the method for synthesizing a 2'-O-silylnucleoside phosphoramidite comprises the steps of:

(1) introducing a 5',3'-cyclic silyl protecting group to a nucleoside, which can be a D- or L-nucleoside, for example, by using a disilylalkyl bis(trifluoromethanesulfonate) to form a 5',3'-O-(di-alkylsilanediyl) nucleoside, (2) introducing a 2'-O-silyl protecting group via selective formation of a 2'-O-silyl ether, for example, by treatment of the product from step (1) with a substituted silyl chloride and/or silyl triflate, such as tert-butyldimethylsilyl chloride and tert-butyldimethylsilyl triflate, to form a 5',3'-O-(di-alkylsilanediyl)-2'-O-silyl nucleoside, (3) introducing nucleic acid base protection where necessary to the product of step (2), for example, by treatment of a 5',3'-O-(di-alkylsilanediyl)-2'-O-silyl nucleoside with an acyl-chloride or acyl-anhydride, (4) selectively desilylating the 5',3'-cyclic silyl ether from the product of step (3), for example, by treating the 5',3'-O-(di-alkylsilanediyl)-2'-O-silyl nucleoside with a source of fluoride ion, such as pyridine/HF, to obtain a 2'-O-silyl-nucleoside, such as a 2'-O-tert-butyldimethylsilyl nucleoside, (5) introducing a 5'-hydroxyl protecting group compatible with oligonucleotide synthesis to the product of step (4), for example, by using 4'-4'-dimethoxytrityl chloride under conditions suitable for obtaining a 5'-O-dimethoxytrityl-2'-O-tert-butyldimethylsilyl nucleoside, (6) introducing a phosphoramidite moiety at the 3'-position of the product of step (5) with a phosphitylating reagent, for example, using 2-cyanoethyl-N,N-diisopropylchlorophosphoramidite under conditions suitable for isolating a 5'-O-dimethoxytrityl-2'-O-tert-butyldimethylsilyl nucleoside 3'-O-(2-cyanoethyl-N,N-diisopropylphosphoramidite).

In one embodiment, the invention provides a method for synthesizing a 2'-O-silyl-nucleoside phosphoramidite comprising the steps of (1) introducing nucleic acid base protection where necessary to a nucleoside, which can be a D or L nucleoside, for example by treating the nucleoside with an acyl-chloride or acyl-anhydride, (2) introducing a 5',3'-cyclic silyl protecting group to the product of step (1), for example by using a disilylalkyl bis(trifluoromethanesulfonate) to form a 5',3'-O-(di-alkylsilanediyl) nucleoside, (3) introducing a 2'-O-silyl protecting group via selective formation of a 2'-O-silyl ether, for example by treatment of the product from step (2) with a substituted silyl chloride and/or silyl triflate such as tert-butyldimethylsilyl chloride and tert-butyldimethylsilyl triflate, to form a 5',3'-O-(di-alkylsilanediyl)-2'-O-silyl nucleoside, (4) selectively desilylating the 5',3'-cyclic silyl ether from the product of step (3), for example by treating the 5',3'-O-(di-alkylsilanediyl)-2'-O-silyl nucleoside with a source of fluoride ion, such as pyridine/HF, to obtain a 2'-O-silyl-nucleoside such as a 2'-O-tert-butyldimethylsilyl nucleoside, (5) introducing a 5'-hydroxyl protecting group compatible with oligonucleotide synthesis to the product of step (4), for example, by using 4'-4'-dimethoxytrityl chloride under conditions suitable for obtaining a 5'-O-dimethoxytrityl-2'-O-tert-butyldimethylsilyl nucleoside, and (6) introducing a phosphoramidite moiety at the 3'-position of the product of step (5) with a phosphitylating reagent, for example, using 2-cyanoethyl-N,N-diisopropylchlorophosphoramidite under conditions suitable for isolating a 5'-O-dimethoxytrityl-2'-O-tert-butyldimethylsilyl nucleoside 3'-O-(2-cyanoethyl-N,N-diisopropylphosphoramidite).

In a preferred embodiment, the invention provides a method for synthesizing a 2'-O-silyl cytidine phosphoramidite, for example, 5'-O-dimethoxytrityl-2'-O-tert-butyldimethylsilyl-N4-acetyl cytidine 3'-O-(2-cyanoethyl-N,N-diisopropylphosphoramidite), comprising the steps of:

(1) introducing an acyl group at the $N^4$ position of cytidine with an acylating agent, for example, using acetic anhydride under conditions suitable for obtaining N4-acetyl cytidine, (2) introducing protection of the 5'-hydroxyl and 3'-hydroxyl groups of the product from step (1), for example, using cyclic silylation with di-tert-butylsilylbis(trifluoromethanesulfonate) under conditions suitable for the isolation of 5',3'-O-di-tert-butylsilanediyl-N4-acetyl cytidine, (3) introducing a silyl protecting group at the 2'-position of the product of step (2), for example, using tert-butyldimethylsilyl chloride in the presence of imidazole and/or silver nitrate under conditions suitable for obtaining 5',3'-O-di-tert-butylsilanediyl-2'-O-tert-butyldimethylsilyl-N4-acetyl cytidine, (4) deprotecting the product of step (3) with a source of fluoride ion, for example, hydrogen fluoride-pyridine, tributylamine-hydrogen fluoride or the equivalent thereof for the selective removal of 5',3'-O-di-tert-butylsilanediyl protection under conditions suitable for the isolation of 2'-O-tert-butyldimethylsilyl-N4-acetyl cytidine, (5) introducing a 5'-hydroxyl protecting group compatible with oligonucleotide synthesis to the product of step (4), for example by using 4'-4'-dimethoxytrityl chloride under conditions suitable for obtaining 5'-O-dimethoxytrityl-2'-O-tert-butyldimethylsilyl-N4-acetyl cytidine, and (6) introducing a phosphoramidite moiety at the 3'-position of the product of step (5) with a phosphitylating reagent, for example using 2-cyanoethyl-N,N-diisopropylchlorophosphoramidite under conditions suitable for isolating 5'-O-dimethoxytrityl-2'-O-tert-butyldimethylsilyl-N4-acetyl cytidine 3'-O-(2-cyanoethyl-N,N-diisopropylphosphoramidite).

In another embodiment, the invention provides a method for synthesizing a 2'-O-silyl cytidine phosphoramidite, for example 5'-O-dimethoxytrityl-2'-O-tert-butyldimethylsilyl-N4-acetyl cytidine 3'-O-(2-cyanoethyl-N,N-diisopropylphosphoramidite), comprising the steps of:

(1) introducing protection of the 5'-hydroxyl and 3'-hydroxyl groups of cytidine, for example using cyclic silylation with di-tert-butylsilylbis (trifluoromethanesulfonate) under conditions suitable for the isolation of 5',3'-O-di-tert-butylsilanediyl cytidine, (2) introducing a silyl protecting group at the 2'-position of the product of step (1), for example, using tert-butyldimethylsilyl chloride in the presence of imidazole and/or silver nitrate under conditions suitable for obtaining 5',3'-O-di-tert-butylsilanediyl-2'-O-tert-butyldimethylsilyl cytidine, (3) introducing an acyl group at the $N^4$ position of the product from step (2) with an acylating agent, for example using acetyl chloride under conditions suitable for obtaining 5',3'-O-di-tert-butylsilanediyl-2'-O-tert-butyldimethylsilyl-N4-acetyl cytidine, (4) deprotecting the product of step (3) with a source of fluoride ion, for example hydrogen fluoride-pyridine, tributylamine-hydrogen fluoride or the equivalent thereof for the selective removal of 5',3'-O-di-tert-butylsilanediyl protection under conditions suitable for the isolation of 2'-O-tert-butyldimethylsilyl-N4-acetyl cytidine, (5) introducing a 5'-hydroxyl protecting group compatible with oligonucleotide synthesis to the product of step (4), for example, by using 4'-4'-dimethoxytrityl chloride under conditions suitable for obtaining 5'-O-dimethoxytrityl-2'-O-tert-butyldimethylsilyl-N4-acetyl cytidine, and (6) introducing a phosphoramidite moiety at the 3'-position of the product of step (5) with a phosphitylating reagent, for example, using 2-cyanoethyl-N,N-diisopropylchlorophosphoramidite under conditions suitable for isolating 5'-O-dimethoxytrityl-2'-O-tert-butyldimethylsilyl-N4-acetyl cytidine 3'-O-(2-cyanoethyl-N,N-diisopropylphosphoramidite).

In another embodiment, the invention provides a method for synthesizing a 2'-O-silyl uridine phosphoramidite, for example, 5'-O-dimethoxytrityl-2'-O-tert-butyldimethylsilyl uridine 3'-O-(2-cyanoethyl-N,N-diisopropylphosphoramidite), comprising the steps of:

(1) introducing protection of the 5'-hydroxyl and 3'-hydroxyl groups of uridine, for example, using cyclic silylation with di-tert-butylsilylbis (trifluoromethanesulfonate) under conditions suitable for the isolation of 5',3'-O-di-tert-butylsilanediyl uracil, (2) introducing a silyl protecting group at the 2'-position of the product of step (1), for example, using tert-butyldimethylsilyl chloride in the presence of imidazole and/or silver nitrate under conditions suitable for obtaining 5',3'-O-di-tert-butylsilanediyl-2'-O-tert-butyldimethylsilyl uridine, (3) deprotecting the product of step (2) with a source of fluoride ion, for example, hydrogen fluoride-pyridine, tributylamine-hydrogen fluoride or the equivalent thereof for the selective removal of 5',3'-O-di-tert-butylsilanediyl protection under conditions suitable for the isolation of 2'-O-tert-butyldimethylsilyl uridine, (4) introducing a 5'-hydroxyl protecting group compatible with oligonucleotide synthesis to the product of step (3), for example, by using 4'-4'-dimethoxytrityl chloride under conditions suitable for obtaining 5'-O-dimethoxytrityl-2'-O-tert-butyldimethylsilyl uridine, and (5) introducing a phosphoramidite moiety at the 3'-position of the product of step (4) with a phosphitylating reagent, for example, using 2-cyanoethyl-N,N-diisopropylchlorophosphoramidite under conditions suitable for isolating 5'-O-dimethoxytrityl-2'-O-tert-butyldimethylsilyl uridine 3'-O-(2-cyanoethyl-N,N-diisopropylphosphoramidite).

In another embodiment, the invention provides a method for synthesizing a 2'-O-silyl adenosine phosphoramidite, for example, 5'-O-dimethoxytrityl-2'-O-tert-butyldimethylsilyl-N6-benzoyl adenosine 3'-O-(2-cyanoethyl-N,N-diisopropylphosphoramidite), including the steps of:

(1) introducing protection of the 5'-hydroxyl and 3'-hydroxyl groups of adenosine, for example using cyclic silylation with di-tert-butylsilylbis (trifluoromethanesulfonate) under conditions suitable for the isolation of 5',3'-O-di-tert-butylsilanediyl adenosine, (2) introducing a silyl protecting group at the 2'-position of the product of step (1), for example, using tert-butyldimethylsilyl chloride in the presence of imidazole and/or silver nitrate under conditions suitable for obtaining 5',3'-O-di-tert-butylsilanediyl-2'-O-tert-butyldimethylsilyl adenosine, (3) introducing an acyl group at the N6 position of the product from step (2) with an acylating agent, for example, using benzoyl chloride under conditions suitable for obtaining 5',3'-O-di-tert-butylsilanediyl-2'-O-tert-butyldimethylsilyl-N6-benzoyl adenosine, (4) deprotecting the product of step (3) with a source of fluoride ion, for example, hydrogen fluoride-pyridine, tributylamine-hydrogen fluoride or the equivalent thereof for the selective removal of 5',3'-O-di-tert-butylsilanediyl protection under conditions suitable for the isolation of 2'-O-tert-butyldimethylsilyl-N6-benzoyl adenosine, (5) introducing a 5'-hydroxyl protecting group compatible with oligonucleotide synthesis to the product of step (4), for example, by using 4'-4'-dimethoxytrityl chloride under conditions suitable for obtaining 5'-O-dimethoxytrityl-2'-O-tert-butyldimethylsilyl-N6-benzoyl adenosine, and (6) introducing a phosphoramidite moiety at the 3'-position of the product of step (5) with a phosphitylating reagent, for example, using 2-cyanoethyl-N,N-diisopropylchlorophosphoramidite under conditions suitable for isolating 5'-O-dimethoxytrityl-2'-O-tert-butyldimethylsilyl-N6-benzoyl adenosine 3'-O-(2-cyanoethyl-N,N-diisopropylphosphoramidite).

In one embodiment, the invention features a method for synthesizing a 2'-O-silyl guanosine phosphoramidite, for example, 5'-O-dimethoxytrityl-2'-O-tert-butyldimethylsilyl-N2-isobutyryl guanosine 3'-O-(2-cyanoethyl-N,N-diisopropylphosphoramidite), comprising the steps of:

(1) introducing protection of the 5'-hydroxyl and 3'-hydroxyl groups of guanosine, for example, using cyclic silylation with di-tert-butylsilylbis(trifluoromethanesulfonate) under conditions suitable for the isolation of 5',3'-O-di-tert-butylsilanediyl guanosine, (2) introducing a silyl protecting group at the 2'-position of the product of step (1), for example, using tert-butyldimethylsilyl chloride in the presence of imidazole and/or silver nitrate under conditions suitable for obtaining 5',3'-O-di-tert-butylsilanediyl-2'-O-tert-butyldimethylsilyl guanosine, (3) introducing an acyl group at the N2 position of the product from step (2) with an acylating agent, for example, using isobutyryl chloride under conditions suitable for obtaining 5',3'-O-di-tert-butylsilanediyl-2'-O-tert-butyldimethylsilyl-N2-isobutyryl guanosine, (4) deprotecting the product of step (3) with a source of fluoride ion, for example, hydrogen fluoride-pyridine, tributylamine-hydrogen fluoride or the equivalent thereof for the selective removal of 5',3'-O-di-tert-butylsilanediyl protection under conditions suitable for the isolation of 2'-O-tert-butyldimethylsilyl-N2-isobutyryl guanosine, (5) introducing a 5'-hydroxyl protecting group compatible with oligonucleotide synthesis to the product of step (4), for example by using 4'-4'-dimethoxytrityl chloride under conditions suitable for obtaining 5'-O-dimethoxytrityl-2'-O-tert-butyldimethylsilyl-N2-isobutyryl guanosine, and (6) introducing a phosphoramidite moiety at the 3'-position of the product of step (5) with a phosphitylating reagent, for example, using 2-cyanoethyl-N,N-diisopropylchlorophosphoramidite under conditions suitable for isolating 5'-O-dimethoxytrityl-2'-O-tert-butyldimethylsilyl-N2-isobutyryl guanosine 3'-O-(2-cyanoethyl-N,N-diisopropylphosphoramidite).

In preferred embodiments, the synthesis of 2'-deoxy-2'-amino and 2'-deoxy-2'-N-phthaloyl nucleoside analogs contemplated by the instant invention is not limited to adenosine, cytidine, uridine, and guanosine nucleosides and their corresponding L-isomers, but can encompass any number of nucleoside or C-nucleoside analogs, including but not limited to ribothymidine nucleoside, inosine nucleoside, purine nucleoside, 2,6-diaminopurine nucleoside, pyridin-4-one nucleoside, pyridin-2-one nucleoside, phenyl C-nucleosides, pseudouracil nucleosides, 2,4,6-trimethoxy benzene C-nucleosides, 3-methyl uracil nucleosides, dihydrouridine nucleoside, naphthyl C-nucleosides, aminophenyl C-nucleosides, 5-alkylcytidine nucleosides (e.g., 5-methylcytidine), 5-alkyluridine nucleosides (e.g., ribothymidine), 5-halouridine nucleosides (e.g., 5-bromouridine). 6-azapyrimidine nucleosides, 6-alkylpyrimidine nucleosides (e.g. 6-methyluridine), propyne nucleosides, 4'-thio nucleosides, carbocyclic nucleosides, their corresponding L isomers and others.

In additional embodiments, the synthesis of 2-O-silyl nucleosides and 2'-O-silyl C-nucleosides contemplated by the instant invention includes but is not limited to nucleosides selected from the group comprising cytidine, uridine, adenosine, guanosine, inosine, L-cytidine, L-uridine, L-adenosine, L-guanosine, L-inosine, arabino-cytidine, arabino-uridine, arabino-adenosine, arabino-guanosine, arabino-inosine, L-arabino-cytidine, L-arabino-uridine, L-arabino-adenosine, L-arabino-guanosine, L-arabino-inosine, ribo-thymidine, arabino-thymidine, L-ribo-thymidine, and L-arabino-thymidine; C-nucleosides selected from the group comprising phenyl, naphthyl, aminophenyl, and 2,4,6-trimethoxybenzyl C-nucleosides and their corresponding L and arabino isomers.

In another embodiment, the method for synthesis of 2'-O-silyl-nucleosides and 2'-O-silyl-nucleoside phosphoramidites is used for the synthesis of 2'-O-silyl-D-ribofuranosyl nucleosides and 2'-O-silyl-D-ribofuranosyl nucleoside phosphoramidites, 2'-O-silyl-L-ribofuranosyl nucleosides and 2'-O-silyl-L-ribofuranosyl nucleoside phosphoramidites, 2'-O-silyl-D-arabinofuranosyl nucleosides and 2'-O-silyl-D-arabinofuranosyl nucleoside phosphoramidites and both 2'-O-silyl-L-arabinofuranose nucleosides and 2'-O-silyl-L-arabinofuranose nucleoside phosphoramidites.

The present invention also features a synthetic method for the preparation of 2'-O-silyl-C-nucleosides and 2'-O-silylC-nucleoside phosphoramidites. The method can be scaled up to kilogram or greater quantities. The method includes the steps of (1) introducing a 5',3'-cyclic silyl protecting group to a C-nucleoside, which can be a D or L C-nucleoside, for example by using a disilylalkyl bis(trifluoromethanesulfonate) to form a 5',3'-O-(di-alkylsilanediyl) C-nucleoside, and (2) introducing a 2'-O-silyl protecting group via selective formation of a 2'-O-silyl ether, for example by treatment of the product from step (1) with a substituted silyl chloride and/or silyl triflate such as tert-butyldimethylsilyl chloride and tert-butyldimethylsilyl triflate, to form a 5',3'-O-(di-alkylsilanediyl)-2'-O-silyl C-nucleoside, and (3) introducing nucleic acid base protection where necessary to the product of step (2), for example by treatment of a 5',3'-O-(di-alkylsilanediyl)-2'-O-silyl C-nucleoside with an acyl-chloride or acyl-anhydride, and (4) selectively desilylating the 5',3'-cyclic silyl ether from the product of step (3), for example by treating the 5',3'-O-(di-alkylsilanediyl)-2'-O-silyl C-nucleoside with a source of fluoride ion, such as pyridine/HF, to obtain a 2'-O-silyl-C-nucleoside such as a 2'-O-tert-butyldimethylsilyl C-nucleoside, and (5) introducing a 5'-hydroxyl protecting group compatible with oligonucleotide synthesis to the product of step (4), for example by using 4'-4'-dimethoxytrityl chloride under conditions suitable for obtaining a 5'-O-dimethoxytrityl-2'-O-tert-butyldimethylsilyl C-nucleoside, and (6) introducing a phosphoramidite moiety at the 3'-position of the product of step (5) with a phosphitylating reagent, for example using 2-cyanoethyl-N,N-diisopropylchlorophosphoramidite under conditions suitable for isolating a 5'-O-dimethoxytrityl-2'-O-tert-butyldimethylsilyl C-nucleoside 3'-O-(2-cyanoethyl-N,N-diisopropylphosphoramidite).

In one embodiment, the invention features a method for the chemical synthesis of 2'-O-silyl-C-nucleosides and 2'-O-silyl-C-nucleoside phosphoramidites. The method can be scaled up to kilogram or greater quantities. The method includes the steps of (1) introducing nucleic acid base protection where necessary to a C-nucleoside, which can be a D or L C-nucleoside, for example by treating the C-nucleoside with an acyl-chloride or acyl-anhydride; (2) introducing a 5',3'-cyclic silyl protecting group to the product of step (1), for example, by using a disilylalkyl bis(trifluoromethanesulfonate) to form a 5',3'-O-(di-alkylsilanediyl) C-nucleoside; (3) introducing a 2'-O-silyl protecting group via selective formation of a 2'-O-silyl ether, for example by treatment of the product from step (2) with a substituted silyl chloride and/or silyl triflate such as tert-butyldimethylsilyl chloride and tert-butyldimethylsilyl triflate, to form a 5',3'-O-(di-alkylsilanediyl)-2'-O-silyl C-nucleoside; (4) selectively desilylating the 5',3'-cyclic silyl ether from the product of step (3), for example, by treating the 5',3'-O-(di-alkylsilanediyl)-2'-O-silyl C-nucleoside with a source of fluoride ion, such as pyridine/HF, to obtain a 2'-O-silyl-C-nucleoside such as a 2'-O-tert-butyldimethylsilyl C-nucleoside; (5) introducing a 5'-hydroxyl protecting group compatible with oligonucleotide synthesis to the product of step (4), for example, by using 4'-4'-dimethoxytrityl chloride under conditions suitable for obtaining a 5'-O-dimethoxytrityl-2'-O-tert-butyldimethylsilyl C-nucleoside; and (6) introducing a phosphoramidite moiety at the 3'-position of the product of step (5) with a phosphitylating reagent, for example using 2-cyanoethyl-N,N-diisopropylchlorophosphoramidite under conditions suitable for isolating a 5'-O-dimethoxytrityl-2'-O-tert-butyldimethylsilyl C-nucleoside 3'-O-(2-cyanoethyl-N,N-diisopropylphosphoramidite).

In another embodiment, the method for synthesis of 2'-O-silyl-C-nucleosides and 2'-O-silyl-C-nucleoside phosphoramidites is used for the synthesis of 2'-O-silyl-D-ribofuranosyl C-nucleosides and 2'-O-silyl-D-ribofuranosyl C-nucleoside phosphoramidites, 2'-O-silyl-L-ribofuranosyl C-nucleosides and 2'-O-silyl-L-ribofuranosyl C-nucleoside phosphoramidites, 2'-O-silyl-D-arabinofuranosyl C-nucleosides and 2'-O-silyl-D-arabinofuranosyl C-nucleoside phosphoramidites and both 2'-O-silyl-L-arabinofuranose C-nucleosides and 2'-O-silyl-L-arabinofuranose C-nucleoside phosphoramidites.

The present invention also features a practical synthetic method for the preparation of 2'-O-methyl guanosine nucleosides and 2'-O-methyl guanosine nucleoside phosphoramidites. The method can be scaled up to kilogram or greater quantities. The method includes the steps of (1) introducing a 5',3'-cyclic silyl protecting group to a 2,6-diamino-9-(β-ribofuranosyl)purine with a disilylalkyl bis(trifluoromethanesulfonate) to form a 2,6-diamino-9-[5',3'-O-(di-alkylsilanediyl)-β-ribofuranosyl]purine; (2) methylation of a 2,6-diamino-9-[5',3'-O-(di-alkylsilanediyl)-β-ribofuranosyl]purine, for example, by treating the product of step (1) with methyl iodide in the presence of sodium hydride to yield 2,6-diamino-9-[5',3'-O-(di-alkylsilanediyl)-2'-O-methyl-β-ribofuranosyl]purine; (3) introducing acyl protection at the N2 and N6 positions of the product from step (2), for example, by treating 2,6-diamino-9-[5',3'-O-(di-alkylsilanediyl)-2'-O-methyl-β-ribofuranosyl]purine with an acyl chloride or anhydride, such as, isobutyryl chloride, to provide a $N^2$–$N^6$-2,6-diamino-diacyl-9-[5',3'-O-(di-alkylsilanediyl)-2'-O-methyl-β-ribofuranosyl]purine; (4) selectively deacylating position $N^6$ of the product of step (3), for example, by treating 2,6-diamino-$N^2$–$N^6$-diacyl-9-[5',3'-O-(di-alkylsilanediyl)-2'-O-methyl-β-ribofuranosyl]purine with TEA/MeOH to obtain 2,6-diamino-$N^2$-acyl-9-[5',3'-O-(di-alkylsilanediyl)-2'-O-methyl-β-ribofuranosyl]purine; (5) chemically deaminating the N6-amine and desilylating the product of step (4), for example by treating 2,6-diamino-$N^2$-acyl-9-[5',3'-O-(di-alkylsilanediyl)-2'-O-methyl-β-ribofuranosyl]purine with sodium nitrite/acetic acid followed by treatment with a source of fluoride ion, such as HF-pyridine to yield a $N^2$-acyl-2'-O-methyl guanosine; (6) introduction of a 5'-hydroxyl protecting group compatible with oligonucleotide synthesis to the product of step (5), for example, by using 4'-4'-dimethoxytrityl chloride under conditions suitable for obtaining a $N^2$-acyl-5'-O-dimethoxytrityl-2'-O-methyl guanosine; and (7) introduction of a phosphoramidite moiety at the 3'-position of the product of step (6) with a phosphitylating reagent, for example using 2-cyanoethyl-N,N-diisopropylchlorophosphoramidite under conditions suitable for isolating a $N^2$-acyl-5'-O-dimethoxytrityl-2'-O-methyl guanosine 3'-O-(2-cyanoethyl-N,N-diisopropylphosphoramidite).

The present invention also features a practical synthetic method for the preparation of 2'-O-methyl adenosine nucleosides and 2'-O-methyl adenosine nucleoside phosphoramidites. The method can be scaled up to kilogram or greater quantities. The method includes the steps of (1) introducing a 5',3'-cyclic silyl protecting group to adenosine with a disilylalkyl bis(trifluoromethanesulfonate) to form a 5',3'-O-(di-alkylsilanediyl) adenosine; (2) methylation of a 5',3'-O-(di-alkylsilanediyl) adenosine, for example, by treating the product of step (1) with methyl iodide in the presence of sodium hydride to yield 5',3'-O-(di-alkylsilanediyl)-2'-O-methyl adenosine; (3) introducing acyl protection at the N6 position of the product from step (2), for example, by treating 5',3'-O-(di-alkylsilanediyl)-2'-O-methyl adenosine with an acyl chloride or anhydride, such as, benzoyl chloride, to provide a $N^6$-acyl-5',3'-O-(di-alkylsilanediyl)-2'-O-methyl adenosine; (4) desilylating the product of step (3) by treatment with a source of fluoride ion, such as HF-pyridine to yield a $N^6$-acyl-2'-O-methyl adenosine; (5) introduction of a 5'-hydroxyl protecting group compatible with oligonucleotide synthesis to the product of step (4), for example, by using 4'-4'-dimethoxytrityl chloride under conditions suitable for obtaining a $N^6$-acyl-5'-O-dimethoxytrityl-2'-O-methyl adenosine; and (6) introduction of a phosphoramidite moiety at the 3'-position of the product of step (5) with a phosphitylating reagent, for example using 2-cyanoethyl-N,N-diisopropylchlorophosphoramidite under conditions suitable for isolating a $N^6$-acyl-5'-O-dimethoxytrityl-2'-O-methyl adenosine 3'-O-(2-cyanoethyl-N,N-diisopropylphosphoramidite).

The present invention also provides a practical method for the synthesis of 1,4-anhydro-2-deoxy-D-erythro-pentitol phosphoramidites, including 3-O-protected-1,4-anhydro-2-deoxy-D-erythro-pentitol-5-O-phosphoramidites. The method includes the steps of (1) depyrimidination of a 5'-O-protected thymidine derivative under conditions suitable for the isolation of a 5-O-protected-1,4-anhydro-2-deoxy-D-erythro-pentitol; (2) introduction of an acid-labile protecting group at the C3 hyrdoxyl of the 5-O-protected-1,4-anhydro-2-deoxy-D-erythro-pentitol under conditions suitable for the isolation of a 5-O-protected-3-O-protected-1,4-anhydro-2-deoxy-D-erythro-pentitol; (3) selective 5-O-deprotection of the product of step (2) under conditions suitable for the isolation of a 3-O-protected-1,4-anhydro-2-deoxy-D-erythro-pentitol; and (4) introducing a 5-O-phosphoramidite moiety to of the product of step (3) under conditions suitable for the isolation of a 3-O-protected-1,4-anhydro-2-deoxy-D-erythro-pentitol-5-O-phosphoramidite.

The present invention also provides a practical method for the synthesis of 1,4-anhydro-2-deoxy-D-erythro-pentitol succinates, including 3-O-protected-1,4-anhydro-2-deoxy-D-erythro-pentitol-5-O-succinates. The method includes the steps of (1) depyrimidination of a 5'-O-protected thymidine derivative under conditions suitable for the isolation of a 5-O-protected-1,4-anhydro-2-deoxy-D-erythro-pentitol; (2) introduction of an acid-labile protecting group at the C3 hyrdoxyl of the 5-O-protected-1,4-anhydro-2-deoxy-D-erythro-pentitol under conditions suitable for the isolation of a 5-O-protected-3-O-protected-1,4-anhydro-2-deoxy-D-erythro-pentitol; (3) selective 5-O-deprotection of the product of step (2) under conditions suitable for the isolation of a 3-O-protected-1,4-anhydro-2-deoxy-D-erythro-pentitol; and (4) introducing a 5-O-succinate moiety to of the product of step (3) under conditions suitable for the isolation of a 3-O-protected-1,4-anhydro-2-deoxy-D-erythro-pentitol-5-O-succinate.

In one embodiment, the invention features a method for synthesizing a compound of Formula I,

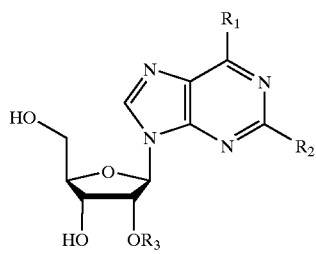

wherein each $R_1$ and $R_2$ independently comprise hydrogen, $NR_{10}R_{11}$, $(NR_{10}R_{11})$alkyl, alkyl, or halogen, wherein $R_{10}$ and $R_{11}$ independently comprise hydrogen, alkyl, alkanoyl, acyl, alkoxy, or arylalkyl optionally substituted with up to three groups independently comprising halogen, alkoxy, nitro, and alkyl, and $R_3$ independently comprises alkyl, alkoxyalkyl, alkyl-thio-alkyl, cyanoalkyl, or arylalkyl optionally substituted with up to three groups that are independently halogen, alkoxy, nitro, or cyanoalkyl, including the steps of: (a) introducing a 5',3'-bridging silyl protecting group to a compound of Formula II;

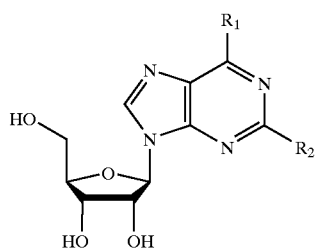

wherein each $R_1$ and $R_2$ is as described in Formula I, to yield a compound of Formula III;

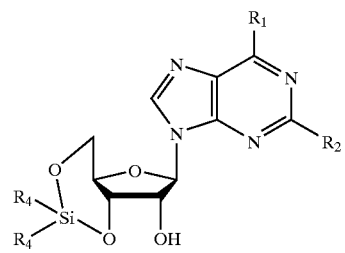

wherein each $R_1$ and $R_2$ is as described in Formula I and each $R_4$ independently comprises an alkyl, aryl or isoalkyl moiety; (b) alkylating the product of step (a) to yield a compound of Formula IV;

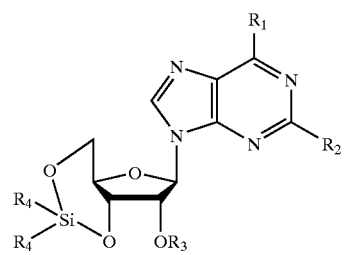

wherein each $R_1$, $R_2$ and $R_3$ is as defined in Formula I and $R_4$ is as defined in Formula III; and (c) deprotecting the product of step (b) to yield a compound of Formula I.

In another embodiment, the invention features a method for synthesizing a compound having Formula V,

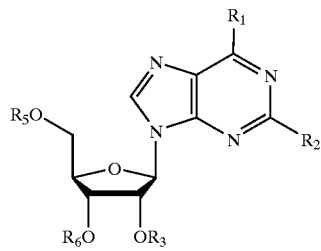

$R_1$ and $R_2$ independently comprise hydrogen, $NR_{10}R_{11}$, $(NR_{10}R_{11})$alkyl, alkyl, or halogen, wherein $R_{10}$ and $R_{11}$ independently comprise hydrogen, alkyl, alkanoyl, acyl, alkoxy, or arylalkyl optionally substituted with up to three groups independently comprising halogen, alkoxy, nitro, and alkyl, and $R_3$ independently comprises alkyl, alkoxyalkyl, alkyl-thio-alkyl, cyanoalkyl, or arylalkyl optionally substituted with up to three groups independently comprising halogen, alkoxy, nitro, and cyanoalkyl, $R_5$ comprises an acid labile protecting moiety and $R_6$ comprises a phosphorous containing moiety including the steps of: (a) introducing a 5',3'-bridging silyl protecting group to a compound of Formula II to yield a compound of Formula III; (b) alkylating the product of step (a) to yield a compound of Formula IV; (c) introducing at least one exocyclic amine protecting moiety to the product of step (b) if $R_1$ or $R_2$ in step (b) independently comprises an amino moiety; (d) deprotecting the product of step (c) to yield a compound of Formula I; and (e) introducing an acid labile protecting moiety followed by a phosphorous containing moiety to the product of step (d) to yield a compound of Formula V.

In another embodiment, $R_4$ of Formulae II and III of the invention comprises a tert-butyl moiety.

In another embodiment, $R_1$ of Formulae I–V of the invention comprises an amino moiety and $R_2$ of Formulae I–V of the invention comprises H.

In another embodiment, $R_1$ and $R_2$ of Formulae I–V of the invention each comprise an amino moiety.

In another embodiment, $R_1$ of Formulae I–V of the invention comprises a chloro moiety and $R_2$ of Formulae I–V of the invention comprises H.

In one embodiment, the compound of Formula I comprises 2'-O-methyl adenosine.

In another embodiment, the compound of Formula V of the invention comprises 5'-O-dimethoxytrityl-2'-O-methyl-N2-benzoyl adenosine 3'-O-(2-cyanoethyl-N,N-diisopropylphosphoramidite).

In another embodiment, alkylation of the instant invention comprises alkylation with methyl iodide and sodium hydride.

In one embodiment, the invention features method for synthesizing a compound having Formula VI,

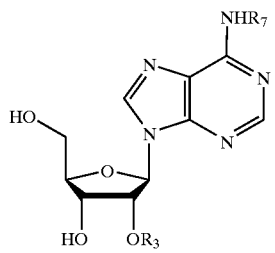

wherein $R_3$ comprises an alkyl, alkoxyalkyl, arylalkyl, alkyl-thio-alkyl, or cyanoalkyl moiety, and $R_7$ comprises an H or acyl moiety, including the steps of: (a) introducing a 5',3'-bridging silyl protecting group to inosine to yield a compound of Formula VII;

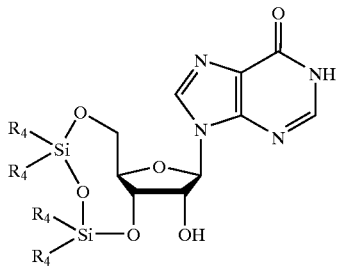

wherein each $R_4$ independently comprises an alkyl, aryl or isoalkyl moiety; (b) introducing an imidazole moiety to the product of step (a) to yield a compound of Formula VIII;

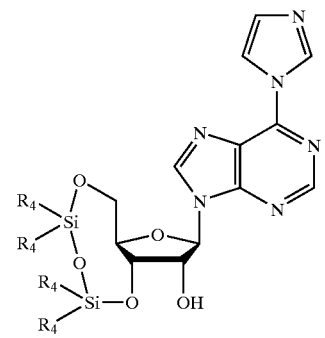

wherein each $R_4$ independently comprises an alkyl, aryl or isoalkyl moiety; (c) alkylating the product of step (b) to yield a compound of Formula IX;

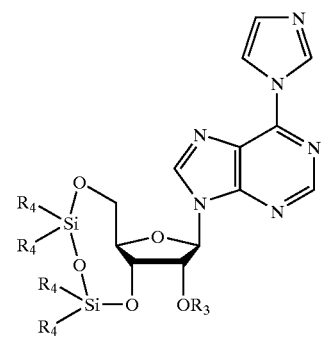

wherein each $R_4$ independently comprises an alkyl, aryl or isoalkyl moiety and $R_3$ is as defined in Formula VI; (d) aminating the product of step (c) to yield a compound of Formula X;

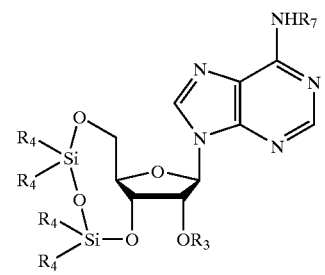

wherein each $R_3$ and $R_7$ is as defined in Formula VI; and (e) desilylating the product of step (d) to yield a compound of Formula VI.

In another embodiment, the invention features a method for synthesizing a 2'-O-alkyl adenosine derivative having Formula VI, including the steps of: (a) introducing a 5',3'-bridging silyl protecting group to inosine to yield a compound of Formula XI;

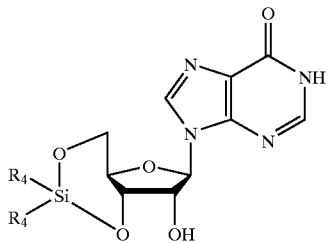

wherein each $R_4$ independently comprises an alkyl, aryl or isoalkyl moiety; (b) introducing an imidazole moiety to the product of step (a) to yield a compound of Formula XII;

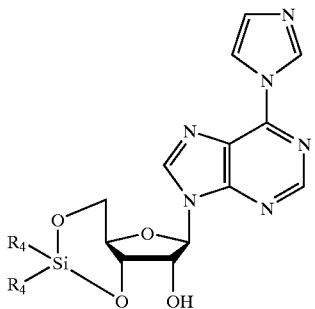

wherein each $R_4$ independently comprises an alkyl, aryl or isoalkyl moiety; (c) alkylating the product of step (b) to yield a compound of Formula XIII;

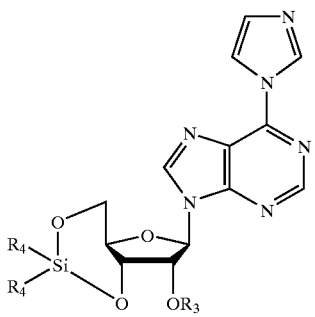

wherein $R_3$ is as defined in Formula VI and each $R_4$ independently comprises an alkyl, aryl or isoalkyl moiety; (d) aminating the product of step (c) to yield a compound of Formula XIV;

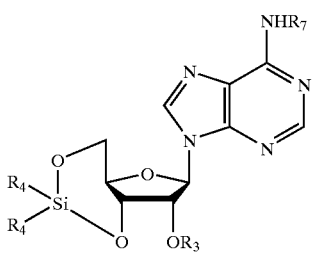

wherein each $R_3$ and $R_7$ is as defined in Formula VI; and (e) desilylating the product of step (d) to yield a compound of Formula VI.

In another embodiment, the invention features a method for the synthesis of a compound having formula XV,

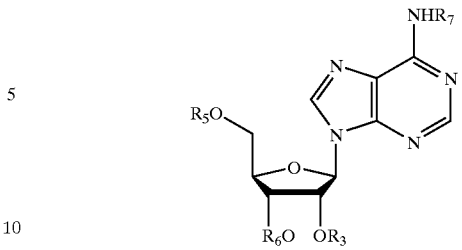

wherein each $R_3$ and $R_7$ is as defined in Formula VI, $R_5$ comprises an acid labile protecting moiety and $R_6$ comprises a phosphorous containing moiety including the step of (a) introducing an acid labile protecting moiety followed by a phosphorous containing moiety to a compound of Formula VI to yield a compound of Formula XV.

In another embodiment, $R_4$ of the instant invention comprises an isopropyl moiety.

In another embodiment, $R_4$ of instant invention comprises a tert-butyl moiety.

In another embodiment, $R_3$ of the instant invention comprises a methyl moiety.

In another embodiment, the compound of Formula VI of the instant invention comprises 2'-O-methyl adenosine.

In another embodiment, $R_7$ of the invention comprises a benzoyl moiety.

In another embodiment, $R_7$ of the invention comprises H.

In another embodiment, the compound of Formula XV of the invention comprises 5'-O-dimethoxytrityl-2'-O-methyl-N2-benzoyl adenosine 3'-O-(2-cyanoethyl-N,N-diisopropylphosphoramidite).

In one embodiment, the invention features a method for synthesizing a compound having Formula XVI,

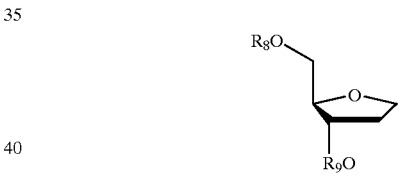

wherein $R_8$ comprises a succinate moiety, silylalkyl moiety, or H, and $R_9$ comprises an acid labile protecting moiety or H, including the steps of: (a) depyrimidination of compound of Formula XVII;

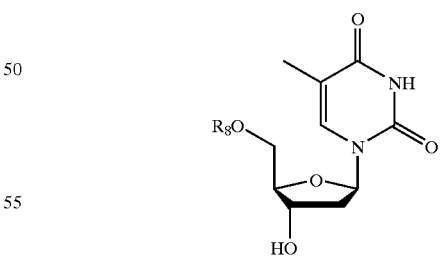

wherein $R_8$ comprises an silylalkyl moiety to yield a compound of Formula XVI, wherein $R_8$ comprises an silylalkyl moiety and $R_9$ comprises H; (b) introducing an acid labile protecting moiety to the product of step (a) to yield a compound of Formula XVI, wherein $R_8$ comprises an silylalkyl moiety and $R_9$ comprises an acid labile protecting moiety; (c) deprotecting the product of step (b) to yield a compound for Formula XVI, wherein $R_8$ comprises H and $R_9$ comprises an acid labile protecting moiety; and (d)

introducing a succinate moiety to the product of step (c) to yield a compound of Formula XVI, wherein $R_8$ comprises a succinate moiety and $R_9$ comprises an acid labile protecting moiety.

In another embodiment, the invention features a method for synthesizing a compound having Formula XVI,

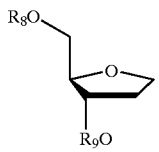

wherein $R_8$ comprises a phosphorous containing moiety, silylalkyl moiety, or H, and $R_9$ comprises an acid labile protecting moiety or H, including the steps of: (a) depyrimidination of compound of Formula XVII;

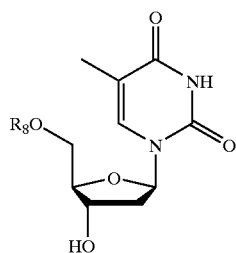

wherein $R_8$ comprises an silylalkyl moiety to yield a compound of Formula XVI, wherein $R_8$ comprises an silylalkyl moiety and $R_9$ comprises H; (b) introducing an acid labile protecting moiety to the product of step (a) to yield a compound of Formula XVI, wherein $R_8$ comprises an silylalkyl moiety and $R_9$ comprises an acid labile protecting moiety; (c) deprotecting the product of step (b) to yield a compound for Formula XVI, wherein $R_8$ comprises H and $R_9$ comprises an acid labile protecting moiety; and (d) introducing a phosphorous containing moiety to the product of step (c) to yield a compound of Formula XVI, wherein $R_8$ comprises a phosphorous containing moiety and Rg comprises an acid labile protecting moiety.

In another embodiment, the silylalkyl moiety $R_8$ of Formulae XVI and XVII of the invention comprises a tert-butyldimethylsilyl, tert-butyldiphenylsilyl, or triisopropylsilyl moiety.

In another embodiment, depyrimidination conditions of the invention comprise treatment of the compound of Formula XVI with a silylating reagent and a catalyst followed by hydrogenation and selective desilyation to yield a compound of Formula XVI, wherein $R_8$ comprises an silylalkyl moiety and $R_9$ comprises H.

In another embodiment, the silylating reagent of the invention used in depryimidination comprises hexamethyldisilazane.

In another embodiment, the catalyst of the invention used in depryimidination comprises sulfuric acid, para-toluene sulfonic acid, and ammonium sulfate.

In another embodiment, the catalyst of the invention used in depryimidination comprises a sulfonic acid, sulfonyl halide, sulfonate or sulfamide, for example, methanesulfonic acid, trifluoromethanesulfonic acid, methanesulfamide, sulfamide, methanesulfonylchloride, or trimethylsilylmethane sulfonate.

In another embodiment, the selective desilylation reaction used in the depyrimidination reaction of the invention comprises treatment with pyridinium trifluoroacetate.

In another embodiment, the hydrogenation reaction used in the depyrimidination step of the method of the invention comprises catalytic hydrogenation with hydrogen gas and palladium on carbon.

In another embodiment, the deprotection conditions of the compound of Formula XVI of the invention, wherein $R_8$ comprises an silylalkyl moiety and Rg comprises an acid labile protecting moiety, comprise treatment with sodium hydroxide in ethanol.

In another embodiment, the compound of Formula XVI of the invention, wherein $R_8$ comprises a succinate moiety and $R_9$ comprises an acid labile protecting moiety, comprises 3-O-dimethoxytrityl-1,4-anhydro-2-deoxy-D-erythro-pentitol-5-O-succinate.

In another embodiment, the compound of Formula XVI of the invention, wherein $R_8$ comprises a phosphoramidite moiety and $R_9$ comprises an acid labile protecting moiety, comprises 3-O-dimethoxytrityl-1,4-anhydro-2-deoxy-D-erythro-pentitol-5-O-(2-cyanoethyl-N,N-diisopropylphosphoramidite).

In one embodiment, the acid labile protecting moiety of the invention comprises a dimethoxytrityl, monomethoxytrityl, or trityl moiety.

In another embodiment, the phosphorous containing moiety of the invention comprises a phosphoramidite moiety.

In another embodiment, the phosphorous containing moiety of the invention comprises a triphosphate moiety.

In another embodiment, the phosphoramidite moiety of the invention comprises a 3'-O-(2-cyanoethyl-N,N-diisopropylphosphoramidite) moiety.

In another embodiment, the amination of compounds of the invention comprises amination with ammonia.

In another embodiment, the amination of compounds of the invention comprises amination with an acylamide.

In another embodiment, the acylamide of the invention is benzamide.

In another embodiment, the 5',3'-bridging silyl protecting group of the invention is introduced using di-tert-butylsilylbis(trifluoromethanesulfonate) in the presence of a base.

In another embodiment, the 5',3'-bridging silyl protecting group of the invention is introduced using 1,3-dichloro-1,1,3,3-tetraisopropyldisiloxane in the presence of a base.

In another embodiment, the base used in introducing the 5',3'-bridging silyl protecting group of the invention comprises triethylamine, diisopropylethylamine, pyridine, collidine, lutidine, 1-methylimidazole, imidazole, N,N-dimethylaminopyridine, or combinations thereof.

In another embodiment, the alkylation of the invention is conducted in the presence of an alkyl halide and a base.

In another embodiment, the alkyl halide used in alkylation of the invention comprises methyl iodide and the base used in alkylation of the invention comprises sodium hydride.

In another embodiment, silyl deprotection of the invention, for example of the 5' and 3' hydroxyls of a nucleoside, is performed using a reagent that comprises an acid, a fluoride source, or a combination thereof, for example HF/pyridine, tetrabutylammonium fluoride, aqueous HF solution, HF gas, or HF/triethylamine adduct.

In one embodiment, the reaction steps of the instant invention are independently performed at a temperature of about −20° C. to about 50° C.

In another embodiment, the phosphorous containing moiety of the invention is introduced with a chlorophosphine and a base.

In another embodiment, the base used in introducing the phosphorous containing moiety of the invention comprises triethylamine, diisopropylethylamine, pyridine, collidine, lutidine, 1-methylimidazole, imidazole, N,N-dimethylaminopyridine, or combinations thereof.

In one embodiment, the invention features a composition of Formula VIII;

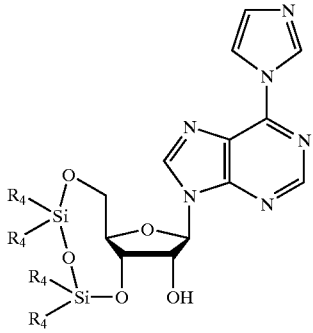

wherein each $R_4$ independently comprises alkyl, aryl or isoalkyl.

In another embodiment, the invention features a composition of Formula IX;

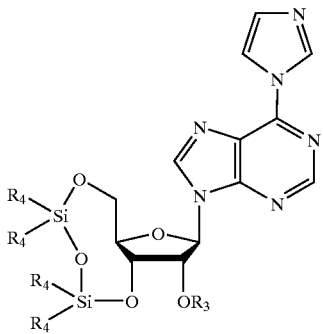

wherein $R_4$ independently comprises alkyl, alkoxyalkyl, alkyl-thio-alkyl, cyanoalkyl, or arylalkyl optionally substituted with up to three groups independently comprising halogen, alkoxy, nitro, and alkyl and each $R_4$ independently comprises alkyl, aryl or isoalkyl.

In one embodiment, the invention features a composition of Formula XII;

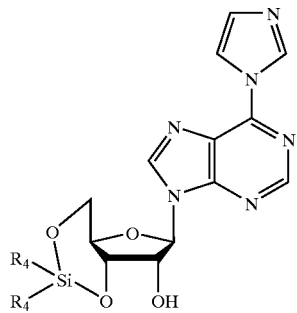

wherein each $R_4$ independently comprises alkyl, aryl or isoalkyl.

In another embodiment, the invention features a composition of Formula XIII;

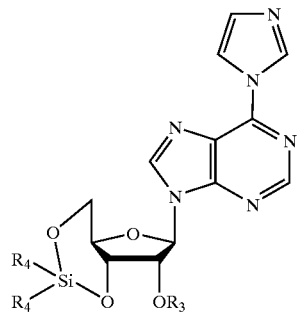

wherein $R_4$ independently comprises alkyl, alkoxyalkyl, alkyl-thio-alkyl, cyanoalkyl, or arylalkyl optionally substituted with up to three groups independently comprising halogen, alkoxy, nitro, and alkyl and each $R_4$ independently comprises alkyl, aryl or isoalkyl.

In one embodiment, $R_4$ of Formulae XIII and IX of the invention comprises isopropyl.

In another embodiment, $R_4$ of Formulae XII and XIII comprises tert-butyl.

In another embodiment, $R_3$ of Formulae IX and XIII comprises methyl. In one embodiment, the conditions suitable for the selective 5-O-deprotection of the 5-O-protected-3-O-protected-1,4-anhydro-2-deoxy-D-erythro-pentitol of the invention comprise the use of sodium hydroxide, for example sodium hydroxide at reflux in ethanol.

In another embodiment, the 3-O-protected-1,4-anhydro-2-deoxy-D-erythro-pentitol-5-O-succinate of the invention is 3-O-dimethoxytrityl-1,4-anhydro-2-deoxy-D-erythro-pentitol-5-O-succinate.

In another embodiment, the 3-O-protected-1,4-anhydro-2-deoxy-D-erythro-pentitol-5-O-phosphoramidite of the invention is 3-O-dimethoxytrityl-1,4-anhydro-2-deoxy-D-erythro-pentitol-5-O-(2-cyanoethyl-N,N-diisopropylphosphoramidite).

In additional embodiments, the methods of the instant invention can be used to synthesize both L and D nucleosides, including but not limited to 2'-O-silyl-β-L-ribofuranosyl nucleosides and 2'-O-silyl-β-L-ribofuranosyl nucleoside phosphoramidites In additional embodiments, the methods of the instant invention can be used to synthesize both L and D nucleosides, including but not limited to 2'-O-silyl-β-L-ribofuranosyl C-nucleosides and 2'-O-silyl-β-L-ribofuranosyl C-nucleoside phosphoramidites The 2'-deoxy-2'-amino, 2'-deoxy-2'-N-phthaloyl, 2'-O-methyl, D-ribo, and L-ribo nucleosides and C-nucleosides and 1,4-anhydro-2-deoxy-D-erythro-pentitol derivatives of the instant invention can be used for chemical synthesis of nucleotides, C-nucleotides, nucleotide-tri-phosphates, C-nucleotide triphosphates and/or nucleoside phosphoramidites and C-nucleoside phosphoramidites as building blocks for selective incorporation into nucleic acid molecules. The incorporation of 2'-deoxy-2'-amino, 2'-deoxy-2'-N-phthaloyl, 2'-O-methyl, D-ribo and L-ribo nucleosides, C-nucleosides, and 1,4-anhydro-2-deoxy-D-erythro-pentitol derivatives into oligonucleotides can serve many purposes, including but not limited to, providing nuclease resistance, improved catalytic activity, and increased functionality compared to molecules lacking such groups. The use of these nucleosides can also provide a useful scaffold for the covalent attachment of additional functional groups, linkers, biomolecules, peptides, proteins, sugars, oligonucleotides, solid supports, small molecules, chemical nucleases and other molecules useful in modulating the desired activity of a nucleic acid molecule. In addition, these nucleic acid molecules can be used as an enzymatic nucleic acid molecule, antisense nucleic acid, 2–5A antisense chimera, decoy nucleic acid molecule, aptamer nucleic acid molecule, triplex forming oligonucleotide, chimeric nucleic acid molecule, agonist nucleic acid molecule, antagonist nucleic acid molecule, or any other nucleic acid molecule species. The forgoing terminology refer to structures and compositions which are well known in the art, and as to which further information is set forth below. Nucleic acid molecules of the instant invention can also be used for purposes including, but not limited to, use as therapeutic agents, diagnostic reagents, and research reagents. Other uses for the nucleic acid molecules include their use as probes or primers for synthesis and/or sequencing of RNA or DNA.

In addition, the 2'-deoxy-2'-amino, 2'-deoxy-2'-N-phthaloyl, 2'-O-methyl, D-ribo, and L-ribo nucleosides, C-nucleosides and nucleoside and C-nucleoside phosphoramidites and 1,4-anhydro-2-deoxy-D-erythro-pentitol derivatives can be used in the synthesis of an enzymatic nucleic acid molecule. For example, these nucleosides can be use in the synthesis of such enzymatic nucleic acid molecules as those having hammerhead, NCH (Inozyme), G-cleaver, amberzyme, zinzyme and/or DNAzyme motifs.

The term "nucleic acid molecule" as used herein refers to a molecule having nucleotides. The nucleic acid can be single, double, or multiple stranded and can comprise modified or unmodified nucleotides or non-nucleotides or various mixtures and combinations thereof.

The term "antisense nucleic acid" as used herein refers to a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review, see Stein and Cheng, 1993 *Science* 261, 1004 and Woolf et al., U.S. Pat. No. 5,849,902). Typically, antisense molecules will be complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, *J. Biol. Chem.*, 274, 21783–21789, Delihas et al., 1997, *Nature*, 15, 751–753, Stein et al., 1997, *Antisense N. A. Drug Dev.*, 7, 151, Crooke, 1998, *Biotech. Genet. Eng. Rev.*, 15, 121–157, Crooke, 1997, *Ad. Pharmacol.*, 40, 1–49. In addition, antisense DNA can be used to target RNA by means of DNA-RNA interactions, thereby activating RNase H, which digests the target RNA in the duplex. Antisense DNA can be synthesized chemically or expressed via the use of a single stranded DNA expression vector or equivalent thereof.

The term "2–5A antisense chimera" as used herein refers to an antisense oligonucleotide containing a 5' phosphorylated 2'-5'-linked adenylate residue. These chimeras bind to target RNA in a sequence-specific manner and activate a cellular 2–5A-dependent ribonuclease which, in turn, cleaves the target RNA (Torrence et al., 1993 *Proc. Natl. Acad. Sci. USA* 90, 1300).

The term "triplex forming oligonucleotide" as used herein refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

The term "enzymatic nucleic acid molecule" as used herein refers to a nucleic acid molecule which has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. Complementarity is preferred to be as high as possible, i.e., up to 100%, but complementarity as low as 50–75% can also be useful in this invention. The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not meant to be limiting and those skilled in the art will recognize that all that is important in an enzymatic nucleic acid molecule of this invention is that it have a specific substrate binding site which is complementary to one or more of the target nucleic acid regions, and that it have nucleotide sequences within or surrounding that substrate binding site which impart a nucleic acid cleaving activity to the molecule (Cech et al., U.S. Pat. No. 4,987,071; Cech et al., 1988, JAMA).

The term "decoy RNA" as used herein refers to an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990, *Cell*, 63, 601–608). This is meant to be a specific example. Those in the art will recognize that this is but one example, and other embodiments can be readily generated using techniques generally known in the art.

The term "agonist RNA" as used herein refers to an RNA molecule that can bind to protein receptors with high affinity and cause the stimulation of specific cellular pathways.

The term "antagonist RNA" as used herein refers to an RNA molecule that can bind to cellular proteins and prevent it from performing its normal biological function (for example, see Tsai et al., 1992 *Proc. Natl. Acad. Sci. USA* 89, 8864–8868).

Examples of enzymatic nucleic acid molecules in which the instant nucleosides can be used include those having hammerhead, NCH or Inozyme, G-cleaver, zinzyme, and/or amberzyme motifs, as well as DNAzymes. All of these structural motifs are described in the art and are thus well-known to skilled artisans. However, a brief description of the structure and relevant art is provided below.

Examples of a "hammerhead" motif are shown in Usman et al., 1996, *Current Opinion in Structural Biology*, 1, 527–533, which is incorporated by reference herein in its entirety including the drawings.

Examples of an "NCH" or "Inozyme" motif are shown in Ludwig et al., U.S. Ser. No. 09/406,643, filed Sep. 27, 1999, entitled "COMPOSITIONS HAVING RNA CLEAVING ACTIVITY", and International PCT publication Nos. WO 98/58058 and WO 98/58057, all incorporated by reference herein in their entirety including the drawings.

Examples of a "G-cleaver" motif are shown in Eckstein et al., International PCT publication No. WO 99/16871, incorporated by reference herein in its entirety including the drawings.

A "zinzyme" motif is a class II enzymatic nucleic acid molecule comprising a motif such as that described in Beigelman et al., International PCT publication No. WO 99/55857, incorporated by reference herein in its entirety including the drawings. Zinzymes represent a non-limiting example of an enzymatic nucleic acid molecule that does not require a ribonucleotide (2'-OH) group within its own nucleic acid sequence for activity.

An "amberzyme" motif is a class I enzymatic nucleic acid molecule comprising a motif such as that described in Beigelman et al., International PCT publication No. WO 99/55857, incorporated by reference herein in its entirety including the drawings. Amberzymes represent a non-limiting example of an enzymatic nucleic acid molecule that does not require a ribonucleotide (2'-OH) group within its own nucleic acid sequence for activity.

The term 'DNAzyme' is meant to refer to an enzymatic nucleic acid molecule that does not require the presence of a ribonucleotide (2'-OH) group within the DNAzyme molecule for its activity. In particular embodiments the enzymatic nucleic acid molecule can have an attached linker(s) or other attached or associated groups, moieties, or chains containing one or more nucleotides with 2'-OH groups. DNAzyme can be synthesized chemically or expressed endogenously in vivo, by means of a single stranded DNA vector or equivalent thereof.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are substantially made of the required elements, and that substantially no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are substantially made of the required elements, but that other elements are optional and may or may not be present depending upon whether or not they affect the activity or action of the listed elements.

Other features and advantages of the invention will be apparent from the following description of the preferred embodiments thereof, and from the claims. The broad scope of this invention is best understood with reference to the following examples, which are not intended to limit the invention to the specific embodiments described below.

EXAMPLE 1

Synthesis of 5'-O-DMT-2'-deoxy-2'-N-phthaloyl-N4-acetyl Cytidine 3'-O-(2-cyanoethyl-N,N-diisopropylphosphoramidite) (8a, R=acetyl), FIG. 3

1-β-D-arabinfuranosyl-N4-acetyl Cytosine (2, R= acetyl (Modified from Bhat, V; et al. 1989, *Nucleosides&Nucleotides*, 8(2), 179–83)

1-β-D-arabinofuranosyl-cytosine (Cytarabine) (1), (25 g, 102.75 mmol, Pfanstiehl Laboratories, Cat. No. C-123, Lot # 2417 B) was co-evaporated with three portions of DMF (120-ml) and then dissolved in anhydrous DMF (250 ml). Acetic anhydride (11.62 ml, 123.30 mmol) was added dropwise with stirring. After stirring for 24 hours at room temperature, TLC (20% MeOH/CH$_2$Cl$_2$) indicated a complete reaction. The reaction was quenched with anhydrous MeOH (25 ml) and DMF was removed by rotary evaporation and co-evaporation three times with toluene. The crude yellow foam was crystallized from a mixture of diethyl ether/methanol (10:1.) The crystallized product was filtered, washed with diethyl ether and dried to give 27.5 g (94%) of desired product (2, R=acetyl).

5',3'-O-tetraisopropyldisiloxy-1-β-D-arabinfuranosyl-N4-acetyl Cytosine (3, R=acetyl)

1-β-D-arabinfuranosyl-N4-acetyl cytosine (2, R=acetyl) (27.00 g, 94.67 mmol) was co-evaporated twice with anhydrous pyridine (250 ml), dissolved in anhydrous pyridine (400 ml) and cooled to 0° C. in an ice/water bath. 1,3-dichloro-1,1,3,3-tetraisopropyldisiloxane (36.34 ml, 113.6 mmol) was added dropwise over 2 hours to the stirred 0° C. reaction mixture. The reaction was equilibrated to room temperature and after two hours a white precipitate of pyridinium hydrochloride was observed. The reaction was subsequently quenched with anhydrous methanol (10 ml) after stirring for five hours (TLC 10% MeOH/CH$_2$Cl$_2$). Pyridine was removed by rotary evaporation and the yellow product was dissolved in CH$_2$Cl$_2$ (400 ml) and washed twice with NaHCO$_3$ (400 ml), dried over sodium sulfate, filtered and evaporated to dryness. The product was crystallized from a mixture of water/EtOH (1:1, 300 ml total volume, plus a few extra drops of EtOH was added to the hot solution to remove cloudiness, the filter should be 60–100 microns). The crystals were dried in vacuum over P$_2$O$_5$ overnight. The total yield of this reaction was 44.2 g (89%).

5',3'-O-tetraisopropyldisiloxy-2'-trifluoromethanesulfonyl-1-β-D-arabinofuranosyl-N4-acetyl Cytosine (4, R=acetyl)

To a solution of 5',3'-O-tetraisopropyldisiloxyl-1-β-D-arabinofuranosyl-N-4-acetyl cytosine (3, R=acetyl) (44 g, 83.23 mmol), DMAP (30.54 g, 250.00 mmol) and pyridine (20.22 ml, 250.00 mmol) stirring at 0° C. under argon in anhydrous dichloromethane (300 ml) was added triflic anhydride (18.20 ml, 108.2 mmol) dropwise via syringe over a 30 minute period. The temperature and speed of addition of triflic anhydride was monitored so as not to allow any exotherm during addition. After stirring at 0° C. for four hours the reaction mixture turned yellowish/orange, TLC (70% EtOAc/CH$_2$Cl$_2$) indicated a complete reaction and the reaction was quenched with anhydrous MeOH (20 ml). Pyridine and DMAP were removed by washing with cold 1.5% acetic acid or citric acid in water (2×1000 ml) followed by aqueous sodium bicarbonate (1000 ml). The organic layer was dried over sodium sulfate, filtered, and the filtrate evaporated in vacuo. The triflate was used without further purification.

5',3'-O-tetraisopropyldisiloxy-2'-deoxy-2'-N-phthaloyl-N4-acetyl Cytidine (5a, R=acetyl)

To a solution of 5',3'-O-tetraisopropyldisiloxyl-1-β-D-arabinofuranosyl-N4-acetyl cytosine-2'-O-triflate (4, R=acetyl) (crude, 29.34 g, 44.45 mmol) and phthalimide (7.85 g, 53.34 mmol) stirring at 0° C. under argon in anhydrous acetonitrile (200 ml) was added DBU (7.96 ml, 53.34 mmol) slowly via syringe. The precipitate does not dissolve until the addition of DBU upon which the reactions turns orange/red with the formation of a white precipitate. The reaction mixture was stirred at room temperature for 24 hours at which time TLC (70% EtOAc/CH$_2$Cl$_2$) indicated complete reaction. The white precipitate was filtered and washed with three portions of acetonitrile (75 ml). The filtrates were combined and evaporated to dryness. The residue was dissolved in 200 ml of dichloromethane and washed with three portions of sodium bicarbonate (3×150). The organic layer was dried over sodium sulfate, filtered, and evaporated to dryness. The resulting foam was dissolved in ethyl acetate and purified via silica gelcolumn chromatography. The residue was then crystallized from toluene/hexanes (1:2) to give the desired product as an off white solid, 18.00 g, 64.5% over two steps.

The major competing side reaction (10–15%) is the formation an elimination product with the double bond between the 1' and 2' carbon (for example, see FIG. 12).

2'-Deoxy-2'-N-phthaloyl-N4-acetyl Cytidine (6a, R=acetyl)

To a solution of 5',3'-O-tetraisopropyldisiloxane-2'-deoxy-2'-N-phthaloyl-N4-acetyl cytidine (5a, R=acetyl) (27.00 g, 41.1 mmol) stirring at 0° C. under argon in anhydrous THF was added TEA.3HF (14.7 ml, 90.41 mmol) dropwise via syringe. The reaction mixture was equilibrated to room temperature and allowed to stir for 4 hours. TLC (20% MeOH/CH$_2$Cl$_2$) indicated a complete reaction, the solvents were removed in vacuo and the reaction mixture was co-evaporated with two portions of THF (200 ml). The resulting white/yellow solid was crystalized from CH$_2$Cl$_2$ containing a minimal amount of methanol to provide 15.0 grams, (88%) of 6a, R=acetyl.

5'-O-DMT-2'-Deoxy-2'-N-phthaloyl-N4-acetyl Cytidine (7a, R=acetyl)

2'-N-phthaloyl-N4-acetyl cytidine (6a, R=acetyl) (14.7 g, 35.5 mmol) was co-evaporated twice with anhydrous pyridine then dissolved in anhydrous pyridine. 4',4'-dimethoxytrityl chloride (15.62 g, 46.10 mmol) was added to the reaction mixture at 0° C. After stirring at 0° C. overnight, TLC (5% EtOH/EtOAc) indicated a complete reaction. The reaction was quenched with 10 ml of anhydrous MeOH and the solvents were removed in vacuo. The residue was dissolved in dichloromethane (500 ml) and washed with two portions of sodium bicarbonate (500 ml) and the organic layer was dried over sodium sulfate, filtered and evaporated to dryness. The residue was crystallized from toluene to give the desired product (7a, R=acetyl), as a white crystalline solid 23.8 g (94%).

5'-O-DMT-2'-deoxy-2'-N-phthaloyl-N4-acetyl Cytidine 3'-O-(2-cyanoethyl-N,N-diisopropylphosphoramidite) (8a, R=acetyl)

To a solution of 5'-DMT-2'-N-phthaloyl-N4-acetyl cytidine (7a, R=acetyl) (26.00 g, 36.35 mmol) stirring at 0° C. under argon in anhydrous dichloromethane (350 ml) was added diisopropylethylamine (DIPEA, 17.73 ml, 101.77 mmol) and 1-methylimidazole (12.90 ml, 36.35 mmol). N,N-diisopropylaminocyanoethyl phosphoramidic chloride (10.53 ml, 47.26 mmol) was added dropwise to the reaction mixture. After four hours at room temperature, TLC (100% EtOAc) indicated a complete reaction. The reaction was quenched with anhydrous MeOH (3 ml) and evaporated to dryness. The residue was purified by flash chromatography utilizing a gradient of 60%–100% EtOAc/hexanes resulting in a 95% yield.

EXAMPLE 2

Synthesis of 5'-O-Dimethoxytrityl-2'-Deoxy-2'-N-phthaloyl-uridine 3'-(2-cyanoethyl-N,N-diisopropyl Phosphoramidite) (16a), FIG. 4

Synthesis of 5',3'-O-(tetraisopropyldisiloxane-1,3-di-yl)-1-β-D-arabinofuranosyl-uracil (11)

1-β-D-arabinofuranosyl-uracil (10) (2.44 g, 10 mmol) was dried by two co-evaporations with anhydrous pyridine and then re-dissolved in anhydrous pyridine. The above solution was cooled (0° C.) and a solution of 1,3-dichloro-1,1,3,3-tetraisopropylsiloxane (3.52 mL, 11.0 mmol) in 10 mL of anhydrous dichloromethane was added dropwise with stirring. After the addition was complete, the reaction mixture was allowed to warm to room temperature and was stirred for an additional two hours. The reaction was then quenched with MeOH (10 mL) and evaporated to dryness. The residue was dissolved in dichloromethane and washed with saturated NaHCO$_3$ and brine, dried over Na$_2$SO$_4$, and filtered. The organic layer was evaporated to dryness and then co-evaporated with toluene to remove traces of pyridine to give 4.8 g (98%) of compound (11) which was used without further purification.

5',3'-O-Tetraisopropyldisiloxy-2'-deoxy-2'-trifluoromethanesulfonyl-1-β-D-arabinofuranosyl-uracil (12)

To a stirred, ice-cooled solution of 5',3'-O-(tetraisopropyldisiloxane-1,3-di-yl)-1-β-D-arabinofuranosyl-uracil (11) (4 g, 8.2 mmol) in anhydrous dichloromethane, trifluoromethane sulfonic anhydride (1.66 mL, 9.86 mmol) was added and the reaction mixture stirred at −5° C. for 30 min. The reaction was then diluted with dichloromethane and washed with cold 1% aq acetic acid, then with saturated aq sodium bicarbonate and brine. The organic layer was dried over anhydrous sodium sulfate, filtered and evaporated to dryness in vacuo. The residue was used in the next step (example 10) without further purification.

5',3'-O-Tetraisopropyldisiloxy-2'-deoxy-2'-N-phthaloyl-uridine (13a)

Was prepared analogously to 5',3'-tetraisopropyldisiloxy-2'-deoxy-2'-N-phthaloyl-N4-acetyl-cytidine from example 1. Yield=65–70%.

2'-Deoxy-2'-N-phthaloyl-uridine (14a)

Was prepared analogously to 2'-deoxy-2'-N-phthaloyl-N4-acetyl-cytidine from example 1. Yield=90%.

Synthesis of 5'-O-Dimethoxytrityl-2'-deoxy-2'-N-phthaloyl-uridine (15a)

Was prepared analogously to 5'-O-dimethoxytrityl-2'-deoxy-2'-N-phthaloyl-N4-acetyl-cytidine from example 1 and purified by flash chromatography using gradient of 5% to 10% acetone in dichloromethane as the eluent. Yield=90%. This purification can be substituted by crystallization from toluene and hexanes.

Synthesis of 5'-O-Dimethoxytrityl-2'-Deoxy-2'-N-phthaloyl-uridine 3'-(2-cyanoethyl-N,N-diisopropyl phosphoramidite) (16a)

Was prepared according to the standard phosphitylation procedure (as described for compound (9) in example 1.

Purification by flash chromatography on silica gel using gradient of 60% to 100% EtOAc in hexanes as the eluent. Yield=85%.

EXAMPLE 3

Synthesis of 5'-O-Dimethoxytrityl-2'-deoxy-2'-N-phthaloyl-N6-tertButylbenzoyl Adenosine-3'-(2-cyanoethyl-N,N-diisopropyl phosphoramidite) (25a, R=t-BuBz), FIG. 5

5',3'-O-tetraisopropyldisiloxy-1-β-D-arabinofuranosyl-adenine (19)

1-β-D-arabinofuranosyl-adenine HCl (18) (5 g, 16.46 mmol, Pfanstiehl Laboratories) was co-evaporated twice from anhydrous pyridine, suspended in anhydrous pyridine (50 ml) and cooled to 0° C. in ice water. 1,3-dichloro-1,1,3,3-tetraisopropyldisiloxane (6.6 ml, 20.23 mmol) was added dropwise to the cold stirred nucleoside solution. After the addition was complete, the reaction mixture was allowed to warm to room temperature and stirred for an additional two hours. The reaction was then quenched with 1 ml of ethanol. Solvents were removed by in vacuo and the residue was dissolved in dichloromethane, washed with saturated sodium bicarbonate solution, dried over sodium sulfate, filtered and evaporated to dryness to give 8.5 g of (19) as a white foam (8.5 g). Product (19) was used without further purification.

5',3'-O-tetraisopropyldisiloxy-2'-trifluoromethanesulfonyl-1-β-D-arabinofuranosyl Adenine (20)

A cold solution (−10° C.) of (19) in anhydrous dichloromethane was treated with trifluoromethanesulfonyl chloride (1.53 mL, 14.4 mmol) for 20 min. The resulting solution was diluted with anhydrous dichloromethane and washed with cold (0° C.) 1% aq acetic acid, then saturated aq NaHCO$_3$ and brine. The organic layer was dried over sodium sulfate, filtered and evaporated to dryness to give derivative (20), which was used without further purification.

5',3'-O-tetraisopropyldisiloxy-2'-deoxy-2'-N-phthaloyl-adenosine (21a)

DBU (2.8 ml, 18.7 mmol.) was added dropwise to a stirred solution of 5',3'-tetraisopropyldisiloxy-1-β-D-arabinofuranosyl adenine-2'-triflate (20) (10 g) and phthalimide (2.52 g, 17.2 mmol) in anhydrous acetonitrile under positive argon pressure. The mixture was stirred at room temperature overnight. The reaction mixture was then evaporated to dryness, dissolved in dichloromethane and washed with saturated aqueous sodium bicarbonate solution and brine. The organic layer was dried over sodium sulfate, filtered and evaporated to dryness in vacuo. The crude material was purified by flash chromatography to yield 5.4 g (51% from 18) of 2'-N-phthaloyl derivative (21a).

5',3'-O-tetraisopropyldisiloxy-2'-deoxy-2'-N-phthaloyl-N6-tertButylbenzoyl Adenosine (22a, R=t-BuBz)

2'-Deoxy-2'-N-phthaloyl derivative (21a) (5.4 g, 8.45 mmol) was dissolved in anhydrous pyridine and 4-tert-butylbenzoyl chloride (1.2 eq) was added at 0° C. and the reaction mixture left overnight at room temperature. The reaction was subsequently quenched with methanol (10 mL), solvents removed in vacuo and the residue dissolved in toluene and evaporated to dryness. The resulting oil was dissolved in dichloromethane, washed with saturated aq. NaHCO$_3$ and brine, dried over sodium sulfate, filtered and evaporated to dryness. The residue was purified by flash chromatography on silica, using EtOAc-Hexanes (1:2) mixture as an eluent to give 5.06 g (75%) of the fully protected synthon (22a, R=t-BuBz).

Synthesis of 2'-Deoxy-2'-N-phthaloyl-N6-tert-Butylbenzoyl Adenosine (23a)

5',3'-Tetraisopropyldisiloxy-2'-deoxy-2'-N-phthaloyl-N2-tertbutylbenzoyl adenosine (22a, R=t-BuBz) (2.4 g, 3.0 mmol) was dissolved in 50 ml of anhydrous THF. Triethylammonium hydrofluoride (1.47 ml, 9.0 mmol) was added and the reaction mixture was stirred overnight at room temperature. The reaction was then quenched with the addition of sodium bicarbonate solution with stirring, extracted with methylene chloride, dried over sodium sulfate, filtered and evaporated to dryness in vacuo. The material was purified by flash chromatography to yield 1.52 g (91%) of 2'-Deoxy-2'-N-phthaloyl-N2-tert-Butylbenzoyl adenosine (23a, R=t-BuBz).

Synthesis of 5'-O-Dimethoxytrityl-2'-deoxy-2'-N-phthaloyl-N6-tert-Butylbenzoyl Adenosine (24a, R=t-BuBz)

Was prepared using standard dimethoxytritylation procedure (as described in example 1). Yield 90%.

5'-O-Dimethoxytrityl-2'-deoxy-2'-N-phthaloyl-N6-tertButylbenzoyl Adenosine-3'-(2-cyanoethyl-N,N-diisopropyl Phosphoramidite) (25a R=t-BuBz)

Was prepared according to the standard phosphitylation procedure (as described for compound 9 in example 1). Purification by flash chromatography on silica gel using gradient of 60% to 100% EtOAc in hexanes as an eluent gave (25a), R=t-BuBz. Yield, 95%.

EXAMPLE 4

Synthesis of 5'-O-dimethoxytrityl-2'-O-tert-butyldimethylsilyl-N4-acetyl Cytidine 3'-O-(2-cyanoethyl-N,N-diisopropylphosphoramidite) (43), FIG. 7

5',3'-di-tert-butylsilanediyl-2'-tert-butyldimethylsilyl-N4-acetyl Cytidine (40)

A suspension of cytidine (38) (2.43 g, 10 mmol) in DMF (20 ml) was treated with methanesulfonic acid (0.71 ml, 11 mmol) at 0° C. Di-tert-butylsilylditriflate (3.6 ml, 11 mmol) was added to the resulting solution and the reaction was stirred 30 min at 0° C. Imidazole (4.08 g, 60 mmol) was then added and the reaction mixture was stirred at room temperature for 30 minutes. Tert-butyldimethylsilyl chloride (1.81 g, 12 mmol) was added and the resulting reaction mixture was heated to 60° C. for 2 hours, cooled to room temperature and the solvent was removed in vacuo. The residue was partitioned between dichloromethane and water. The organic layer was dried over magnesium sulfate, filtered and evaporated to give crude (39) as yellowish oil. The crude (39) was dissolved in dry chloroform (20 ml), and then pyridine (2.5 ml) and acetic anhydride (1.42 ml, 15 mmol) were added. The reaction was allowed to proceed overnight at room temperature, diluted with chloroform (25 ml) and washed with water followed by sodium bicarbonate. The organic layer was dried over magnesium sulfate, filtered and the solvent was removed in vacuo. The residue was crystallized from ethyl acetate to give (40) as colorless crystals, 4.12 g, 76% yield.

5'-O-Dimethoxytrityl-2'-O-tert-butyldimethylsilyl-N4-acetylcytidine (42)

Hydrogen fluoride-pyridine (Aldrich, 0.2 ml, 8 mmol) was carefully diluted with pyridine (1.2 ml) under cooling. The resulting solution was added slowly to a stirred 0° C. suspension of (40) (1.08 g, 2 mmol) in dichloromethane (10 ml) and the reaction was allowed to proceed for 2 hr at 0° C. The reaction mixture was diluted with dichloromethane, washed with water followed by saturated sodium bicarbonate solution. The organic layer was dried over magnesium sulfate, filtered and evaporated to give 0.86 g of crude (41) as white crystals. The latter was dissolved in pyridine (5 ml) and treated with dimethoxytrityl chloride (0.74 g, 2.2 mmol) at 0° C. The reaction mixture was kept at 0° C. overnight, quenched with anhydrous methanol (0.2 ml) and evaporated in vacuo. The residue was partitioned between dichloromethane and water. The organic layer was washed with saturated sodium bicarbonate solution, dried over magnesium sulfate, filtered and the solvent was removed in vacuo. Flash chromatography (gradient 40–60% acetone—hexanes) furnished (42) as white foam, 1.1 g, 78%.

5'-O-Dimethoxytrityl-2'-O-tert-butyldimethylsilyl-N4-acetylcytidine 3'-N,N-diisopropyl(cyanoethyl) phosphoramidite (43)

Compound (43) was obtained as white foam via the standard phosphitylation procedure (as described for compound 9 in example 1) using 2-cyanoethyl-N,N-diisopropylchlorophosphoramidite (2.5 eq), N,N-diisopropylethylamine (4 eq) and 1-methylimidazole (0.5 eq). Yield 84%.

EXAMPLE 5

Synthesis of 5'-O-dimethoxytrityl-2'-O-tert-butyldimethylsilyl uridine 3'-O-(2-cyanoethyl-N,N-diisopropylphosphoramidite) (48) FIG. 8

5',3'-di-tert-butylsilanediyl-2'-O-tert-butyldimethylsilyluridine (45)

Di-tert-butylsilylditriflate (1.8 ml, 5.5 mmol) was added to a solution of uridine (44) (1.22 g, 5 mmol) in DMF (10 ml) and the reaction was stirred 30 min at 0° C. Imidazole (1.7 g, 25 mmol) was added, the reaction mixture was stirred 30 min at room temperature and then treated with tert-butyldimethylsilyl chloride (0.9 g, 6 mmol). After stirring 2 h at 60° C. the solvent was removed in vacuo and the residue was partitioned between dichloromethane and water. The organic layer was dried over magnesium sulfate, filtered and evaporated. The residue was crystallized from acetonitrile to give (45) as white crystals, 1.94 g, 77.9% yield.

5'-O-Dimethoxytrityl-2'-O-tert-butyldimethylsilyluridine (47)

Hydrogen fluoride-pyridine (Aldrich, 0.1 ml, 4 mmol) was carefully diluted with pyridine (0.6 ml) under cooling. The resulting solution was added slowly to a stirred 0° C. solution of (45) (0.5 g, 1 mmol) in dichloromethane (5 ml) and the reaction was allowed to proceed 1 h at 0° C. Then the reaction mixture was diluted with dichloromethane and washed with water followed by saturated sodium bicarbonate solution. The organic layer was dried over magnesium sulfate, filtered and evaporated to give crude (46) as white crystals. The latter was dissolved in pyridine (3 ml) and treated with dimethoxytrityl chloride (0.37 g, 1.1 mmol) at 0° C. The reaction mixture was kept at 0° C. overnight, quenched with anhydrous methanol (0.2 ml) and evaporated in vacuo. The residue was partitioned between dichloromethane and water. The organic layer was washed with saturated sodium bicarbonate solution, dried over magnesium sulfate, filtered and the solvent was removed in vacuo. Flash chromatography (gradient 20–40% ethylacetate-hexane) furnished (47) as a yellowish foam, 0.6 g, 90.9%.

5'-O-Dimethoxytrityl-2'-O-tert-butyldimethylsilyl-N4-acetylcytidine 3'-N,N-diisopropyl(cyanoethyl) phosphoramidite (48)

Compound (48) was obtained as an off white foam via the standard phosphitylation procedure (as described for compound 9 in example 1) using-2-cyanoethyl-N,N-diisopropylchlorophosphoramidite (2.5 eq), N,N-diisopropylethylamine (4 eq) and 1-methylimidazole (0.5 eq). Yield 83%.

EXAMPLE 6

Synthesis of 5'-O-dimethoxytrityl-2'-O-tert-butyldimethylsilyl-N6-benzoyl Adenosine 3'-O-(2-cyanoethyl-N,N-diisopropylphosphoramidite) (54), FIG. 9

5',3'-O-di-tert-Butylsilanediyl-2'-O-tert-butyldimethylsilyl Adenosine (50)

Di-tert-Butylsilylditriflate (3.6 ml, 11 mmol) was added dropwise over 15 min to a stirred suspension of adenosine (10.69 g, 40 mmol) in anhydrous DMF (80 ml) at 0° C. The resulting solution was stirred at 0° C. for 30 min and then imidazole (13.6 g, 200 mmol) and was added in one portion. The mixture was stirred at 0° C. for 5 min and then 25 min at room temperature. The resulting suspension was treated with tert-butyldimethylchlorosilane (7.24 g, 48 mmol). The reaction was allowed to proceed for 2 hr at 60° C. The precipitate disappeared after approximately 45 minutes and after 1 hr crystals of (50) formed. The compound (50) was collected by filtration, washed with cold acetonitrile and then dried in vacuo. Yield 17.89 g (85.7%).

5',3'-O-di-tert-Butylsilanediyl-2'-O-tert-butyldimethylsilyl-N6-benzoyl Adenosine (51)

Benzoyl chloride (8 ml, 68.86 mmol) was added dropwise to a stirred suspension of (50) (17.89 g, 34.28 mmol) in anhydrous pyridine (100 ml) at 0° C. After 5 min the reaction was warmed to room temperature and stirred for 2.5 hr. After that the mixture was cooled to 0° C. and morpholine (12 ml, 137.9 mmol) was added slowly with stirring. After 45 min at 0° C. the reaction mixture was evaporated and the residue was partitioned between methylene chloride and water. The organic layer was dried over sodium sulfate and evaporated in vacuo. Crystallization from acetonitrile (100 ml) furnished (51) as crystalline material. Yield 16.47 g (76.8%).

5'-O-Dimethoxytrityl-2'-O-tert-butyldimethylsilyl-N6-benzoyl Adenosine (53)

Hydrogen fluoride-pyridine (Aldrich, 2.7 ml, 105.3 mmol) was carefully diluted with pyridine (17 ml). The resulting solution was added slowly to a stirred solution of 51 (16.47 g, 26.3 mmol) in anhydrous methylene chloride (130 ml) and the reaction was allowed to proceed for 1 hr at 0° C. The reaction mixture was then washed with water followed by saturated sodium bicarbonate solution. The organic layer was dried over magnesium sulfate, filtered and evaporated in vacuo. To a solution of this material in pyridine (50 ml) was added dimethoxytrityl chloride (9.8 g, 28.93 mmol) and the reaction mixture stirred overnight at 0° C. The reaction was then quenched by addition of anhydrous methanol (0.25 ml) and evaporated in vacuo. The resulting residue was partitioned between methylene chloride and water. The organic layer was washed with saturated sodium bicarbonate solution, dried over magnesium sulfate, filtered and evaporated in vacuo. Flash chromatography on silica using an ethylacetate/hexanes gradient (from 30 to 50%) afforded (53) as white foam. Yield 19.2 g (94.8%).

5'-O-Dimethoxytrityl-2'-O-tert-butyldimethylsilyl-N6-benzoyl Adenosine 3'-N,N-diisopropyl (cyanoethyl)phosphoramidite (54)

Compound (54) was obtained as white foam via the standard phosphitylation procedure (as described for compound 9 in example 1) using 2-cyanoethyl-N,N-diisopropylchlorophosphoramidite (2.5 eq), N,N-diisopropylethylamine (4 eq) and 1-methylimidazole (0.5 eq). Yield 85%.

EXAMPLE 7

Synthesis of 5'-O-dimethoxytrityl-2'-O-tert-butyldimethylsilyl-N2-isobutyryl Guanosine 3'-O-(2-cyanoethyl-N,N-diisopropylphosphoramidite) (60), FIG. 10

5',3'-O-di-tert-butylsilanediyl-2'-O-tert-butyldimethylsilyl guanosine (56)

Anhydrous guanosine (55, 11.33 g, 40 mmol, prepared by drying the monohydrate at 100° C. for 7 hrs in vacuo) was suspended in anhydrous DMF (80 ml) and di-tert-butylsilylditriflate (14.3 ml, 44 mmol) was added dropwise over 15 min with stirring at 0° C. The resulting solution was stirred at 0° C. for 30 min and then imidazole (13.6 g, 200 mmol) was added. The reaction mixture was stirred for 5 min at 0° C. and then at room temperature for 25 min. Tert-Butyldimethylchlorosilane (7.24 g, 48 mmol) was added and reaction was allowed to proceed at 60° C. for 2 hrs. The resulting precipitate of (56) was separated by filtration, washed with cold methanol and dried in vacuo. Yield 18.81 g 25 (87.4%).

5',3'-O-di-tert-butylsilanediyleno-2'-O-tert-butyldimethylsilyl-N2-isobutyryl Guanosine (57)

Isobutyryl chloride (10.4 ml, 100 mmol) was added dropwise to a stirred suspension of (56) (26.89 g, 50 mmol) in anhydrous methylene chloride (100 ml) and pyridine (30 ml) at 0° C. The reaction was left for 3 hr at room temperature, diluted with methanol (40 ml) and cooled on an ice bath. An ethanolic solution of methylamine (8 M, 25 ml, 200 mmol) was added slowly to the reaction mixture. After 30 min the reaction mixture was evaporated to give a slurry that was diluted with methanol (100 ml) and left for 2 hrs at 0° C. The resulting precipitate was filtered, washed with cold methanol and dried in vacuo to give 29.26 g (96.2%) of compound (57).

5'-O-Dimethoxytrityl-2'-O-tert-butyldimethylsilyl-N2-isobutyryl Guanosine (59)

Hydrogen fluoride-pyridine (Aldrich, 4 ml, 154 mmol) was carefully diluted with pyridine (25 ml) under cooling. The resulting solution was added slowly to a stirred 0° C. suspension of (57) (24.36 g, 40 mmol) in anhydrous methylene chloride (200 ml) and the reaction was allowed to proceed for 2 hr at 0° C. The resulting solution was washed with water followed by saturated sodium bicarbonate solution. The organic layer was dried over magnesium sulfate, filtered and evaporated to give crude (58) as semi-crystalline material. The latter was dissolved in pyridine (80 ml) and dimethoxytrityl chloride (14.91 g, 44 mmol) was added at 0° C. The reaction mixture was kept at 0° C. overnight, quenched with anhydrous methanol (0.5 ml) and evaporated in vacuo. The resulting residue was partitioned between methylene chloride and water. The organic layer was washed with saturated sodium bicarbonate solution, dried over magnesium sulfate, filtered and conentrated to afford Crude (59), which was crystallized from dichloromethane (20 ml) and ether (200 ml) to give compound (59) as a white, fine powder. Yield 24.16 g (78.4%).

5'-O-dimethoxytrityl-2'-O-tert-butyldimethylsilyl-N2-isobutyryl Guanosine 3'-O-(2-cyanoethyl-N,N-diisopropylphosphoramidite) (60)

Compound 60 was obtained as white foam via the standard phosphytilation procedure (as described for compound 9 in example 1) using 2-cyanoethyl-N,N-diisopropylchlorophosphoramidite (2.5 eq), N,N-diisopropylethylamine (4 eq) and 1-methylimidazole (0.5 eq). Yield 86%.

EXAMPLE 8

Synthesis of 5'-O-dimethoxytrityl-2'-O-methyl-N2-isobutyryl Guanosine 3'-O-(2-cyanoethyl-N,N-diisopropylphosphoramidite) (69) FIG. 11

2,6-Diamino-9-(3',5'-O-di-tert-butylsilanediyl-β-D-ribofuranosyl)purine (62)

Di-tert-Butylsilylbis(trifluoromethanesulfonate) (17.8 ml, 55 mmol) was added slowly to a stirred at 0° C. suspension of 2,6-diaminopurine riboside (61) (14.11 g, 50 mmol) in 100 ml anhydrous DMF. The resulting solution was stirred 30 min at 0° C. and then imidazole (8.16 g, 120 mmol) was added. The reaction mixture was allowed to proceed for 5 min at 0° C. and then for 30 min at room temperature. The solution was concentrated in vacuo to a slurry that was diluted with methanol (120 ml). Compound (62) was collected by filtration, washed with cold methanol and then dried in vacuo at 60° C. Yield 17.2 g (83.8%).

2,6-Diamino-9-(3',5'-O-di-tert-butylsilanediyl-2'-O-methyl-β-D-ribofuranosyl)purine (63)

To a stirred −20° C. solution of (62) (2.11 g, 5 mmol) in anhydrous DMF (40 ml) methyl iodide (0.93 ml, 15 mmol) was added followed by sodium hydride as a 60% mineral oil suspension (0.3 g, 7.5 mmol). The reaction mixture was stirred for 1.5 h at −20° C. and quenched with ammonium chloride (1.5 g). The resulting suspension was partitioned between chloroform (75 ml) and water (50 ml). The aqueous layer was washed with additional chloroform. The combined chloroform extracts were washed with 50 ml of water and the aqueous layer was extract back with chloroform. The resulting organic solution was dried over magnesium sulfate, filtered and the solvent was removed in vacuo. Crystallization from dichloromethane-hexane mixture (1:1) afforded (63) as colorless crystals. Yield 1.92 g (88%).

2,6-Diamino-N2,N6-di-isobutyryl-9-(3',5'-O-di-tert-butylsilanediyl-2'-O-methyl-β-D-ribofuranosyl) purine (64)

To a stirred suspension of (63) (1.75 g, 4 mmol) in anhydrous pyridine (10 ml) was added isobutyryl chloride (1.04 ml, 2.5 mmol) at 0° C. The reaction mixture was stirred for 2 h at room temperature, quenched with methanol (0.5 ml) end evaporated in vacuo. The resulting residue was partitioned between methylene chloride and water. The organic layer was washed with saturated sodium bicarbonate, dried over sodium sulfate, filtered and the solvent was removed in vacuo. Crystallization from acetonitrile gave 1.95 g of (64) as white crystals, 84.8% yield.

2,6-Diamino-N2-isobutyryl-9-(3',5'-O-di-tert-butylsilanediyl-2'-O-methyl-β-D-ribofuranosyl) purine (65)

A solution of (64) (1.15 g, 2 mmol) in methanol (5 ml) and triethylamine (0.3 ml) was kept for 24 h at room temperature. The resulting precipitate (65) was then filtered, washed with cold methanol and dried in vacuo. Yield 0.9 g (89%).

5',3'-O-di-tert-butylsilanediyl-2'-O-methyl-N2-isobutyryl Guanosine (66)

To a stirred solution of (65) (0.76 g, 1.5 mmol) in a mixture of acetic acid (5 ml), THF (5 ml), dichloromethane (3 ml) and water (1 ml) was added sodium nitrite (0.83 g). After 3 h a second portion of sodium nitrite was added and the stirred reaction mixture was maintained at room temperature for 48 h. The reaction mixture was then partitioned between water and dichloromethane, the organic layer washed with saturated sodium bicarbonate solution, dried over magnesium sulfate, filtered and concentrated in vacuo. Crystallization from ethyl acetate furnished (66) as slightly yellow crystals, 0.65 g, 85% yield.

2'-O-methyl-N2-isobutyryl-guanosine (67)

To a stirred solution of (66) (0.51 g, 1 mmol) in anhydrous dichloromethane (5 ml) was added pyridine (0.5 ml) followed by hydrogen fluoride—pyridine (38.5 M, 0.1 ml). After 15 min the solvent was removed in vacuo. Flash chromatography using a gradient of 5–10% methanol in dichloromethane afforded (67) as white foam, 0.34 g, 93% yield.

5'-O-dimethoxytrityl-2'-O-methyl-N2-isobutyryl Guanosine (68)

Compound (68) was prepared using standard dimethoxytritylation procedure (as described in example 1).

5'-O-dimethoxytrityl-2'-O-methyl-N2-isobutyryl Guanosine 3'-O-(2-cyanoethyl-N,N-diisopropylphosphoramidite) (69)

Compound (69) was prepared according to the standard phosphitylation procedure (as described for compound 9 in example 1). Purification by flash chromatography on silica gel using gradient of 60% to 100% EtOAc in hexanes as the eluent gave (69) as a white foam after evaporation in vacuo.

EXAMPLE 9

Syntheis of 2'-O-methyl-N6-benzoyl Adenosine (75) (FIG. 13)

5',3'-O-di-tert-butylsilanediyladenosine (72)

Di-tert-Butylsilylditriflate (50 g, 113 mmol) was added dropwise in the course of 30 min to a stirred suspension of adenosine (71) (27.5 g, 103 mmol) in DMF (200 ml) at 0° C. The resulting solution was stirred at 0° C. for 30 min and then imidazole (16.2 g, 237 mmol) was added at once. The mixture was stirred at 0° C. for 45 min and the precipitate of (72) was filtered out, washed with methanol and dried in vacuo to give 31 g of (72) as white fine powder. Evaporation of mother liquor and trituration the residue with methanol provided the second crop of (72), 4.9 g. Combined yield of (72) was 35.9 g (85.5%).

5',3'-O-di-tert-butylsilanediyl-2'-O-methyladenosine (73)

Compound (72) (35.9 g, 88.1 mmol) was dissolved in mixture of 1-methyl-2-pyrrolidinone (60 ml) and DMF (240 ml) at 80° C. The resulting solution was cooled to −35° C. and dimethylsulfate (20.9 ml, 220.4 mmol) was added. Sodium hydride (5.99 g as 60% suspension in mineral oil, 149.8 mmol) was washed with ca. 75 ml of toluene and then suspended in toluene (approximately 15 ml). The resulting suspension was added to the reaction mixture dropwise via syringe while stirring. The reaction was allowed to proceed at −35° C. until nearly all starting material was consumed (about 4 h). The reaction was quenched by careful addition of methanol (200 ml) followed by water (100 ml). The resulting suspension was stirred 30 min at −20−−30° C. The precipitate of (73) was filtered out and washed with methanol twice on filter bed and then dried in vacuo to give 28.1 g of crude (73) having about 85% of purity. Yield 60–65%.

2'-O-Me-N6-benzoyladenosine (75)

A suspension of crude (73) (28.1 g, ca. 56 mmol) in 170 ml of pyridine was treated with benzoyl chloride (13 ml, 112 mmol) at 0° C. and the reaction stirred overnight at room temperature. Morpholine (20.5 ml, 256 mmol) was added to reaction mixture at 0° C. and the mixture was stirred at 0° C. for 1.5 h and then concentrated in vacuo. The residue was partitioned between dichloromethane and water. The organic layer was washed with another portion of water, dried over magnesium sulfate and concentrated to give crude (74) as colored foam. The latter was dissolved in dichloromethane (210 ml) and pyridine (18 ml), cooled to 0° C. and treated with hydrogen fluoride—pyridine (Aldrich, 70%, 3.3 ml, 127 mmol). The mixture was stirred at 0° C. for 2 h, and the precipitate was filtered out and washed with dichloromethane to give 19.0 g of crude (75). The mother liquor was evaporated and the residue was crystallized from mixture of acetone (20 ml) and methanol (3 ml) to give the second crop of crude (75), 3.1 g. All crude (75) (22.1 g) was recrystallized from methanol (60 ml) to give 15.9 g of pure (75). Overall yield was 40.1% based on adenosine (71) starting material.

EXAMPLE 10

Synthesis of 1,4-Anhydro-2-deoxy-D-erythro-pentitol Derivatives (FIG. 15)

5-O-tert-Butyldimethylsilyl-1,4-anhydro-2-deoxy-D-erytro-pentitol (85a)

Methanesulfonic acid (0.65 ml, 10 mmol) was added dropwise to 30 ml HMDS and the resulting suspension was refluxed under argon atmosphere until it became homogenous (ca. 45 min). 5'-O-tert-butyldimethylsilyl thymidine (82a, 3.56 g, 10 mmol) was added to resulting solution and the mixture was heated under reflux for 3 h. This reaction solution of 83a was brought to room temperature, transferred into a hydrogenation flask and was subjected to hydrogenation over Pd/C (10%, 0.3 g) under 35 psi hydrogen pressure for 1 h at room temperature. Catalyst was filtered out, filtrate was evaporated and the residue was dissolved in 35 ml of dichloromethane. Resulting solution was added slowly to a stirred solution of monobasic sodium phosphate (15%, 15 ml). The mixture was stirred vigorously for 15 min, treated with 2 g of celite and thymine with celite was filtered out. The organic phase was separated, washed with saturated sodium bicarbonate, dried over sodium sulfate and evaporated to dryness. Crude 84a was dissolved in methanol (20 ml) and pyridinium trifluoroacetate (0.1 g, 0.5 mmol) was added to the solution. After 30 min, methanol was stripped out and crude 85a was purified by column chromatography on silica gel using gradient of 20–30% ethyl acetate in hexanes to provide 1.8 g (77.6%) of pure 85a as a slightly yellow oil. $^1$H NMR (CDCl$_3$) δ4.40 (m, 1 H, H3), 4.02 (dd, 2 H, $J_{1a,1b}$=8.2 Hz, $J_{1,2}$=5.4 Hz, H1a, H1b), 3.84 (m, 2 H, H4, H5a), 3.61 (dd, 1H, $J_{5a,5b}$=11.6 Hz, $J_{5,4}$=7.6 Hz, H5b), 2.24 (m, 1 H, H2a), 1.98 (m, 1 H, H2b), 1.96 (m, 1 H, OH), 0.98 (s, 9 H, t-Bu), 0.15 (s, 6 H, Me). The use of different catalysts in the conversion of 82 to 83 is shown in Table II.

3-O-Dimethoxytrityl-5-O-tert-butyldimethylsilyl-1,4-anhydro-2-deoxy-D-erytro-pentitol (86a)

5'-O-tert-butyldimethylsilyl thymidine (82a, 28.52 g, 80 mmol) was converted to crude 85a as it was described above. Thus prepared crude 85a was co-evaporated with pyridine (100 ml) and then dissolved in pyridine (80 ml). Dimethoxytritylchloride (24.4 g, 72 mmol) and dimethylaminopyridine (1 g, 8.2 mmol) were added and the reaction was allowed to proceed overnight at room temperature. After concentration under reduced pressure the mixture was partitioned between dichloromethane and water. The organic phase was separated, washed with saturated sodium bicarbonate, dried over sodium sulfate and evaporated to give brown residue. The residue was purified by column chromatography on silica gel using a gradient of 5–10% ethyl acetate-hexanes to provide 86a as an yellowish oil. Yield 29.8 g (69.6%). $^1$H NMR (CDCl$_3$) δ: 7.43 (m, 9 H, Ph), 6.92 (m, 4 H, Ph), 4.21 (m, 1 H, H3), 4.02 (m, 1H, H4), 396 (m, 2H, H1a, H1b), 3.88 (s, 6 H, OCH$_3$), 3.54 (dd, 1 H, $J_{5a,5b}$=11.1 Hz, $J_{5a,4}$=3.2 Hz, H5a), 3.38 (dd, 1 H, $J_{5b,5a}$=11,1 Hz, $J_{5b,4}$=4.4 Hz, H5b), 1.54 (m, 1 H, H2a), 1.32 (m,1H, H2b), 0.89 (s, 9 H, t-Bu), 0.04 (s, 3 H, Me), 0.02 (s, 3 H, Me).

3-O-Dimethoxytrityl-1,4-anhydro-2-deoxy-D-erytro-pentitol (87)

Sodium hydroxide (10 N solution, 9 ml) was added to a solution of 86 a (16.2 g, 29.6 mmol) in ethanol (120 ml) and the reaction mixture was refluxed for 6 h. After cooling to room temperature the reaction mixture was evaporated under reduced pressure and partitioned between dichloromethane and water. The organic layer was washed with water followed by monobasic sodium phosphate solution (15%), dried over sodium sulfate and evaporated. The residue was purified by flash chromatography on silica gel using a gradient of 40–60% ethyl acetate-hexanes to provide 11.6 g (93.2%) of 87 as a white foam. $^1$H NMR (DMSO-d$_6$) δ: 7.36 (m, 9 H, Ph), 6.96 (m, 4 H, Ph), 4.52 (t, 1 H, $J_{OH,5}$=5.6 Hz, OH), 4.10 (m, 1 H, H3), 3.81 (s, 6 H, OCH$_3$), 3.75 (m, 3 H, H1a, H1b, H4), 3.18 (m, 1 H, H5a), 3.13 (m, 1H, H5b), 1.48 (m, 1 H, H2a), 1.19 (m, 1 H, H2b).

3-O-Dimethoxytrityl-1,4-anhydro-2-deoxy-D-erytro-pentitol-5-succinate, Triethylammonium Salt (88)

Succinic anhydride (3.07 g, 30.7 mmol) and DMAP (0.34 g, 2.8 mmol) were added to a solution of 87 (11.6 g, 27.6 mmol) in pyridine (30 ml) and the reaction was allowed to proceed at 40° C. overnight. After concentration under reduced pressure the residue was partitioned between ethyl acetate and water. The organic layer was separated, washed with cold 10% citric acid followed by water, dried over magnesium sulfate and evaporated. The residue was dissolved in dichloromethane (60 ml), treated with triethylamine (5.8 ml, 41.4 mmol) and the mixture was loaded on silica gel column, previously equilibrated with mixture of 2% MeOH and 2% triethylamine in dichloromethane. After elution with mixture of 3–10% of methanol and 0.5% of triethylamine in dichloromethane appropriate fractions were combined, evaporated and dried in vaccuo overnight to furnish 88 as a white foam. Yield 14.9 g, 87%. $^1$H NMR (CDCl$_3$) δ: 7.40 (m, 9 H, Ph), 6.92 (m, 4 H, Ph), 4.16 (m, 1 H, H3), 3.98 (m, 4 H, H1a, H1b, H4, H5a), 3.87 (s, 6 H, OCH$_3$), 3.65 (m, 1 H, H5b), 3.04 (q, 6 H, CH$_3$—CH$_2$—N), 2.58 (m, 4 H, CO—CH$_2$—CH$_2$—CO), 1.63 (m, 1H, H2a), 1.53 (m, 1 H, H2b), 1.27 (t, 9 H, CH$_3$—CH$_2$—N).

Example 11

Substituted Phthalimide Nucleosides

Compounds 5b–e (FIG. 3) were synthesized from compounds 4b–e respectively according to conditions in FIG. 3. Four cytidine 5'-O-dimethoxytrityl-2'-deoxy-2'-phthalimides (compounds 7b–e, FIG. 3) were converted to 5'-O-DMT-2'-amino cytidine under differing conditions (40% aq methylamine, methanolic methylamine, and methanolic methylamine with 10% water). Complete phthaloyl deprotection as determined by thin layer chromatography (TLC) was observed in all cases after 2–3 hours at room temperature in the formation of 5'-DMT-2'-deoxy-2'-amino cytidine (see Table 1).

TABLE 1

Triflate Displacement with different Phthalimides

| Compound | Reaction conditions | Yield of phthalimide deriv. From 3 | Yield of elimination |
|---|---|---|---|
| 5a | 60° C., 3 h then Rt overnight | 60 | 10–20 |
| 5b | RT, 20 h | 56 | 10–20 |
| 5c | 70–80° C., 3 h | 70 | traces |
| 5d | RT, 20 h | 40 | 20 |
| 5e | RT, 20 h | 35 | 20 |

RT is room temperature; h is hours; and deriv. is derivative.

TABLE 2

Depyrimidination of Thymidine derivatives with different catalysts

| Starting material (amount of mmol) | Depyrimidination catalyst (amount of equivalents) | Product | Yield g | % |
|---|---|---|---|---|
| 76 a (10) | H$_2$SO$_4$ (0.1 eq) | 81 a | 1.61 | 69.3 |
| 76 a (10) | p-TsOH (0.3 eq) | 81 a | 1.72 | 74.0 |
| 76 a (10) | (NH$_4$)$_2$SO$_4$ (0.37 eq) | 81 a | 1.44 | 62.1 |
| 76 b (10) | MsOH (1 eq) | 81 b | 1.88 | 68.4 |
| 76 c (10) | MsOH (1 eq) | 81 c | 2.34 | 65.7 |

These examples are meant to be non-limiting and those skilled in the art will recognize that similar strategies, as described in the present invention, can be readily adapted to synthesize other nucleosides and nucleoside analogs, including other 2'deoxy-2'-N-phthaloyl, 2'-deoxy-2'-amino, 2'-O- methyl, L and D ribo nucleosides, C-nucleosides, nucleoside analogs and C-nucleoside analogs and are within the scope of this invention.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed can be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The invention illustratively described herein suitably can be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed can be resorted to by those skilled in the art, and that such modifications and variations are considered to be within the scope of this invention as defined by the description and the appended claims.

A person skilled in the art will recognize that use of the methods and processes of the instant invention is not limited to the compounds described herein and can be applied to the synthesis of many different nucleoside and non-nucleoside molecules containing amino, and/or N-phthaloyl groups as well as those molecules containing L-ribose sugar and/or D-ribose sugar functions. Non-limiting examples of modified nucleosides that are contemplated by the instant invention are reviewed by Usman and Cedergren, 1992, TIBS. 17, 34; Usman et al., 1994, Nucleic Acids Symp. Ser. 31, 163; Burgin et al., 1996, Biochemistry, 35, 14090.

Other embodiments are within the following claims.

What is claimed is:

1. A method for synthesizing a compound of Formula I:

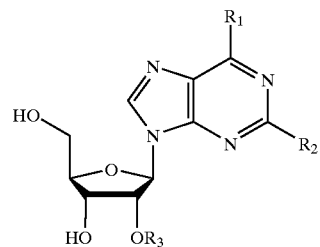

wherein $R_1$ and $R_2$ are independently hydrogen, $NR_{10}R_{11}$, $(NR_{10}R_{11})$alkyl, alkyl, fluoro or chloro, wherein $R_{10}$ and $R_{11}$ are independently hydrogen, alkyl, alkanoyl, acyl, alkoxy, or arylalkyl optionally substituted with up to three groups that are independently halogen, alkoxy, nitro, or alkyl; and $R_3$ is independently alkyl, alkoxyalkyl, alkyl-thio-alkyl, cyanoalkyl, or arylalkyl optionally substituted with up to three groups that are independently halogen, alkoxy, nitro, or alkyl; comprising:

a) introducing a 5',3'-bridging silyl protecting group to a compound of Formula II,

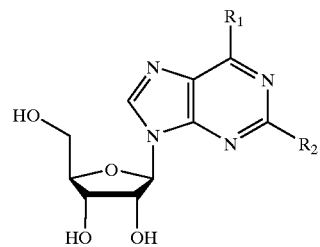

wherein $R_1$ and $R_2$ are as defined in Formula I, to yield a compound of Formula III;

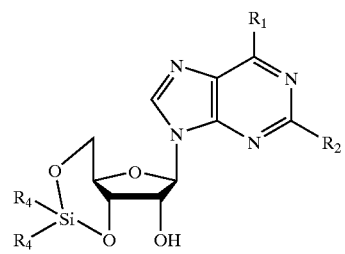

wherein $R_1$ and $R_2$ are as defined in Formula I and each $R_4$ is independently alkyl, aryl or isoalkyl;

b) alkylating the product of step (a) to yield a compound of Formula IV;

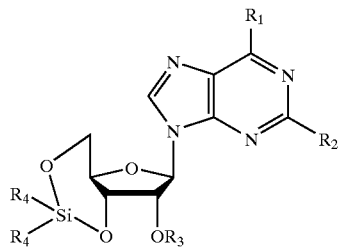

wherein $R_1$, $R_2$ and $R_3$ are as defined in Formula I and $R_4$ is as defined in Formula III; and c) deprotecting the product of step (b) to yield a compound of Formula I.

2. A method for synthesizing a compound having Formula V:

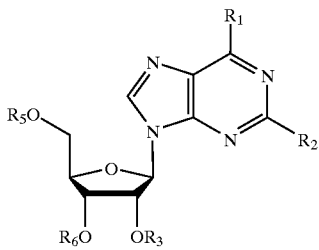

wherein $R_1$ and $R_2$ are independently hydrogen, $NR_{10}R_{11}$, $(NR_{10}R_{11})$alkyl, alkyl, fluoro or chloro, wherein $R_{10}$ and $R_{11}$ are independently hydrogen, alkyl, alkanoyl, acyl, alkoxy, or arylalkyl optionally substituted with up to three groups that are independently halogen, alkoxy, nitro, or alkyl; $R_3$ is independently alkyl, alkoxyalkyl, alkyl-thio-alkyl, cyanoalkyl, or arylalkyl optionally substituted with up to three groups that are independently halogen, alkoxy, nitro, or alkyl; $R_5$ is an acid labile protecting moiety; and $R_6$ is a phosphorous containing moiety; comprising:

a) introducing a 5',3'-bridging silyl protecting group to a compound of Formula II to yield a compound of Formula III;

b) alkylating the product of step (a) to yield a compound of Formula IV;

c) introducing at least one exocyclic amine protecting moiety to the product of step (b) provided that at least one of $R_1$ or $R_2$ in step (b) is amino;

d) deprotecting the product of step (c) to yield a compound of Formula I; and e) introducing an acid labile protecting moiety followed by a phosphorous containing moiety to the product of step (d) to yield a compound of Formula V.

3. The method of claim 1 or 2, wherein $R_4$ is tert-butyl.

4. The method of claim 1 or 2, wherein $R_1$ is amino and $R_2$ is H.

5. The method of claim 1 or 2, wherein $R_1$ and $R_2$ are amino.

6. The method of claim 1 or 2, wherein $R_1$ is chloro and $R_2$ is H.

7. The method of claim 1, wherein the compound of Formula I is 2'-O-methyl adenosine.

8. The method of claim 2, wherein the compound of Formula V is 5'-O-dimethoxytrityl-2'-O-methyl-N2-benzoyl adenosine 3'-O-(2-cyanoethyl-N,N-diisopropylphosphoramidite).

9. The method of claim 1 or 2, wherein said alkylation in step (b) is conducted in the presence of an alkyl halide and a base.

10. A method for synthesizing a compound having Formula VI:

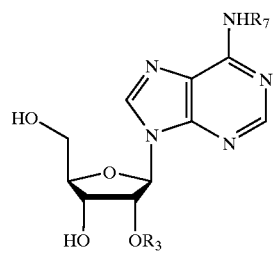

wherein $R_3$ is independently alkyl, alkoxyalkyl, alkyl-thio-alkyl, cyanoalkyl, or arylalkyl optionally substituted with up to three groups that are independently halogen, alkoxy, nitro, or alkyl; and $R_7$ is H, acyl, or arylalkanoyl, comprising:

a) introducing a 5',3'-bridging silyl protecting group to inosine to yield a compound of Formula VII;

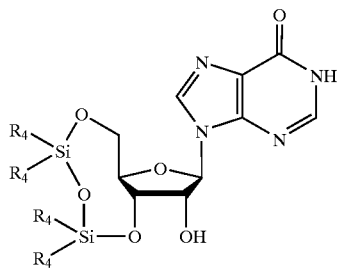

wherein each $R_4$ is independently alkyl, aryl or isoalkyl;

b) introducing an imidazole moiety to the product of step (a) to yield a compound of Formula VIII;

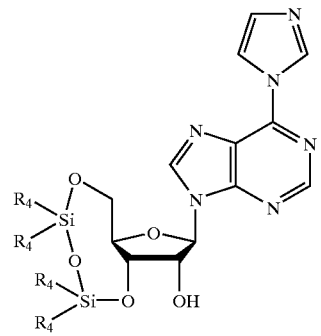

wherein each $R_4$ is independently alkyl, aryl or isoalkyl;

c) alkylating the product of step (b) to yield a compound of Formula IX;

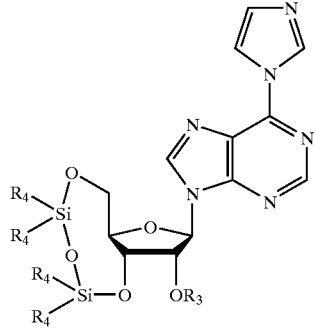

wherein each R₄ is independently alkyl, aryl or isoalkyl and R₃ is as defined in Formula VI;

d) aminating the product of step (c) to yield a compound of Formula X;

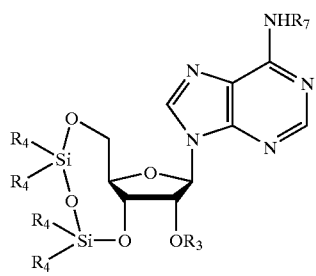

wherein R₃ and R₇ are as defined in Formula VI; and e) desilylating the product of step (d) to yield a compound of Formula VI.

11. A method for synthesizing a compound having Formula VI, comprising:

a) introducing a 5',3'-bridging silyl protecting group to inosine to yield a compound of Formula XI;

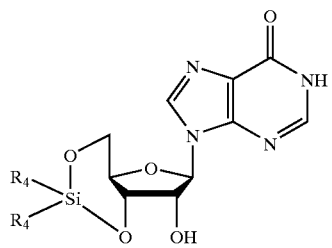

wherein each R₄ is independently alkyl aryl or isoalkyl;

b) introducing an imidazole moiety to the product of step (a) to yield a compound of Formula XII;

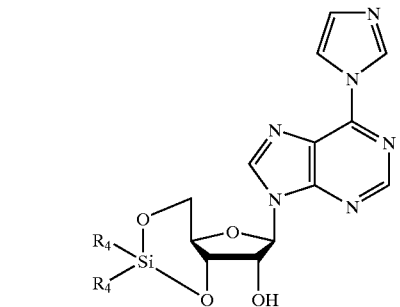

wherein each R₄ is independently alkyl, aryl or isoalkyl;

c) alkylating the product of step (b) to yield a compound of Formula XIII;

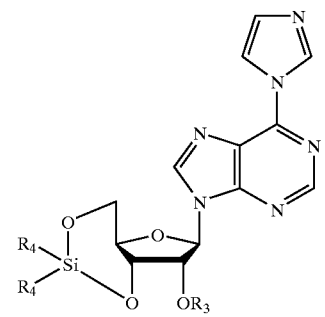

wherein R₃ is as defined in Formula VI and each R₄ is independently alkyl, aryl or isoalkyl;

d) aminating the product of step (c) to yield a compound of Formula XIV;

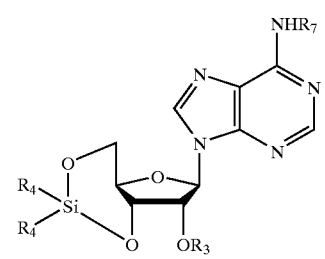

wherein R₃ and R₇ are as defined in Formula VI; and e) desilylating the product of step (d) to yield a compound of Formula VI.

12. The method of any of claim 10 or 11, further comprising the step of:

a) introducing an acid labile protecting moiety followed by a phosphorous containing moiety to the product of step (e) to yield a compound of Formula XV;

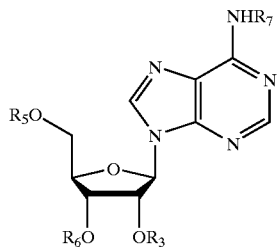

wherein $R_7$ and $R_3$ are as defined in Formula VI, $R_5$ is an acid labile protecting moiety and $R_6$ is a phosphorous containing moiety.

13. The method of claim 10, wherein $R_4$ is isopropyl.
14. The method of claim 11, wherein $R_4$ is tert-butyl.
15. The method of any of claim 10 or 11, wherein $R_3$ is methyl.
16. The method of claim 12, wherein $R_3$ is methyl.
17. The method of claim 10 or 11, wherein the compound of Formula VI is 2'-O-methyl adenosine.
18. The method of claim 10 or 11, wherein the alkylation in step (c) is in the presence of methyl iodide and sodium hydride.
19. The method of claim 12, wherein the acyl moiety is a benzoyl moiety.
20. The method of claim 12, wherein the compound of Formula XV is 5'-O-dimethoxytrityl-2'-O-methyl-N2-benzoyl adenosine 3'-O-(2-cyanoethyl-N,N-diisopropylphosphoramidite).
21. A method for synthesizing a compound having Formula XVI:

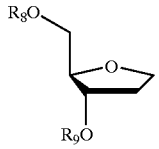

wherein $R_8$ is a succinate moiety, aklylsilyl moiety, or H; and $R_9$ is an acid labile protecting moiety or H, comprising:
a) depyrimidination of a compound of formula XVII;

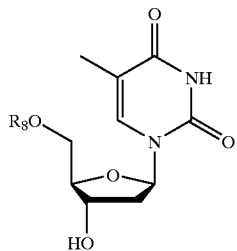

wherein $R_8$ is an silylalkyl moiety to yield a compound of Formula XVI, wherein $R_8$ is an silylalkyl moiety; and $R_9$ is H;
b) introducing an acid labile protecting moiety to the product of step (a) to yield a compound of Formula XVI, wherein $R_8$ is an silylalkyl moiety and $R_9$ is an acid labile protecting moiety;
c) deprotecting the product of step (b) to yield a compound for Formula XVI, wherein $R_8$ is H and $R_9$ is an acid labile protecting moiety; and
d) introducing a succinate moiety to the product of step (c) to yield a compound of Formula XVI, wherein $R_8$ is a succinate moiety and $R_9$ is an acid labile protecting moiety.

22. A method for synthesizing a compound having Formula XVI:

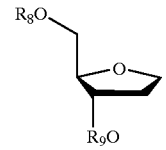

wherein $R_8$ is a phosphorous containing moiety, aklylsilyl moiety, or H; and $R_9$ is an acid labile protecting moiety or H, comprising:
a) depyrimidination of a compound of formula XVII;

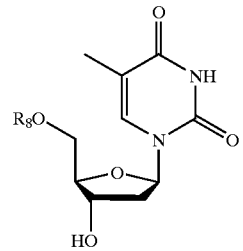

wherein $R_8$ is an aklylsilyl moiety to yield a compound of Formula XVI, wherein $R_8$ is an silylalkyl moiety and $R_9$ is H;
b) introducing an acid labile protecting moiety to the product of step (a) to yield a compound of Formula XVI, wherein $R_8$ is an silylalkyl moiety and $R_9$ is an acid labile protecting moiety;
c) deprotecting the product of step (b) to yield a compound for Formula XVI, wherein $R_8$ is H and $R_9$ is an acid labile protecting moiety; and
d) introducing a phosphorous containing moiety to the product of step (c) under conditions suitable to yield a compound of Formula XVI, wherein $R_8$ is a phosphorous containing moiety and $R_9$ is an acid labile protecting moiety.

23. The method of claim 21 or 22, wherein the silylalkyl moiety of Formula XVII is tert-butyldimethylsilyl, tert-butyldiphenylsilyl, or triisopropylsilyl.
24. The method of claim 21 or 22, wherein step (b) comprises treatment of the product of step (a) with a silylating reagent and a catalyst followed by hydrogenation and selective desilylation to yield said compound of Formula XVI, wherein $R_8$ is an silylalkyl moiety and $R_9$ is H.
25. The method of claim 24, wherein the silylating reagent comprises hexamethyldisilazane.
26. The method of claim 24, wherein the catalyst is sulfuric acid, para-toluene sulfonic acid, or ammonium sulfate.
27. The method of claim 24, wherein the catalyst is a sulfonic acid, sulfonyl halide, sulfonate or sulfamide.
28. The method of claim 27, wherein the sulfonic acid is methanesulfonic acid or trifluoromethanesulfonic acid.
29. The method of claim 27, wherein the sulfamide is methanesulfamide or sulfamide.
30. The method of claim 27, wherein the sulfonyl halide is methanesulfonylchloride.
31. The method of claim 27, wherein the sulfonate is trimethylsilylmethane sulfonate.
32. The method of claim 24, wherein the selective desilylation comprises treatment with pyridinium trifluoroacetate.

33. The method of claim 24, wherein the hydrogenation is catalytic hydrogenation with hydrogen gas and palladium on carbon.

34. The method of claim 21 or 22, wherein the deprotection conditions in step (c) comprise treatment with sodium hydroxide in ethanol.

35. The method of claim 21, wherein the compound of Formula XVI of step (d) is 3-O-dimethoxytrityl-1,4-anhydro-2-deoxy-D-erythro-pentitol-5-O-succinate.

36. The method of claim 22, wherein the compound of Formula XVI of step (d) is 3-O-dimethoxytrityl-1,4-anhydro-2-deoxy-D-erythro-pentitol-5-O-(2-cyanoethyl-N,N-diisopropylphosphoramidite).

37. The method of any of claim 2, 21 or 22, wherein the acid labile protecting moiety is dimethoxytrityl, monomethoxytrityl, or trityl.

38. The method of claim 12, wherein the acid labile protecting moiety is dimethoxytrityl, monomethoxytrityl, or trityl.

39. The method of any of claim 2, 21 or 22, wherein the phosphorous containing moiety is a phosphoramidite moiety.

40. The method of claim 12, wherein the phosphorous containing moiety is a phosphoramidite moiety.

41. The method of any of claim 2, 21 or 22, wherein the phosphorous containing moiety is a triphosphate moiety.

42. The method of claim 12, wherein the phosphorous containing moiety is a triphosphate moiety.

43. The method of claim 40, wherein the phosphoramidite moiety is a 3'-O-(2-cyanoethyl-N,N-diisopropylphosphoramidite) moiety.

44. The method of claim 10 or 11, wherein the amination in step (d) is amination with ammonia.

45. The method of claim 10 or 11, wherein the amination in step (d) is amination with an acylamide.

46. The method of claim 45, wherein the acylamide is benzamide.

47. The method of claim 1, wherein the 5',3'-bridging silyl protecting group is introduced using di-tert-butylsilylbis (trifluoromethanesulfonate) in the presence of a base.

48. The method of claim 2, wherein the 5',3'-bridging silyl protecting group is introduced using 1,3-dichloro-1,1,3,3-tetraisopropyldisiloxane in the presence of a base.

49. The method of claim 47 or 48, wherein the base is triethylamine, diisopropylethylamine, pyridine, collidine, lutidine, 1-methylimidazole, imidazole, N,N-dimethylaminopyridine, or combinations thereof.

50. The method of claim 10 or 11, wherein said alkylation in step (c) is conducted in the presence of an alkyl halide and a base.

51. The method of claim 50 wherein the alkyl halide is methyl iodide and the base is sodium hydride.

52. The method of claim 1 or 2, wherein the deprotection of the 5' and 3' hydroxyls is performed using a reagent that is an acid, a fluoride source, or a combination thereof.

53. The method of claim 52 wherein the reagent is HF/pyridine, tetrabutylammonium fluoride, aqueous HF solution, HF gas, or HF/triethylamine adduct.

54. The method of claim 1, wherein steps (a), (b), and (c) are independently performed at a temperature of about −20° C. to about 50° C.

55. The method of claim 2, wherein steps (a), (b), (c), (d) and (e) are independently performed at a temperature of about −20° C. to about 50° C.

56. The method of claim 10, wherein steps (a), (b), (c), (d) and (e) are independently performed at a temperature of about −20° C. to about 50° C.

57. The method of claim 11, wherein steps (a), (b), (c), (d) and (e) are independently performed at a temperature of about −20° C. to about 50° C.

58. The method of claim 12, wherein step (a) is performed at a temperature of about −20° C. to about 50° C.

59. The method of claim 21, wherein steps (a), (b), (c), and (d) are independently performed at a temperature of about −20° C. to about 50° C.

60. The method of claim 2, wherein the phosphorous containing moiety in step (e) is introduced with a chlorophosphine and a base.

61. The method of claim 12, wherein the phosphorous containing moiety in step (a) is introduced with a chlorophosphine and a base.

62. The method of claim 21 or 22, wherein the phosphorous containing moiety in step (d) is introduced with a chlorophosphine and a base.

63. The method of claims 60 and 61, wherein the base is triethylamine, diisopropylethylamine, pyridine, collidine, lutidine, 1-methylimidazole, imidazole, N,N-dimethylaminopyridine, or combinations thereof.

64. The method of claim 62, wherein the base is triethylamine, diisopropylethylamine, pyridine, collidine, lutidine, 1-methylimidazole, imidazole, N,N-dimethylaminopyridine, or combinations thereof.

65. A compound of Formula VIII;

wherein each $R_4$ is independently alkyl, aryl or isoalkyl.

66. A compound of Formula IX;

wherein $R_3$ is independently alkyl, alkoxyalkyl, alkyl-thioalkyl, cyanoalkyl, or arylalkyl optionally substituted with up to three groups that are independently halogen, alkoxy, nitro, or alkyl and each $R_4$ is independently alkyl, aryl or isoalkyl.

67. A compound of Formula XII;

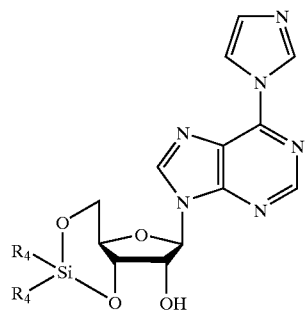

wherein each $R_4$ is independently alkyl, aryl or isoalkyl.

68. A compound of Formula XIII;

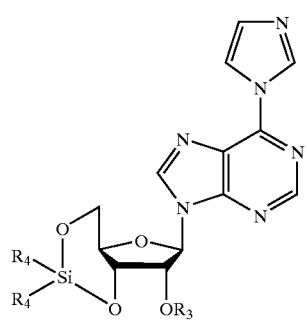

wherein $R_3$ is independently alkyl, alkoxyalkyl, alkyl-thioalkyl, cyanoalkyl, or arylalkyl optionally substituted with up to three groups that are independently halogen, alkoxy, nitro, or alkyl and each $R_4$ is independently alkyl, aryl or isoalkyl.

69. The compound of claim 65 or 66, wherein $R_4$ is isopropyl.

70. The compound of claim 67 or 68, wherein $R_4$ is tert-butyl.

71. The compound of claim 66 or 68, wherein $R_3$ is methyl.

72. The method of claim 9 wherein the alkyl halide is methyl iodide and the base is sodium hydride.

73. The method of claim 10 or 11, wherein the imidazole moiety is introduced in the presence of a phosphourous reagent, halogenated alkane, and imidazole.

74. The method of claim 73, wherein the phosphorous reagent is triphenylphosphine.

75. The method of claim 73, wherein the halogenated alkane is carbon tetrachloride.

* * * * *